US012195777B2

(12) United States Patent
Heron

(10) Patent No.: US 12,195,777 B2
(45) Date of Patent: Jan. 14, 2025

(54) POLYNUCLEOTIDE SYNTHESIS METHOD, KIT AND SYSTEM

(71) Applicant: Oxford Nanepore Technologies PLC, Oxford (GB)

(72) Inventor: Andrew John Heron, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 428 days.

(21) Appl. No.: 16/966,430

(22) PCT Filed: Feb. 4, 2019

(86) PCT No.: PCT/GB2019/050296
§ 371 (c)(1),
(2) Date: Jul. 30, 2020

(87) PCT Pub. No.: WO2019/150134
PCT Pub. Date: Aug. 8, 2019

(65) Prior Publication Data
US 2022/0177937 A1 Jun. 9, 2022

(30) Foreign Application Priority Data
Feb. 2, 2018 (GB) ...................................... 1801768

(51) Int. Cl.
*C12P 19/34* (2006.01)
(52) U.S. Cl.
CPC .................................... *C12P 19/34* (2013.01)
(58) Field of Classification Search
CPC ........ C12P 19/34; C12N 15/11; C12Q 1/6844
USPC ...................... 435/6.1, 91.1, 91.31; 536/23.1
See application file for complete search history.

(56) References Cited

U.S. PATENT DOCUMENTS

| | | | |
|---|---|---|---|
| 5,795,782 A | 8/1998 | Church et al. | |
| 6,015,714 A | 1/2000 | Baldarelli et al. | |
| 6,267,872 B1 | 7/2001 | Akeson et al. | |
| 6,362,002 B1 | 3/2002 | Denison et al. | |
| 6,464,842 B1 | 10/2002 | Golovchenko et al. | |
| 6,627,067 B1 | 9/2003 | Branton et al. | |
| 6,673,615 B2 | 1/2004 | Denison et al. | |
| 6,746,594 B2 | 6/2004 | Akeson et al. | |
| 7,060,440 B1 | 6/2006 | Kless | |
| 7,253,434 B2 | 8/2007 | Golovchenko et al. | |
| 7,258,838 B2 | 8/2007 | Li et al. | |
| 7,466,069 B2 | 12/2008 | Golovchenko et al. | |
| 7,468,271 B2 | 12/2008 | Golovchenko et al. | |
| 8,653,832 B2 | 2/2014 | Hadwen et al. | |
| 8,828,336 B2 | 9/2014 | Hadwen et al. | |
| 9,222,082 B2 | 12/2015 | Jayasinghe et al. | |
| 2003/0104428 A1 | 6/2003 | Branton et al. | |
| 2004/0001371 A1 | 1/2004 | Mansuripur et al. | |
| 2004/0121525 A1 | 6/2004 | Chopra et al. | |
| 2007/0004047 A1 | 1/2007 | Lee et al. | |
| 2014/0197028 A1 | 7/2014 | Jacobs et al. | |
| 2014/0202863 A1 | 7/2014 | Hadwen | |
| 2014/0363852 A1 | 12/2014 | Efcavitch et al. | |
| 2015/0344944 A1 | 12/2015 | Reid et al. | |
| 2016/0046973 A1 | 2/2016 | Efcavitch et al. | |
| 2016/0108382 A1 | 4/2016 | Efcavitch et al. | |
| 2016/0168611 A1 | 6/2016 | Efcavitch et al. | |
| 2022/0042967 A1 | 2/2022 | Brown et al. | |

FOREIGN PATENT DOCUMENTS

| | | | |
|---|---|---|---|
| WO | 2000/028312 A1 | 5/2000 | |
| WO | 2000/079257 A1 | 12/2000 | |
| WO | 2003/003446 A2 | 1/2003 | |
| WO | 2005/061373 A1 | 7/2005 | |
| WO | 2005/124888 A1 | 12/2005 | |
| WO | 2006/028508 A2 | 3/2006 | |
| WO | 2006/100484 A2 | 9/2006 | |
| WO | 2008/102120 A1 | 8/2008 | |
| WO | 2008/102121 A1 | 8/2008 | |
| WO | 2009/020682 A2 | 2/2009 | |
| WO | 2009/035647 A1 | 3/2009 | |
| WO | 2009/077734 A2 | 6/2009 | |
| WO | 2010/004265 A1 | 1/2010 | |
| WO | 2010/004273 A1 | 1/2010 | |

(Continued)

OTHER PUBLICATIONS

International Preliminary Report on Patentability for Application No. PCT/GB2019/050296, mailed Aug. 13, 2020.
International Search Report and Written Opinion for Application No. PCT/GB2019/053669, mailed Apr. 14, 2020.
International Preliminary Report on Patentability for Application No. PCT/GB2019/053669, mailed Jul. 1, 2021.
Altschul et al., Basic local alignment search tool. J Mol Biol. Oct. 5, 1990;215(3):403-10. doi: 10.1016/S0022-2836(05)80360-2.
Altschul, A protein alignment scoring system sensitive at all evolutionary distances. J Mol Evol. Mar. 1993;36(3):290-300. doi: 10.1007/BF00160485.
Chari et al., Beyond editing to writing large genomes. Nat Rev Genet. Dec. 2017;18(12):749-760. doi: 10.1038/nrg.2017.59. Epub Aug. 30, 2017. Author Manuscript, 30 pages.

(Continued)

*Primary Examiner* — Jane J Zara
(74) *Attorney, Agent, or Firm* — Wolf, Greenfield & Sacks, P.C.

(57) ABSTRACT

The invention relates to new in vitro methods for synthesising a polymer, particularly a polynucleotide molecule, having a pre-defined sequence of units such as nucleotides. For synthesising a polynucleotide molecule the methods involve a process of extending a polynucleotide synthesis molecule with a transfer nucleotide. The methods additionally involve repeating the extension process multiple times to iteratively extend the polynucleotide molecule with multiple transfer nucleotides to generate a new polynucleotide molecule having a pre-defined nucleotide sequence. The invention also relates to in vitro methods of joining multiple synthetic polynucleotides following synthesis to form larger synthetic polynucleotides, as well as devices and systems for performing the extension, synthesis and assembly methods of the invention.

21 Claims, 22 Drawing Sheets

Specification includes a Sequence Listing.

(56) References Cited

FOREIGN PATENT DOCUMENTS

| | | | |
|---|---|---|---|
| WO | 2010/086602 A1 | 8/2010 | |
| WO | 2010/086603 A1 | 8/2010 | |
| WO | 2010/109197 A2 | 9/2010 | |
| WO | 2010/122293 A1 | 10/2010 | |
| WO | 2011/046706 A1 | 4/2011 | |
| WO | 2011/067559 A1 | 6/2011 | |
| WO | 2012/005857 A1 | 1/2012 | |
| WO | 2012/033524 A2 | 3/2012 | |
| WO | 2012/042226 A2 | 4/2012 | |
| WO | 2012/107778 A2 | 8/2012 | |
| WO | 2012/164270 A1 | 12/2012 | |
| WO | 2013/057495 A2 | 4/2013 | |
| WO | 2013/083983 A1 | 6/2013 | |
| WO | 2013/098561 A1 | 7/2013 | |
| WO | 2013/098562 A2 | 7/2013 | |
| WO | 2013/153359 A1 | 10/2013 | |
| WO | 2014/013259 A1 | 1/2014 | |
| WO | 2014/013260 A1 | 1/2014 | |
| WO | 2014/013262 A1 | 1/2014 | |
| WO | 2014/064443 A2 | 5/2014 | |
| WO | 2014/064444 A1 | 5/2014 | |
| WO | 2015/055981 A2 | 4/2015 | |
| WO | 2015/110813 A1 | 7/2015 | |
| WO | 2016/028843 A2 | 2/2016 | |
| WO | 2016/034591 A2 | 3/2016 | |
| WO | 2016/034807 A1 | 3/2016 | |
| WO | 2016/055777 A2 | 4/2016 | |
| WO | 2016/059375 A1 | 4/2016 | |
| WO | 2016/059427 A1 | 4/2016 | |
| WO | 2016/128731 A1 | 8/2016 | |
| WO | 2016/139477 A1 | 9/2016 | |
| WO | 2017/009663 A1 | 1/2017 | |
| WO | 2017/149293 A1 | 9/2017 | |
| WO | 2017/149316 A1 | 9/2017 | |
| WO | 2017/149317 A1 | 9/2017 | |
| WO | 2017/149318 A1 | 9/2017 | |
| WO | 2017/151680 A2 | 9/2017 | |
| WO | WO-2017184677 A1 * | 10/2017 | ............ C12Q 1/68 |
| WO | 2017/203268 A1 | 11/2017 | |
| WO | 2017/203269 A1 | 11/2017 | |
| WO | 2018/081745 A1 | 5/2018 | |
| WO | 2018/146491 A1 | 8/2018 | |
| WO | 2018/211241 A1 | 11/2018 | |
| WO | 2018/222853 A1 | 12/2018 | |
| WO | 2019/002893 A1 | 1/2019 | |
| WO | 2019/213437 A1 | 11/2019 | |

OTHER PUBLICATIONS

Chavis et al., Single Molecule Nanopore Spectrometry for Peptide Detection. ACS Sens. Sep. 22, 2017;2(9):1319-1328. doi: 10.1021/acssensors.7b00362. Epub Aug. 16, 2017.

Chen et al., Digital data storage using DNA nanostructures and solid-state nanopores. Nano letters. Dec. 26, 2018;19(2):1210-5. doi: 10.1021/acs.nanolett.8b04715.

Colas et al., Microscopical investigations of nisin-loaded nanoliposomes prepared by Mozafari method and their bacterial targeting. Micron. 2007;38(8):841-7. doi: 10.1016/j.micron.2007.06.013. Epub Jul. 3, 2007.

Crnkovic et al., Biological Nanopores: Engineering on Demand. Life (Basel). Jan. 5, 2021;11(1):27. doi: 10.3390/life11010027.

Devereux et al., A comprehensive set of sequence analysis programs for the VAX. Nucleic Acids Res. Jan. 11, 1984; 12(1 Pt 1):387-95. doi: 10.1093/nar/12.1part1.387.

Eliseev et al., Molecular recognition of nucleotides, nucleosides, and sugars by aminocyclodextrins. Journal of the American Chemical Society. Jul. 1994;116(14):6081-8.

Haugland et al., Synthetically Diversified Protein Nanopores: Resolving Click Reaction Mechanisms. ACS Nano. Apr. 23, 2019;13(4):4101-4110. doi: 10.1021/acsnano.8b08691. Epub Mar. 18, 2019.

Holden et al., Direct introduction of single protein channels and pores into lipid bilayers. J Am Chem Soc. May 11, 2005;127(18):6502-3. doi: 10.1021/ja042470p.

Langecker et al., Synthetic lipid membrane channels formed by designed DNA nanostructures. Science. Nov. 16, 2012;338(6109):932-6. doi: 10.1126/science.1225624.

Mayer et al., An Epigenetics-Inspired DNA-Based Data Storage System. Angew Chem Int Ed Engl. Sep. 5, 2016;55(37):11144-8. doi: 10.1002/anie.201605531. Epub Jul. 21, 2016.

Nani et al., Near-IR Light-Mediated Cleavage of Antibody-Drug Conjugates Using Cyanine Photocages. Angew Chem Int Ed Engl. Nov. 9, 2015;54(46):13635-8. doi: 10.1002/anie.201507391. Epub Sep. 25, 2015. Author Manuscript, 10 pages.

Reiner et al., Temperature sculpting in yoctoliter vols. J Am Chem Soc. Feb. 27, 2013;135(8):3087-94. doi: 10.1021/ja309892e. Epub Feb. 14, 2013.

Wang et al., The evolution of nanopore sequencing. Front Genet. Jan. 7, 2015;5:449. doi: 10.3389/fgene.2014.00449.

Yamazaki et al., Label-Free Single-Molecule Thermoscopy Using a Laser-Heated Nanopore. Nano Lett. Nov. 8, 2017;17(11):7067-7074. doi: 10.1021/acs.nanolett.7b03752. Epub Oct. 10, 2017.

PCT/GB2019/050296, Date of Mailing Apr. 15, 2019, International Search Report and Written Opinion.

GB 1801768.1, Date of Mailing Oct. 31, 2018, Combined Search and Examination Report.

Combined Search and Examination Report for Application No. GB1801768.1, mailed Oct. 31, 2018.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10. doi: 10.1021/ja057123+.

Bayley et al., Droplet interface bilayers. Mol Biosyst. Dec. 2008;4(12):1191-208. doi: 10.1039/b808893d. Epub Sep. 5, 2008.

Bayley et al., Stochastic sensors inspired by biology. Nature. Sep. 13, 2001;413(6852):226-30. doi: 10.1038/35093038.

Braha et al., Designed protein pores as components for biosensors. Chem Biol. Jul. 1997;4(7):497-505. doi: 10.1016/s1074-5521(97)90321-5.

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

Chou et al., Recent Advances in Application of Droplet Microfluidics. Micromachines. 2015;6:1249-1271. doi: 10.3390/mi6091249.

Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.

David et al., Chemistry of Glycosylases and Endonucleases Involved in Base-Excision Repair. Chem Rev. May 7, 1998;98(3):1221-1262. doi: 10.1021/cr980321h.

Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.

Farimani et al., DNA Origami-Graphene Hybrid Nanopore for DNA Detection. ACS Appl Mater Interfaces. Jan. 11, 2017;9(1):92-100. doi: 10.1021/acsami.6b11001. Epub Dec. 22, 2016.

Fuller et al., Real-time single-molecule electronic DNA sequencing by synthesis using polymer-tagged nucleotides on a nanopore array. Proc Natl Acad Sci U S A. May 10, 2016;113(19):5233-8. doi: 10.1073/pnas.1601782113. Epub Apr. 18, 2016.

Georges et al., Novel Approach to the Ligation of Single-Stranded DNA Fragments by T4 Dna Ligase—DNA Mobile Multiple-Restriction Fragmens: "UNI-LINKERS" for Cloning of Genes. Nucleosides & Nucleotides. 1989;8(8):1427-1440. doi: 10.1080/07328318908048851.

González-Pérez et al., Biomimetic triblock copolymer membrane arrays: a stable template for functional membrane proteins. Langmuir. Sep. 15, 2009;25(18):10447-50. doi: 10.1021/la902417m.

Haque et al., Solid-State and Biological Nanopore for Real-Time Sensing of Single Chemical and Sequencing of DNA. Nano Today. Feb. 2013;8(1):56-74. doi: 10.1016/j.nantod.2012.12.008.

Heron et al., Simultaneous measurement of ionic current and fluorescence from single protein pores. J Am Chem Soc. Feb. 11, 2009;131(5):1652-3. doi: 10.1021/ja808128s.

(56) References Cited

OTHER PUBLICATIONS

Howorka et al., Building membrane nanopores. Nat Nanotechnol. Jul. 6, 2017;12(7):619-630. doi: 10.1038/nnano.2017.99.

Ivanov et al., DNA tunneling detector embedded in a nanopore. Nano Lett. Jan. 12, 2011;11(1):279-85. doi: 10.1021/nl103873a. Epub Dec. 6, 2010.

Kocalka et al., Rapid and efficient DNA strand cross-linking by click chemistry. Chembiochem. May 23, 2008;9(8):1280-5. doi: 10.1002/cbic.200800006.

Kolb et al., Click Chemistry: Diverse Chemical Function from a Few Good Reactions. Angew Chem Int Ed Engl. Jun. 1, 2001;40(11):2004-2021. doi: 10.1002/1521-3773(20010601)40:11<2004::aid-anie2004>3.3.co;2-x.

Kuhn et al., Template-independent ligation of single-stranded DNA by T4 DNA ligase. FEBS J. Dec. 2005;272(23):5991-6000. doi: 10.1111/j.1742-4658.2005.04954.x.

Kumar et al., PEG-labeled nucleotides and nanopore detection for single molecule DNA sequencing by synthesis. Sci Rep. 2012;2:684. doi: 10.1038/srep00684. Epub Sep. 21, 2012.

Lieberman et al., Processive replication of single DNA molecules in a nanopore catalyzed by phi29 DNA polymerase. J Am Chem Soc. Dec. 22, 2010;132(50):17961-72. doi: 10.1021/ja1087612. Epub Dec. 1, 2010.

Luan et al., Base-by-base ratcheting of single stranded DNA through a solid-state nanopore. Phys Rev Lett. Jun. 11, 2010;104(23):238103. doi: 10.1103/PhysRevLett.104.238103. Epub Jun. 10, 2010.

Magierowski et al., Nanopore-CMOS Interfaces for DNA Sequencing. Biosensors (Basel). Aug. 6, 2016;6(3):42. doi: 10.3390/bios6030042.

Minhaz Ud-Dean, A theoretical model for template-free synthesis of long DNA sequence. Syst Synth Biol. Dec. 2008;2(3-4):67-73. doi: 10.1007/s11693-009-9023-x. Epub Apr. 3, 2009.

Montal et al., Formation of bimolecular membranes from lipid monolayers and a study of their electrical properties. Proc Natl Acad Sci U S A. Dec. 1972;69(12):3561-6. doi: 10.1073/pnas.69.12.3561.

Motea et al., Terminal deoxynucleotidyl transferase: the story of a misguided DNA polymerase. Biochim Biophys Acta. May 2010;1804(5):1151-66. doi: 10.1016/j.bbapap.2009.06.030. Epub Jul. 29, 2009.

Nichols et al., RNA ligases. Curr Protoc Mol Biol. Oct. 2008;Chapter 3:Unit3.15. doi: 10.1002/0471142727.mb0315s84.

Pavelka et al., A new technology for the synthesis of long DNA strings. Int J Nano Med & Eng. 2017;2(7):127-130. doi: 10.25141/2474-8811-2017-7.0127.

Ponferrada-Marín et al., ROS1 5-methylcytosine DNA glycosylase is a slow-turnover catalyst that initiates DNA demethylation in a distributive fashion. Nucleic Acids Res. Jul. 2009;37(13):4264-74. doi: 10.1093/nar/gkp390. Epub May 13, 2009.

Ramadan et al., De novo DNA synthesis by human DNA polymerase λ, DNA polymerase μ and terminal deoxyribonucleotidyl transferase. J Mol Biol. May 28, 2004;339(2):395-404. doi: 10.1016/j.jmb.2004.03.056.

Roy et al., Synthesis of DNA/RNA and their analogs via phosphoramidite and H-phosphonate chemistries. Molecules. Nov. 18, 2013;18(11):14268-84. doi: 10.3390/molecules181114268.

Soni et al., Synchronous optical and electrical detection of biomolecules traversing through solid-state nanopores. Rev Sci Instrum. Jan. 2010;81(1):014301. doi: 10.1063/1.3277116.

Stoddart et al., Multiple base-recognition sites in a biological nanopore: two heads are better than one. Angew Chem Int Ed Engl. 2010;49(3):556-9. doi: 10.1002/anie.200905483.

Stoddart et al., Nucleobase recognition in ssDNA at the central constriction of the alpha-hemolysin pore. Nano Lett. Sep. 8, 2010;10(9):3633-7. doi: 10.1021/nl101955a.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

Stranges et al., Design and characterization of a nanopore-coupled polymerase for single-molecule DNA sequencing by synthesis on an electrode array. Proc Natl Acad Sci U S A. Nov. 1, 2016;113(44):E6749-E6756. doi: 10.1073/pnas.1608271113. Epub Oct. 11, 2016.

International Search Report and Written Opinion for Application No. PCT/GB2019/050296, mailed Apr. 15, 2019.

Biswas et al., Click Addition of a DNA Thread to the N-termini of Peptides for Their Translocation through Solid-State Nanopores. ACS Nano. Oct. 27, 2015; 9(10): 9652-9664. EPub Sep. 16, 2015. doi: 10.1021/acsnano.5b04984. Author Manuscript.

Carson et al., Challenges in DNA motion control and sequence readout using nanopore devices. Nanotechnology. Feb. 20, 2015;26(7):074004. doi: 10.1088/0957-4484/26/7/074004. Epub Feb. 2, 2015.

Feng et al., Nanopore-based fourth-generation DNA sequencing technology. Genomics Proteomics Bioinformatics. Feb. 2015;13(1):4-16. doi: 10.1016/j.gpb.2015.01.009. Epub Mar. 2, 2015. Erratum in: Genomics Proteomics Bioinformatics. Dec. 2015;13(6):383. Erratum in: Genomics Proteomics Bioinformatics. Jun. 2015;13(3):200-201. Erratum in: Genomics Proteomics Bioinformatics. Dec. 2015;13(6):383.

Kosuri et al., Large-scale de novo DNA synthesis: technologies and applications. Nat Methods. May 2014;11(5):499-507. doi: 10.1038/nmeth.2918.

Korlach et al., Long, processive enzymatic DNA synthesis using 100% dye-labeled terminal phosphate-linked nucleotides. Nucleosides Nucleotides Nucleic Acids. Sep. 2008;27(9):1072-83. doi: 10.1080/15257770802260741.

Sun et al., Synthesis of Fluorescent Metal Nanoclusters and Their Biomedical Applications. Journal of Instrumental Analysis. Oct. 2018;37(10):1119-1129.

* cited by examiner

Scaffold mediated synthesis

Fig. 6
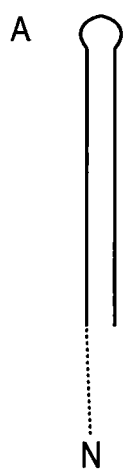
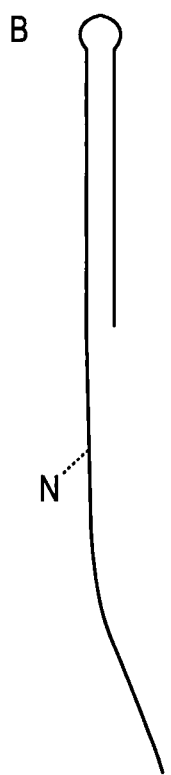

POLYNUCLEOTIDE SYNTHESIS METHOD, KIT AND SYSTEM

RELATED APPLICATIONS

This Application is a national stage filing under 35 U.S.C. 371 of International application number PCT/GB2019/050296, filed Feb. 4, 2019, which claims the benefit of United Kingdom application number 1801768.1, filed Feb. 2, 2018, each of which is incorporated by reference in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jul. 30, 2020, is named O036670100US00-SEQ-KZM and is 5,360 bytes in size.

FIELD OF THE INVENTION

The invention relates to new methods for synthesising a polymer, particularly a polynucleotide molecule, having a pre-defined sequence of units such as nucleotides. For synthesising a polynucleotide molecule the methods involve a process of extending a polynucleotide synthesis molecule with a transfer nucleotide. The methods additionally involve repeating the extension process multiple times to iteratively extend the polynucleotide molecule with multiple transfer nucleotides to generate a new polynucleotide molecule having a pre-defined nucleotide sequence. The invention also relates to methods of joining multiple synthetic polynucleotides following synthesis to form larger synthetic polynucleotides, as well as devices and systems for performing the extension, synthesis and assembly methods of the invention.

BACKGROUND TO THE INVENTION

Two primary methods exist for the synthesis and assembly of polynucleotide molecules, particularly DNA.

Phosphoramidite chemistry is a synthetic approach that assembles monomers of chemically activated T, C, A or G into oligonucleotides of approximately 100/150 bases in length via a stepwise process. The chemical reaction steps are highly sensitive and the conditions alternate between fully anhydrous (complete absence of water), aqueous oxidative and acidic (Roy and Caruthers, Molecules, 2013, 18, 14268-14284). If the reagents from the previous reaction step have not been completely removed this will be detrimental to future steps of synthesis. Accordingly this synthesis method is limited to the production of polynucleotides of length of approximately 100 nucleotides.

The Polymerase Synthetic approach uses a polymerase to synthesise a complementary strand to a DNA template using T, C, A and G triphosphates. The reaction conditions are aqueous and mild and this approach can be used to synthesise DNA polynucleotides which are many thousands of bases in length. The main disadvantage of this method is that single- and double-stranded DNA cannot be synthesised de novo by this method, it requires a DNA template from which a copy is made. (Kosuri and Church, Nature Methods, 2014, 11, 499-507).

Thus previous methods cannot be used to synthesise double-stranded DNA de novo without the aid of a pre-existing template molecule which is copied.

The inventors have developed new methodologies by which single- and double-stranded polynucleotide molecules can be synthesised de novo in a stepwise manner without the need to copy a pre-existing template molecule. The methods provide for the controlled delivery of nucleotide molecules for incorporation into a polynucleotide strand. No wash cycles or blocking chemistries are required. Such methods also avoid the extreme conditions associated with phosphoramidite chemistry techniques and in contrast are carried out under mild, aqueous conditions around neutral pH. Such methods also enable de novo synthesis of single- or double-stranded polynucleotide molecules with a potential $10^8$ improvement on current synthesis methods with nucleotide lengths of ->100mers to full genomes, providing a wide range of possibly applications in synthetic biology.

SUMMARY OF THE INVENTION

In one aspect the invention provides a method of extending a polynucleotide synthesis molecule with a transfer nucleotide, the method comprising an extension process comprising moving the transfer nucleotide through the channel of a nanopore disposed in a substrate from the cis side to the trans side of the substrate, and contacting the transfer nucleotide with an enzyme provided on the trans side of the substrate adjacent the nanopore whereupon the enzyme catalyses the transfer of the transfer nucleotide to the polynucleotide synthesis molecule thereby extending the polynucleotide synthesis molecule.

In any of the methods of extending a polynucleotide synthesis molecule with a transfer nucleotide described and defined herein, a transfer nucleotide may be an unblocked nucleotide.

The transfer nucleotide may be attached to a feeder molecule and wherein the transfer nucleotide is cleaved from the feeder molecule prior to incorporation into the polynucleotide synthesis molecule. The transfer nucleotide may be cleaved by the enzyme prior to incorporation into the polynucleotide synthesis molecule. The transfer nucleotide may be photocleaved prior to incorporation into the polynucleotide synthesis molecule.

In one embodiment a method of extending a polynucleotide synthesis molecule with a transfer nucleotide according to the invention preferably comprises an extension process comprising:

A. providing a substrate comprising a nanopore, wherein the nanopore comprises a channel allowing fluid flow from the cis side to the trans side of the substrate; providing a feeder molecule at the cis side of the substrate, the feeder molecule having an attached transfer nucleotide; providing an enzyme and the polynucleotide synthesis molecule in proximity to each other on the trans side of the substrate adjacent the nanopore; and B. moving the feeder molecule through the nanopore to bring the attached transfer nucleotide into contact with the enzyme whereupon the enzyme catalyses the transfer of the transfer nucleotide to the polynucleotide synthesis molecule thereby extending the polynucleotide synthesis molecule.

Such a method defined above may further comprise:
- C. moving the feeder molecule through the nanopore to the cis or trans side of the substrate following transfer of the transfer nucleotide to the polynucleotide synthesis molecule.

In another embodiment a method of extending a polynucleotide synthesis molecule with a transfer nucleotide according to the invention may comprise an extension process comprising:
- A. providing a substrate comprising a nanopore, wherein the nanopore comprises a channel allowing fluid flow from the cis side to the trans side of the substrate; providing a transfer nucleotide at the cis side of the substrate; providing an enzyme and the polynucleotide synthesis molecule in proximity to each other on the trans side of the substrate adjacent the nanopore; and
- B. moving the transfer nucleotide through the nanopore to bring the transfer nucleotide into contact with the enzyme whereupon the enzyme catalyses the addition of the transfer nucleotide to the polynucleotide synthesis molecule thereby extending the polynucleotide synthesis molecule.

The cis side of the substrate may comprise a mixture of transfer nucleotides in the same reaction volume, wherein the mixture comprises populations of different transfer nucleotides.

A first verification process may be performed to determine the identity and/or integrity of the transfer nucleotide, wherein:
- a) if the transfer nucleotide is determined to be the desired transfer nucleotide, moving the transfer nucleotide to bring the transfer nucleotide into contact with the enzyme; or
- b) if the transfer nucleotide is determined not to be the desired transfer nucleotide:
  - i. moving the transfer nucleotide to the cis or trans side of the substrate;
  - ii. moving a transfer nucleotide from the mixture of transfer nucleotides at the cis side of the substrate into the nanopore towards the trans side; and
  - iii. repeating the first verification process until the transfer nucleotide is determined to be the desired transfer nucleotide, following which the transfer nucleotide is moved to bring the transfer nucleotide into contact with the enzyme.

In any of the polynucleotide extension methods described and defined herein, the polynucleotide synthesis molecule may be provided having a proximal terminus adjacent the enzyme and a distal terminus, wherein the enzyme catalyses the addition of the transfer nucleotide to the proximal terminus of the polynucleotide synthesis molecule.

In any of the polynucleotide extension methods described and defined herein involving feeder molecules, feeder molecules may be provided at the cis side of the substrate having differing attached transfer nucleotides.

In any of the polynucleotide extension methods described and defined herein involving feeder molecules, the cis side of the substrate may comprise a mixture of feeder molecules in the same reaction volume, wherein the mixture comprises different populations of feeder molecules, wherein each feeder molecule of a population has the same transfer nucleotide attached, and wherein the different populations of feeder molecule have different transfer nucleotides attached. In any such method feeder molecules having differing attached transfer nucleotides may be distinguishable. For example, a feeder molecule may be capable of providing an identifiable signal to uniquely identify the attached transfer nucleotide and/or to determine the integrity of the attached transfer nucleotide.

In any of the polynucleotide extension methods described and defined herein involving feeder molecules, the extension process may comprise performing a first verification process to determine the identity and/or integrity of the transfer nucleotide of the feeder molecule, wherein:
- a) if the feeder molecule is determined to have the desired transfer nucleotide attached, moving the feeder molecule to bring the transfer nucleotide into contact with the enzyme; or
- b) if the feeder molecule is determined not to have the desired transfer nucleotide attached:
  - i. moving the feeder molecule back to the cis side of the substrate;
  - ii. moving a feeder molecule from the mixture of feeder molecules at the cis side of the substrate into the nanopore towards the trans side; and
  - iii. repeating the first verification process until the feeder molecule is determined to have the desired transfer nucleotide attached, following which the feeder molecule is moved to bring the transfer nucleotide into contact with the enzyme.

In any such method the first verification process may be performed whilst the feeder molecule is at least partially within the channel of the nanopore.

In another embodiment, the cis side of the substrate may comprise a mixture of transfer nucleotides in the same reaction volume, wherein the mixture comprises populations of different transfer nucleotides which are not attached to feeder molecules. Such a method may comprise performing a first verification process to determine the identity and/or integrity of the transfer nucleotide, wherein:
- a) if the transfer nucleotide is determined to be the desired transfer nucleotide, moving the transfer nucleotide to bring the transfer nucleotide into contact with the enzyme; or
- b) if the transfer nucleotide is determined not to be the desired transfer nucleotide:
  - i. moving the transfer nucleotide to the cis or trans side of the substrate;
  - ii. moving a transfer nucleotide from the mixture of transfer nucleotides at the cis side of the substrate into the nanopore towards the trans side; and
  - iii. repeating the first verification process until the transfer nucleotide is determined to be the desired transfer nucleotide, following which the transfer nucleotide is moved to bring the transfer nucleotide into contact with the enzyme.

In any of the polynucleotide extension methods described and defined herein involving feeder molecules, a feeder molecule may be capable of providing a different identifiable signal when the transfer nucleotide is no longer attached to the feeder molecule. The first verification process may be performed whilst the feeder molecule is at least partially within the channel of the nanopore. A feeder molecule may be capable of providing a different identifiable signal when the transfer nucleotide is no longer attached to the feeder molecule.

In any of the polynucleotide extension methods described and defined herein involving feeder molecules, step (C) may be performed only following a second verification process performed to verify that the enzyme has catalysed the transfer of the transfer nucleotide from the feeder molecule to the polynucleotide synthesis molecule, wherein the second verification process comprises:

I. moving the feeder molecule through the nanopore in the cis direction, and determining the presence or absence of the nucleobase of the transfer nucleotide;

II. moving the feeder molecule back in the trans direction to bring the nucleotide into contact with the enzyme if the nucleobase of the transfer nucleotide is determined to be attached to the feeder molecule; and III. repeating steps (I) and (II) until the desired transfer nucleotide is determined to have been removed from the feeder molecule.

In any of the polynucleotide extension methods described and defined herein, the identity and/or integrity of the nucleobase and/or the presence or absence of the transfer nucleotide attached to the feeder molecule may be determined by measurement of the feeder molecule. The identity and/or integrity of the nucleobase of the transfer nucleotide may be determined by measurement of the transfer nucleotide. Measurement of the feeder molecule or the transfer nucleotide may be with respect to the nanopore. Preferably, the feeder molecule or the transfer nucleotide is measured by measuring ion current flow through the nanopore under the action of a potential difference applied across the substrate. In any such method a change in the ion current flowing through the nanopore is dependent upon the presence and/or structure of the nucleobase of the nucleotide and thereby provides the identifiable signal to uniquely identify the transfer nucleotide and/or to determine the absence, presence and/or integrity of the transfer nucleotide. Alternatively, and/or in addition, in any such methods involving feeder molecules, changes in the ion current flowing through the nanopore may be dependent upon the presence of a pre-defined sequence of nucleobases integral to the feeder molecule (barcode) and which thereby provides the identifiable signal to uniquely identify the transfer nucleotide. In any such methods involving measuring ion current flow through the nanopore, measuring preferably comprises measuring a change in the magnitude of the ion current flowing through the nanopore.

In any of the polynucleotide extension methods described and defined herein, the identity and/or structure of the transfer nucleotide may be pre-defined.

In any of the polynucleotide extension methods described and defined herein, the nanopore may be a biological nanopore, such as a protein nanopore; a synthetic nanopore, such as a DNA origami nanopore; a solid state nanopore, such as an aperture provided in a solid state substrate; or a hybrid nanopore comprising a biological or synthetic nanopore disposed within a solid state substrate.

In any of the polynucleotide extension methods described and defined herein, the nanopore may have an internal width of between about 0.5 to >about 10 nm, preferably 0.5 to 3 nm.

In any of the polynucleotide extension methods described and defined herein, the nanopore may be a biological nanopore and may comprises Cytolysin A (ClyA) or Phi29 portal protein. The nanopore may comprise Curli production assembly/transport component (CsgG), alpha-Hemolysin, *Mycobacterium smegmatis* porin A (MspA), Lysenin, aerolysin, cytotoxin K (cytk) or actinoporin fragaceatoxin C (FraC).

In any of the polynucleotide extension methods described and defined herein, the enzyme may be provided free in solution on the trans side of the substrate adjacent the nanopore.

In any of the polynucleotide extension methods described and defined herein, the enzyme may be attached to the nanopore; optionally by genetic fusion such that the nanopore and enzyme are a fusion protein, by one or more covalent bonds, by one or more linkers, or by an affinity interaction or by any combination of attachment methods.

In any of the polynucleotide extension methods described and defined herein, the polynucleotide synthesis molecule may be provided having a proximal terminus tethered to the enzyme.

In any of the polynucleotide extension methods described and defined herein, the polynucleotide synthesis molecule may comprise DNA or RNA, i.e. may be extended to form a polynucleotide molecule comprising DNA or RNA.

In any of the polynucleotide extension methods described and defined herein, the polynucleotide synthesis molecule may be hybridised to a polynucleotide scaffold molecule to form a double stranded polynucleotide molecule. In any such methods the scaffold molecule may be a circular polynucleotide molecule. In any such methods the scaffold molecule may be tethered to the enzyme; optionally wherein the polynucleotide synthesis molecule is tethered to the enzyme indirectly via hybridisation to the scaffold molecule. In any such methods the scaffold polynucleotide molecule may comprises a sequence comprising one or more universal nucleobases, such as inosine; optionally wherein the scaffold polynucleotide molecule comprises polyinosine sequences.

In any of the polynucleotide extension methods described and defined herein, the enzyme may be a DNA-directed DNA polymerase. The polynucleotide synthesis molecule may be extended to form a polynucleotide molecule comprising DNA or RNA, preferably DNA. In any such methods, the DNA-directed DNA polymerase may lack 3' to 5' exonuclease activity and/or may lack 5' to 3' exonuclease activity and/or may possesses strand displacement activity.

In any of the polynucleotide extension methods described and defined herein, the transfer nucleotide may be provided as a molecule comprising a nucleobase, a ribose sugar and three or more phosphate groups.

In any of the polynucleotide extension methods described and defined herein, the nucleotide may be a deoxynucleotide triphosphate (dNTP), such as dATP, dTTP, dCTP or dGTP, or a modified dNTP such as a modified dATP, a modified dTTP, a modified dCTP and/or a modified dGTP.

In any of the polynucleotide extension methods described and defined herein, the enzyme may be a DNA-directed RNA polymerase, and wherein the polynucleotide synthesis molecule may be extended to form a polynucleotide molecule comprising RNA or DNA, preferably RNA. In any of the polynucleotide extension methods described and defined herein, the polynucleotide extension nucleotide may be a nucleotide triphosphate (NTP), such as ATP, TTP, CTP or GTP, or a modified NTP, such as a modified ATP, a modified TTP, a modified CTP and/or a modified GTP.

In another embodiment, in the polynucleotide extension methods described and defined herein, the polynucleotide synthesis molecule may be a single stranded polynucleotide molecule. In such a method the enzyme has template-independent enzyme activity, such as template-independent polymerase or transferase activity. The enzyme may have a terminal transferase activity, e.g. wherein the enzyme is terminal nucleotidyl transferase, pol lambda, pol μ or Φ29 DNA polymerase, and the polynucleotide synthesis molecule is extended to form a polynucleotide molecule comprising DNA or RNA, preferably DNA. In such a method the enzyme may be a terminal deoxynucleotidyl transferase and wherein the polynucleotide synthesis molecule is extended to form a polynucleotide molecule comprising DNA or RNA, preferably DNA.

In any of the polynucleotide extension methods described and defined herein, the enzyme may be provided having the capability of incorporating modified or non-natural nucleobases.

In any of the polynucleotide extension methods described and defined herein, the feeder molecule may comprise a molecule comprising DNA, RNA, peptide nucleic acid (PNA), locked nucleic acid (LNA), unlocked nucleic acid (UNA), bridged nucleic acid (BNA), glycerol nucleic acid (GNA), threose nucleic acid (TNA), morpholino, phosphorothioate nucleic acid, methylphosphonate nucleic acid, peptide, oligopeptide, polypeptide, polymer or any combination thereof.

In any of the polynucleotide extension methods described and defined herein, the enzyme may catalyse the extension of the polynucleotide synthesis molecule at the 3' end of the polynucleotide synthesis molecule.

In any of the polynucleotide extension methods described and defined herein, the nucleotide may be attached to the feeder molecule at a terminal end of the feeder molecule, or at a position along the length of the feeder molecule.

In any of the polynucleotide extension methods described and defined herein, the feeder molecule may comprise a negatively charged leader molecule, e.g. comprising one or more C3 spacers.

In any of the polynucleotide extension methods described and defined herein, a transfer nucleotide may be attached to a feeder molecule via a linker. In any such method the linker may comprise a phosphate group linker comprising one phosphate group, or a polyphosphate group linker comprising two, three or more phosphate groups. The linker may comprise a hydrocarbon chain, e.g. comprising from 2 to 20 or more carbon atoms, optionally comprising an alkylene group e.g. a C2-20 alkylene group. The linker may have the following structure:

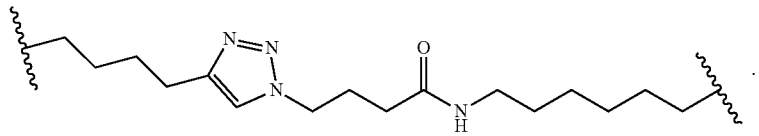 [SMILES: *CCCCCCNC(=O)CCCn1cc(CCCC*)nn1]

The linker may comprise a polymer, e.g. a polyether polymer such as polyethylene glycol (PEG).

In any of the polynucleotide extension methods described and defined herein, the feeder molecule may comprise a sequence of nucleotides (barcode) capable of uniquely identifying a feeder molecule and the type of transfer nucleotide attached thereto.

In any of the polynucleotide extension methods described and defined herein involving feeder molecules, the feeder molecule may comprise one or more blocking moieties, wherein a blocking moiety is provided at a position on the feeder molecule so that when the feeder molecule is moved into a nanopore to a position of interest in the nanopore, the blocking moiety acts to inhibit further translocation of the feeder molecule in the trans direction, optionally wherein one or more blocking moieties comprises a reversible blocking moiety. In any such method, the one or more blocking moieties may be provided along the length of the feeder molecule and/or may be provided at a terminal end of the feeder molecule and/or may be provided as an integral part of the feeder molecule. In any such method, a blocking moiety may be a molecule attached to the feeder molecule, optionally wherein a blocking moiety is a peptide, oligopeptide, polypeptide, protein or other polymer. In any such method, the blocking moiety may be attached to the feeder molecule by one or more covalent bonds, by an affinity interaction or by one or more linkers. A blocking moiety may be a protein comprising streptavidin or horseradish peroxidase (HP). A blocking moiety may comprise a portion of the feeder molecule, e.g. a blocking moiety may comprise a portion of secondary or tertiary structure formed within the feeder molecule. The portion of secondary structure may comprise a double stranded region of the feeder molecule, a region of nucleic acid double helix, a region of nucleic acid stem-loop structure (hairpin), a nucleic acid cruciform or pseudoknot structure, a looped region of unpaired nucleotides, a nucleic acid bulge region, a quadruplex region, a region of cross-linked nucleic acid, or any combination thereof.

In any of the polynucleotide extension methods described and defined herein, a blocking moiety may be attached to, or form part of, a transfer nucleotide, for example when the transfer nucleotide comprises multiple nucleotides. In any such method, a blocking moiety may be structured in any of the same ways and may function in any of the same ways as described and defined herein with respect to a blocking moiety attached to a feeder molecule.

In any of the polynucleotide extension methods described and defined herein involving feeder molecules, a feeder molecule may further comprise one or more feeder molecule tethering moieties; wherein a feeder molecule tethering moiety reversibly tethers a feeder molecule to the substrate prior to capture of the feeder molecule and its translocation into the nanopore. A feeder molecule tethering moiety may comprise a hydrophobic molecule. A feeder molecule tethering moiety may comprise a lipid molecule, optionally a sterol molecule such as cholesterol.

In any of the polynucleotide extension methods described and defined herein involving one or more blocking moieties, the method may comprise moving the feeder molecule in the nanopore in the trans direction to a first position of interest in the nanopore whereupon the blocking moiety acts to inhibit further translocation of the feeder molecule; and further comprising moving the feeder molecule in the nanopore in the trans direction to one or more second positions of interest in the nanopore upon removal of the blocking moiety, or upon an alteration in the conformation of the blocking moiety and/or upon an alteration in the conformation of the feeder molecule. Any such method may further comprise moving the feeder molecule back through the nanopore in the cis direction to the first position of interest or to a third position of interest upon reattachment of a blocking moiety, or upon alteration in the conformation of a blocking moiety and/or upon an alteration in the conformation of the feeder molecule. In any such method, the first or third position of interest may be a position in the nanopore which is insufficient to allow the transfer nucleotide to contact the enzyme, and wherein at least one of the second positions of interest is a position in the nanopore which is sufficient to allow the transfer nucleotide to contact the enzyme. In one example of such a method, the feeder molecule may comprise a nucleic acid provided with at least one reversible blocking moiety comprising a double stranded region of the feeder molecule, the method further comprising moving the feeder molecule in the nanopore to the first position of interest whereupon the double stranded region acts to inhibit further translocation of the feeder molecule in the trans direction; and wherein the feeder molecule is subjected to conditions which cause the strands of the double stranded region to separate within the region, or within at least a portion of the region, whereupon the feeder molecule further translocates to a second position of interest.

In any polynucleotide extension method described and defined herein involving feeder molecules and a first verification process, the first verification process may be performed when the feeder molecule is moved in the nanopore to the first position of interest. In any such method, when the feeder molecule is at a second position of interest the feeder molecule may be subjected to conditions which cause the strands of the double stranded region to reanneal within the region, or within at least a portion of the region, whereupon the feeder molecule is moved back in the nanopore in the cis direction to the first or third position of interest. In any such method, the second verification process may be performed when the feeder molecule is moved back in the cis direction to the first or third position of interest in the nanopore.

In any of the polynucleotide extension methods described and defined herein involving feeder molecules, the method may preferably comprise moving the feeder molecule in the nanopore by applying a potential difference across the substrate, preferably wherein the potential difference is voltage (V). In any such method, the steps of moving a feeder molecule into a nanopore in the direction of the trans side of the substrate, moving a feeder molecule in the trans direction to a first position of interest and moving a feeder molecule in the trans direction to a second position of interest are controlled by varying potential differences, preferably varying voltages, applied across the substrate. In any such method, the steps of moving a feeder molecule back in the cis direction from a second position of interest to a first or third position of interest and the step of moving the feeder molecule out of the nanopore and back to the cis side of the substrate are controlled by varying potential differences, preferably varying voltages, applied across the substrate.

In any of the polynucleotide extension methods described and defined herein, the action of a reversible blocking moiety may be controlled by the action of varying potential differences, preferably varying voltages, applied across the substrate.

In any of the polynucleotide extension methods described and defined herein, the nanopore may be coupled to a feeder molecule handling moiety which facilitates movement of the feeder molecule into and through the nanopore, and wherein the extension process comprises contacting the feeder molecule with the feeder molecule handling moiety and moving the feeder molecule into and through the nanopore. A feeder molecule handling moiety may be e.g. a polymerase, a nuclease, a helicase or a topoisomerase such as a gyrase. A feeder molecule handling moiety may be a phi29 DNA polymerase, a T7 DNA polymerase, a His 1 DNA polymerase, a His 2 DNA polymerase, a *bacillus* phage M2 DNA polymerase, a *streptococcus* phage CPI DNA polymerase, an *enterobacter* phage PRD1 DNA polymerase, or any variant or derivative thereof. In any such method, the nanopore may be coupled to a feeder molecule handling moiety by genetic fusion such that the nanopore and feeder molecule handling moiety are a fusion protein, by one or more covalent bonds, by one or more linkers, or by an affinity interaction.

In any of the polynucleotide extension methods described and defined herein, the nanopore may be coupled to one or more nanopore adaptor moieties; wherein an adaptor moiety increases the efficiency of the interaction between the nanopore and the feeder molecule compared to the efficiency in the absence of the adaptor moiety. In any such method, the nanopore adaptor moiety may be a cyclic molecule, optionally wherein the adaptor is heptameric or hexameric. The nanopore adaptor moiety may be for example a cyclodextrin or a derivative thereof, optionally selected from the group consisting of γ-cyclodextrin (γ-CD), β-cyclodextrin (β-CD), 6-monodeoxy-6-monoamino-β-cyclodextrin (am$_1$β-CD), heptakis-6-amino-β-cyclodextrin (am$_7$-β-CD), heptakis-(6-deoxy-6-guanidino)-cyclodextrin (gu$_7$-β-CD), α-cyclodextrin (α-CD). In any such method, the nanopore may be coupled to a nanopore adaptor moiety by genetic fusion such that the nanopore and nanopore adaptor moiety are a fusion protein, by one or more covalent bonds, by one or more linkers, or by an affinity interaction.

In any of the polynucleotide extension methods described and defined herein, the substrate may comprise a membrane comprised of amphiphilic molecules.

In any of the polynucleotide extension methods described and defined herein, the substrate may comprise a membrane comprised of amphiphilic molecules comprising a block copolymer.

In any of the polynucleotide extension methods described and defined herein, the substrate may comprise a solid state substrate. The nanopore may comprise an aperture formed in a solid state substrate.

In any of the polynucleotide extension methods described and defined herein, the nanopore may be a hybrid nanopore comprising a biological or synthetic nanopore disposed in a solid state substrate, or disposed in an aperture formed in a solid state substrate, preferably wherein the nanopore is any biological or synthetic nanopore, e.g. as described or defined herein.

In any of the polynucleotide extension methods described and defined herein, the extension process may be a first extension process and wherein the method further comprises repeating the extension process one or more times to further extend the polynucleotide synthesis molecule with one or more further transfer nucleotides.

In any of the polynucleotide extension methods described and defined herein, the extension process may further comprise a step of synthesising a complementary polynucleotide molecule using the polynucleotide synthesis molecule as a template, thereby forming a double stranded polynucleotide molecule comprising the polynucleotide synthesis molecule hybridised to the complementary polynucleotide molecule.

In any of the polynucleotide extension methods described and defined herein, the extension process may further comprise a step of amplifying the synthesised double stranded polynucleotide molecule, preferably by polymerase chain reaction (PCR).

In any of the polynucleotide extension methods described and defined herein, the method may further comprise a step of ligating a double stranded polynucleotide molecule with another double stranded polynucleotide molecule, optionally synthesised using a different nanopore, optionally wherein the ligation step is performed after a step of amplifying one or more of the synthesised double stranded polynucleotide molecules. In any of the polynucleotide extension methods described and defined herein, the method may further comprise a step of ligating a single stranded polynucleotide molecule with another single stranded polynucleotide molecule, optionally synthesised using a different nanopore, optionally wherein the ligation step is performed after a step of amplifying one or more of the synthesised single stranded polynucleotide molecules.

In any of the polynucleotide extension methods described and defined herein, a nanopore may be positioned within a reaction chamber of a system, wherein the system comprises an array of nanopores, wherein the substrate separates the reaction chamber into a cis reaction chamber portion and a trans reaction chamber portion, wherein each nanopore provides a channel through the substrate from the cis to the trans reaction chamber portion. In any such method the trans reaction chamber portion may comprise an array of trans chambers that are fluidically isolated from each other, wherein each trans chamber is separated from the cis chamber by a substrate comprising the nanopore; wherein polynucleotide synthesis molecules of different sequence may be synthesised in different trans reaction chambers, and wherein the potential difference applied across each trans reaction chamber and the cis chamber may be independently controlled. In any of these methods, the cis reaction chamber portion may be a single chamber and may be common to each of the separate trans reaction chamber portions. In any of these methods, cis reaction chamber portions and/or trans reaction chamber portions may be droplets, optionally comprising water-in-oil droplets. The droplets may be components of an electrowetting-on-dielectric system (EWOD) or may be components of a microfluidic system. In any of these methods, a feeder molecule may be provided to a nanopore via a feeder molecule delivery channel, such as a tube e.g. a carbon nanotube.

In any of the polynucleotide extension methods described and defined herein, a nanopore may be coupled to an electronic device comprising tunnelling electrodes, a field effect transistor (FET) device or a complementary-metal-oxide-semiconductor (CMOS) device.

Any of the polynucleotide extension methods described and defined herein are preferably in vitro methods.

In another aspect the invention provides a polynucleotide synthesis system for carrying out any of the synthesis methods described and defined herein, the system comprising:

(a) an array of reaction chambers each comprising a nanopore, wherein reaction chambers are fluidically isolated from each other; and wherein each reaction chamber comprises a substrate comprising a nanopore and wherein the substrate separates the reaction chamber into a cis reaction chamber portion and a trans reaction chamber portion, wherein cis and trans reaction chamber portions are in fluidic communication with each other via a channel in the nanopore; wherein each reaction chamber further comprises an enzyme and a polynucleotide synthesis molecule in proximity to each other on the trans side of the substrate adjacent the nanopore;

(b) means for the delivery of transfer nucleotides, optionally attached to feeder molecules, into cis reaction chamber portions, optionally wherein each cis reaction chamber portion further comprises one or more delivery channels configured to deliver transfer nucleotides to the nanopore;

(c) means for the provision of a voltage across the substrate of each reaction chamber; preferably electrodes, and wherein the substrate is disposed between an anode and a cathode; and (d) means for the detection of ion current flowing through the nanopore of each reaction chamber, preferably electrodes applied to the nanopore or adjacent thereto.

In any such system, cis reaction chamber portions and/or trans reaction chamber portions may be droplets, optionally comprising water-in-oil droplets, e.g. wherein the substrate comprises an interface between different droplets and wherein the nanopore is disposed within the substrate allowing communication between droplets. In any such system, droplets may be components of an electrowetting-on-dielectric system (EWOD) or a microfluidic system.

In another aspect the invention provides a kit for use with any of the systems described and defined herein and for carrying out any of the extension methods described and defined herein, the kit comprising volumes of reaction reagents comprising transfer nucleotides, optionally attached to feeder molecules, the kit optionally further comprising reagents for assembling reaction units comprising a nanopore disposed in a substrate, optionally an enzyme and optionally polynucleotide synthesis molecules, the kit further optionally comprising an array comprising reaction chambers for the assembly of reaction units.

BRIEF DESCRIPTION OF THE FIGURES

FIG. 6 shows a transfer nucleotide attached to a feeder molecule via a linker.

DETAILED DESCRIPTION OF THE INVENTION

The invention relates to new methods for synthesising a polynucleotide molecule having a pre-defined nucleotide sequence. The methods involve a process of extending a polynucleotide synthesis molecule with a transfer nucleotide. The methods additionally involve repeating the extension process multiple times to iteratively extend the polynucleotide synthesis molecule with multiple transfer nucleotides to generate a new polynucleotide molecule having a pre-defined nucleotide sequence.

Figure 1:
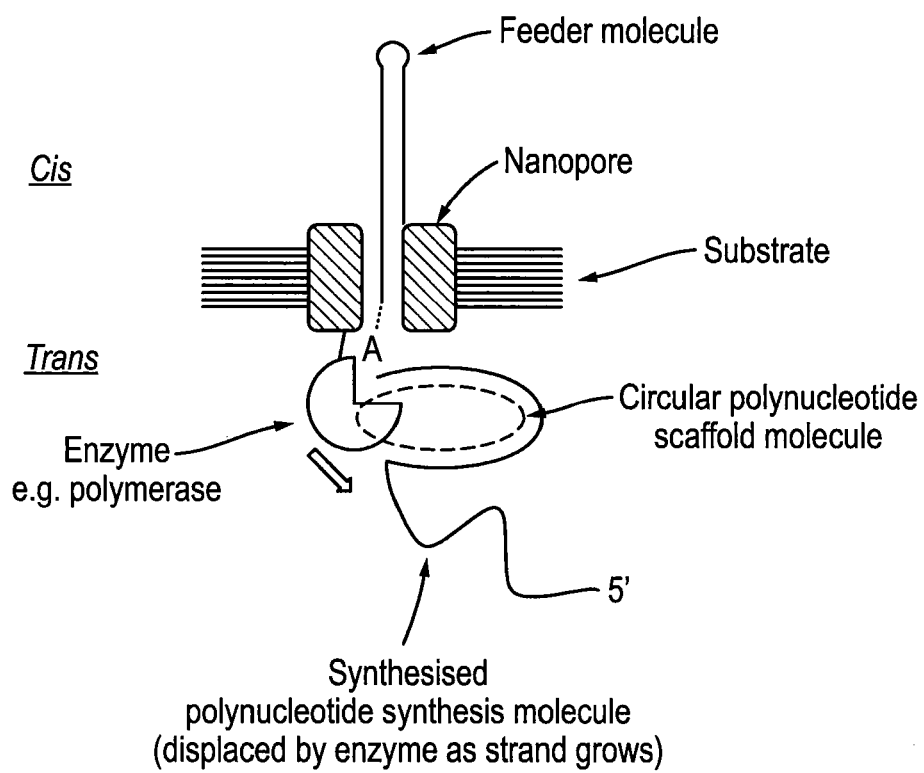
FIG. 1 shows a simplified example overview illustrating features of the method of the invention.

A simplified non-limiting exemplary overview illustrating one way of implementing a method of the invention is set out in FIG. 1. A feeder molecule is provided having an attached transfer nucleotide. The feeder molecule is moved through a nanopore placed in a substrate, from a cis side of the substrate to a trans side of the substrate. The transfer nucleotide is initially provided on the cis side of the substrate. The nucleotide is then moved to the trans side of the substrate and contacted with an enzyme, such as a polymerase, ligase or terminal transferase, provided on the trans side of the substrate, whereupon the enzyme catalyses the transfer of the nucleotide to a polynucleotide synthesis molecule to complete an extension process. Cycles of extension processes may be performed to create a synthetic polynucleotide molecule.

The use of feeder molecules to facilitate movement of nucleotides in a nanopore is preferred. However, nucleotides may be controllably moved through a nanopore without the requirement of being attached to a feeder molecule, as described further herein.

The invention also relates to methods of assembling synthetic polynucleotides following synthesis by the methods of the invention, as well as devices and systems for performing the extension, synthesis and assembly methods of the invention.

In the methods of the invention, the extension processes do not require the copying of a pre-existing template polynucleotide molecule. The invention also relates to methods of storing data. In one aspect the invention relates to methods of storing data in digital form in a polynucleotide molecule by generating nucleotide sequences indicative of the "0" and "1" states of a bit of digital information. By repeating such methods it is possible to generate multiple bits of information in the polynucleotide molecule. Alternatively, due to the ability to incorporate at least four different bases in a polynucleotide molecule, digital information may be encoded using systems other than binary, for example, base-3 or base-4.

In addition, in the methods of the invention the extension processes do not require the addition of a transfer nucleotide comprising a blocking group, protecting group or reversible terminator group. No de-protecting steps are necessary before the next transfer nucleotide is incorporated. Thus in any of the synthesis methods described and defined herein, the transfer nucleotide may be an unblocked nucleotide, wherein the nucleotide does not comprise a protecting group, reversible terminator group, or any other function which may inhibit further extension by an enzyme such as polymerase, ligase or terminal transferase.

In addition to the lack of a requirement for a template, the invention provides several further advantages compared to current methods for polynucleotide synthesis. For example, there is no requirement to separate nucleotides into groups of the same species. Different nucleotides can be provided as a heterogenous mixture and the desired nucleotide can be selected prior to incorporation. Thus a single reaction volume may be provided to accommodate all reagents required for synthesis. Washing steps or steps for the exchange of reagents are not necessary. Processes may be implemented to verify the integrity of nucleotides to be incorporated thus reducing the need for the initial provision of high purity samples. Damaged or missing bases can be detected and eliminated. The methods provide for the possibility of separately addressing each reaction volume comprising a nanopore on an individual basis in a multi-reaction volume system, thus providing for asynchronous control of reaction volumes such that each reaction volume may give rise to a different polynucleotide having a different sequence. The methods provide for the possibility of high speed synthesis of polynucleotide molecules, such as for example 0.1-1 nt/sec (360-3600 nt/hr). Thus the invention provides significantly simplified synthesis protocols.

Features of the invention are described in more detail herein.

Enzymes

The present invention relates to methods of extending a polynucleotide synthesis molecule with a transfer nucleotide. Throughout the entirely of this disclosure reference to extending a polynucleotide synthesis molecule with "a" transfer nucleotide, or adding "a" transfer nucleotide, in any given cycle of synthesis also embraces extending a polynucleotide synthesis molecule with two or more transfer nucleotides simultaneously in dimeric or polymeric form in the same cycle of synthesis. Similarly, the use of the word "nucleobase" in singular form also embraces two or more nucleobases simultaneously. In the methods of the invention such extension is achieved by the action of an enzyme.

The enzyme should be capable of catalysing a reaction comprising the addition of a nucleotide to a polynucleotide synthesis molecule. Typically, but not exclusively, the added nucleotide is a molecule comprising a sugar group, a phosphate group and a nucleobase. Typically, the added nucleotide is a nucleoside monophosphate. A nucleotide is further defined herein. Provided that the enzyme is capable of catalysing this reaction, any suitable enzyme may be used. Thus enzymes which may be applied to any methods of the present invention include polymerases, nucleotidyl transferases and ligases, as well as any enzyme fragment, derivative, analogue or functional equivalent thereof provided that the required nucleotide extension function is preserved in the enzyme. Directed evolution techniques, conventional screening, rational or semi-rational engineering/mutagenesis methods or any other suitable methods may be used to alter any such enzyme to provide and/or optimise the required nucleotide extension function.

Enzymes Capable of Extending Single-Stranded Polynucleotide Synthesis Molecules

In some methods of the invention the polynucleotide synthesis molecule is a single-stranded polynucleotide molecule, as described further herein.

Enzymes are available that are capable of extending a single-stranded polynucleotide synthesis molecule by the addition of a nucleotide to the synthesis molecule. This includes enzymes which have template-independent enzyme activity, such as template-independent polymerase or template-independent transferase activity or template-independent ligase activity. Any of these enzymes may be used in the methods of the invention e.g. wherein extension of a single-stranded polynucleotide synthesis molecule is required.

One such preferred enzyme is a terminal nucleotidyl transferase enzyme, such as terminal deoxynucleotidyl transferase (TdT) (see e.g. Motea et al, 2010; Minhaz Ud-Dean, Syst. Synth. Biol., 2008, 2(3-4), 67-73). TdT is capable of catalysing the addition to a polynucleotide synthesis molecule of a nucleotide molecule (nucleoside monophosphate) from a nucleoside triphosphate substrate (NTP or dNTP). TdT is capable of catalysing the addition of natural and non-natural nucleotides. It is also capable of catalysing the addition of nucleotide analogues (Motea et al, 2010). Pol lambda and pol µ enzymes may also be used (Ramadan K, et al., J. Mol. Biol., 2004, 339(2), 395-404), as may Φ29 DNA polymerase.

Techniques for the extension of a single-stranded polynucleotide molecule, both DNA and RNA, in the absence of a template by the action of a terminal transferase enzyme (e.g. terminal deoxynucleotidyl transferase; TdT) to create an artificially-synthesised single-stranded polynucleotide molecule has been extensively discussed in the art. Such techniques are disclosed in, for example, patent application publications WO2016/034807, WO 2016/128731, WO2016/139477 and WO2017/009663, as well as US2014/0363852, US2016/0046973, US2016/0108382, and US2016/0168611. These documents describe the controlled extension of a single-stranded polynucleotide synthesis molecule by the action of TdT to create an artificially-synthesised single-stranded polynucleotide molecule. Extension by natural and non-natural/artificial nucleotides using such enzymes is described, as is extension by modified nucleotides, for example, nucleotides incorporating blocking groups. Any of the terminal transferase enzymes disclosed in these documents may be applied to methods of the present invention, as well as any enzyme fragment, derivative, analogue or functional equivalent thereof provided that the terminal transferase function is preserved in the enzyme. Directed evolution techniques, conventional screening, rational or semi-rational engineering/mutagenesis methods or any other suitable methods may be used to alter any such enzyme to provide and/or optimise the required function. Any other enzyme which is capable of extending a single-stranded polynucleotide molecule, such as a molecule comprising DNA or RNA, with a transfer nucleotide without the use of a template may be used, e.g. a ligase enzyme.

Thus in any of the methods defined herein a single stranded polynucleotide synthesis molecule comprising DNA, or a single stranded portion of a polynucleotide synthesis molecule comprising DNA, may be extended by an enzyme which has template-independent enzyme activity, such as template-independent polymerase, ligase or transferase activity. The enzyme may have nucleotidyl transferase enzyme activity, e.g. a deoxynucleotidyl transferase enzyme, such as terminal deoxynucleotidyl transferase (TdT), pol lambda, pol µ, Φ29 DNA polymerase, or an enzyme fragment, derivative, analogue or functional equivalent thereof. A polynucleotide synthesis molecule extended by the action of such an enzyme comprises DNA.

In any of the methods defined herein a single stranded polynucleotide synthesis molecule comprising RNA, or a single stranded portion of a polynucleotide synthesis molecule comprising RNA, may be extended by an enzyme which has nucleotidyl transferase enzyme (e.g. including TdT, pol lambda and pol µ), or an enzyme fragment, derivative, analogue or functional equivalent thereof. A polynucleotide synthesis molecule extended by the action of such an enzyme may comprise RNA. For the synthesis of a single stranded polynucleotide synthesis molecule comprising RNA, or a single stranded portion of a polynucleotide synthesis molecule comprising RNA, any suitable nucleotidyl transferase enzyme may be used. Nucleotidyl transferase enzymes such as poly (U) polymerase and poly(A) polymerase are capable of template-independent addition of nucleoside monophosphate units to polynucleotide synthesis molecules. Any of these enzymes may be applied to methods of the present invention, as well as any enzyme fragment, derivative, analogue or functional equivalent thereof provided that the nucleotidyl transferase function is preserved in the enzyme. Directed evolution techniques, conventional screening, rational or semi-rational engineering/mutagenesis methods or any other suitable methods may be used to alter any such enzyme to provide and/or optimise the required function.

With regards to ligase enzymes, any suitable ligase enzyme or enzyme having ligase activity may be used. Template-independent ligation of single-stranded DNA by DNA ligase enzymes have been described e.g. by Georges, F. et al. (Nucleosides, Nucleotides and Nucleic Acids, 1989, 8(8): pp 1427-1440) and Kuhn, H. et al. (FEBS J. 2005, 272(23): pp 5991-6000). T4 RNA Ligase 1 (ssRNA Ligase) is capable of catalysing the ligation of single-stranded RNA as well as DNA. A range of RNA ligases are described by Nichols, N. et al. (Curr Protoc Mol Biol. 2008, Chapter 3, Unit 3.15). Thus molecules, enzymes, chemicals and methods for ligating (joining) single-stranded polynucleotides are well known to the skilled person.

Enzymes Capable of Extending Double-Stranded Polynucleotide Synthesis Molecules

In some methods of the invention the polynucleotide synthesis molecule is a component of a double-stranded polynucleotide molecule, as described further herein.

Enzymes are available that are capable of extending one strand (i.e. the polynucleotide synthesis molecule) of a double-stranded polynucleotide molecule by the addition of a nucleotide to the polynucleotide synthesis molecule of the double-stranded polynucleotide molecule, such as polymerase and ligase enzymes. Any of these enzymes may be used in the methods of the invention wherein such extension is required, as well as any enzyme fragment, derivative, analogue or functional equivalent thereof provided that the nucleotide extension function is preserved in the enzyme. Directed evolution techniques, conventional screening, rational or semi-rational engineering/mutagenesis methods or any other suitable methods may be used to alter any such enzyme to provide and/or optimise the required function.

For the extension of such a polynucleotide synthesis molecule comprising DNA, a DNA polymerase may be used. Any suitable DNA polymerase may be used.

The DNA polymerase may be for example Bst DNA polymerase full length, Bst DNA polymerase large fragment, Bsu DNA polymerase large fragment, *E. coli* DNA polymerase DNA Pol I large (Klenow) fragment, M-MuLV reverse transcriptase, phi29 DNA polymerase, *Sulfolobus* DNA polymerase IV, Taq DNA polymerase, T4 DNA polymerase, T7 DNA polymerase and enzymes having reverse transcriptase activity.

The DNA polymerase may lack 3' to 5' exonuclease activity. Any such suitable polymerase enzyme may be used. Such a DNA polymerase may be, for example, Bst DNA polymerase full length, Bst DNA polymerase large fragment, Bsu DNA polymerase large fragment, E. coli DNA polymerase DNA Pol I large (Klenow) fragment, M-MuLV reverse transcriptase, Sulfolobus DNA polymerase IV, Taq DNA polymerase.

The DNA polymerase may possess strand displacement activity. Any such suitable polymerase enzyme may be used. Such a DNA polymerase may be, for example, Bst DNA polymerase large fragment, Bsu DNA polymerase large fragment, E. coli DNA polymerase DNA Pol I large (Klenow) fragment, M-MuLV reverse transcriptase, phi29 DNA polymerase.

The DNA polymerase may lack 3' to 5' exonuclease activity and may possess strand displacement activity. Any such suitable polymerase enzyme may be used. Such a DNA polymerase may be, for example, Bst DNA polymerase large fragment, Bsu DNA polymerase large fragment, E. coli DNA polymerase DNA Pol I large (Klenow) fragment, M-MuLV reverse transcriptase.

The DNA polymerase may lack 5' to 3' exonuclease activity. Any such suitable polymerase enzyme may be used. Such a DNA polymerase may be, for example, Bst DNA polymerase large fragment, Bsu DNA polymerase large fragment, E. coli DNA polymerase DNA Pol I large (Klenow) fragment, M-MuLV reverse transcriptase, phi29 DNA polymerase, Sulfolobus DNA polymerase IV, T4 DNA polymerase, T7 DNA polymerase.

The DNA polymerase may lack both 3' to 5' and 5' to 3' exonuclease activities and may possess strand displacement activity. Any such suitable polymerase enzyme may be used. Such a DNA polymerase may be, for example, Bst DNA polymerase large fragment, Bsu DNA polymerase large fragment, E. coli DNA polymerase DNA Pol I large (Klenow) fragment, M-MuLV reverse transcriptase.

The DNA polymerase may also be a genetically engineered variant. For example, the DNA polymerase may be a genetically engineered variant. of the native DNA polymerase from Thermococcus species 9° N, such as species 9° N-7. One such example of a modified polymerase is Therminator IX DNA polymerase available from New England BioLabs. Other engineered or variant DNA polymerases include Deep Vent (exo-), Vent (Exo-), 9° N DNA polymerase, Therminator DNA polymerase, Klenow fragment (Exo-), Bst DNA polymerase, Bsu DNA polymerase, Sulfolobus DNA polymerase I, and Taq Polymerase.

For the extension of such a polynucleotide synthesis molecule comprising RNA, any suitable enzyme may be used. For example an RNA polymerase may be used. Any suitable RNA polymerase may be used.

The RNA polymerase may be T3 RNA polymerase, T7 RNA polymerase, SP6 RNA polymerase, E. coli RNA polymerase holoenzyme.

With regards to ligase enzymes, any suitable ligase enzyme or enzyme having ligase activity may be used. The ligase may be a modified ligase with enhanced activity for single-base overhang substrates. The ligase may be a T3 DNA ligase or a T4 DNA ligase. The ligase may a blunt TA ligase. For example a blunt TA ligase is available from New England BioLabs (NEB). This is a ready-to-use master mix solution of T4 DNA Ligase, ligation enhancer, and optimized reaction buffer specifically formulated to improve ligation and transformation of both blunt-end and single-base overhang substrates. Molecules, enzymes, chemicals and methods for ligating (joining) double-stranded polynucleotides are well known to the skilled person.

In any of the polynucleotide extension methods described and defined herein, the enzyme may catalyse the extension of the polynucleotide synthesis molecule at the 3' end of the polynucleotide synthesis molecule.

In addition to the above-noted examples, other enzymes which are capable of mediating the transfer of one or more nucleotides to a polynucleotide synthesis molecule in accordance with methods of the invention are available. A person skilled in the art will readily recognise any enzyme having such capability which may be used. Such enzymes include, but are not limited to, endonucleases, including Type I, Type II, and Type III restriction endonucleases, enzymes which mediate gene editing such as CRISPR, including CRISPR/Cas endonucleases such as CRISPR/Cas9, and CRISPR/Cfp endonucleases such as CRISPR/Cfp1, Transcription activator-like effector nucleases (TALEN) enzymes, Zinc-finger nucleases (ZFNs), isomerases, including topoisomerases, recombinases such as Cre recombinase, Hin recombinase, Tre recombinase, and FLP recombinase, transposase enzymes and integrase enzymes.

Attachment of Enzymes to Substrates

In the methods of the invention enzymes may be provided free in solution on the trans side of the substrate adjacent the nanopore. Such an embodiment may be achieved by providing, for example, a micro or nano-scale reaction volume in which the extension processes are performed, wherein a micro or nano-scale reaction volume comprises the enzyme(s) provided at the trans side of the substrate adjacent the nanopore. Such a micro or nano-scale reaction volume may comprise, for example, a droplet, such as a water-in-oil droplet or other micro or nano-scale chamber, such as for example wells or chambers as components of chips with dimensions of approximately about 100 µm×100 µm×100 µm.

In the methods of the invention an enzyme is preferably provided attached to the substrate on the trans side of the substrate adjacent the nanopore. By providing the enzyme attached to the substrate it is to be expected that greater control may be provided to the system.

An enzyme may be attached to the substrate directly or indirectly on the trans side of the substrate. An enzyme may be attached to the substrate on the trans side of the substrate by a linker. An enzyme may be attached to the substrate via the nanopore on the trans side, in which case the enzyme may be attached directly to the nanopore, preferably via a linker.

An enzyme may be attached to a substrate on the trans side, including directly to a nanopore, by any suitable method known in the art, provided that the attachment maintains the capability of the enzyme and nanopore to perform their respective functions as described herein. An enzyme may be attached to a substrate, including to a nanopore, by means such as protein:protein interactions, chemical interactions, co-valent attachment and genetic fusion between nanopore and enzyme. Any suitable attachment methods described herein in the section "Linkers and attachment moieties" may be applied mutatis mutandis for the purposes of attaching an enzyme to a substrate, including to a nanopore. An enzyme may be attached directly to a substrate e.g. via cysteines or click chemistry as described herein, or via unnatural bases such as azides. An enzyme may be attached directly to a substrate via polynucleotide molecules such as DNA, LNA, BNA etc. In such a situation polynucleotide molecules may be attached to both the enzyme and substrate which are then coupled via hybridization between the polynucleotide molecules.

In addition to the disclosure as provided herein, an enzyme may be attached directly to a substrate including a nanopore, or may be attached indirectly to a substrate including a nanopore via a linker, by any of the suitable means disclosed in e.g. WO2010/086603, WO2010/004273, WO2010/004265 and/or WO 2012/033524.

Polynucleotide Synthesis Molecule

The methods of the invention involve a process of extending a polynucleotide synthesis molecule with a transfer nucleotide to form an extended polynucleotide synthesis molecule. This process may then be repeated multiple times to further extend the polynucleotide synthesis molecule with further transfer nucleotides to form a synthetic polynucleotide molecule of a desired length and having a desired pre-defined nucleotide sequence.

The polynucleotide synthesis molecule may be provided in a form wherein a portion of the polynucleotide synthesis molecule is attached to another molecule which may act a scaffold molecule. A scaffold molecule may be a polynucleotide molecule or any other suitable polymer, as further described herein. A scaffold molecule may be a polynucleotide molecule which is capable of hybridising with the whole or a portion of the polynucleotide synthesis molecule to form the scaffold.

The polynucleotide synthesis molecule may be provided without attachment to a scaffold molecule. In such cases the polynucleotide synthesis molecule is typically provided in single-stranded form.

The polynucleotide synthesis molecule may be provided in a form wherein at least a portion of the polynucleotide synthesis molecule is tethered to the nanopore or to the substrate. A polynucleotide synthesis molecule may be attached to a nanopore or to the substrate by any suitable means described and defined herein, including any of the attachment methods described herein including in the section "Attachment of feeder molecule handling moieties to substrates", provided the relevant functions and capabilities as described above are maintained.

Figure 2:
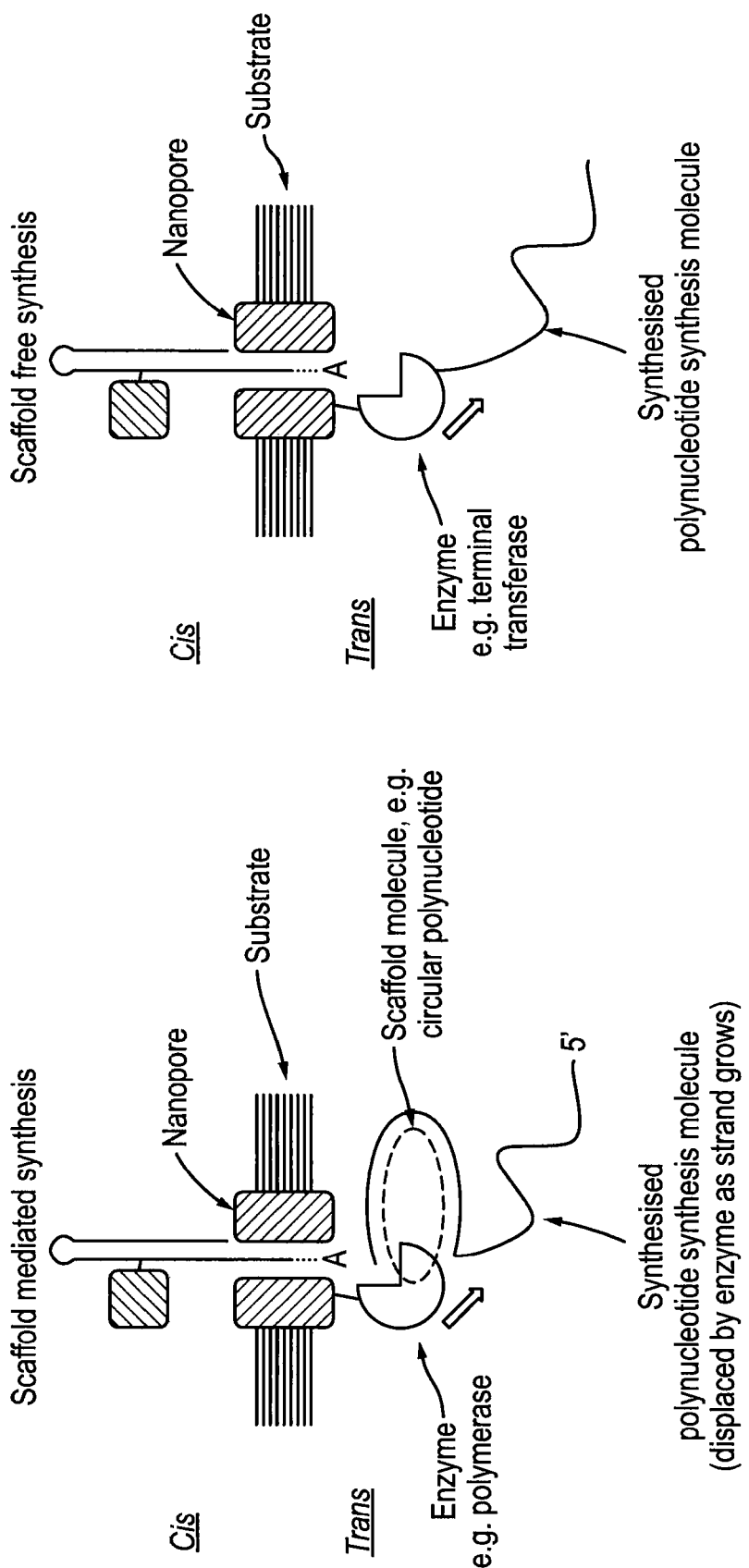
FIG. 2 shows an example overview of scaffold molecule mediated synthesis and scaffold molecule free synthesis.

An exemplary non-limiting overview of scaffold molecule mediated synthesis and scaffold molecule free synthesis is provided in FIG. 2.

A polynucleotide synthesis molecule may be provided in a variety of suitable forms.

Single-Stranded Polynucleotide Synthesis Molecule

Prior to the first extension process, the polynucleotide synthesis molecule may be provided in a single-stranded form, or in a substantially single-stranded form. For example, the polynucleotide synthesis molecule may be provided in a form wherein it is not hybridised to or otherwise bound to a different polynucleotide molecule such as a scaffold molecule. In such an embodiment the first and subsequent extension processes may comprise extending the single-stranded polynucleotide synthesis molecule to form a synthetic single-stranded polynucleotide molecule.

A single-stranded polynucleotide synthesis molecule is provided in proximity to an enzyme on the trans side of the substrate.

The enzyme is any suitable enzyme capable of extending the single strand of a single-stranded molecule comprising nucleic acid, as described in more detail herein. Such an enzyme does not, for example, require a nucleic acid molecule to be hybridised to another nucleic acid molecule in order to act as a primer, and thus the enzyme can act on a naked unhybridised single-stranded molecule in the absence of a scaffold molecule.

Prior to the first extension process, the single-stranded polynucleotide synthesis molecule is provided, in proximity with the enzyme, with a 3'-OH group if required by the enzyme to catalyse the extension process.

Prior to the first extension process, the single-stranded polynucleotide synthesis molecule may be provided as an oligonucleotide having a length of six or more nucleotides.

Preferably, the polynucleotide synthesis molecule is provided in proximity to the enzyme by virtue of the fact that the enzyme will naturally associate with the polynucleotide synthesis molecule in order to perform its function, e.g. to act as a polymerase or transferase etc. In this way, it is not necessary to provide the enzyme and/or polynucleotide synthesis molecule with any specific chemical group(s) or functionality to facilitate their association.

Association between the single-stranded polynucleotide synthesis molecule and enzyme may optionally be promoted or facilitated by providing one or more coupling moieties. The coupling moiety may be a protein, protein complex, chemical group(s) and/or chemical complex which act to tether the polynucleotide synthesis molecule to the enzyme. The coupling moiety may be any suitable linker disclosed herein.

Double-Stranded Polynucleotide Synthesis Molecule

Prior to the first extension process, the polynucleotide synthesis molecule may be provided in a double-stranded form, in a substantially double-stranded form, or in a form comprising a double-stranded region or portion. For example, the polynucleotide synthesis molecule may be provided in a form wherein it is hybridised to or otherwise bound to a different polynucleotide molecule (e.g. a scaffold molecule) to form a double-stranded polynucleotide molecule, or a polynucleotide molecule having a double-stranded region or portion. In such an embodiment, the first and subsequent extension processes may comprise extending one strand of the double-stranded polynucleotide molecule, wherein the strand that is extended is the polynucleotide synthesis molecule, thus forming a synthetic double-stranded polynucleotide molecule comprising the extended polynucleotide synthesis molecule.

A polynucleotide synthesis molecule comprising a double-stranded polynucleotide molecule or portion is provided in proximity to an enzyme on the trans side of the substrate.

The enzyme is any suitable enzyme capable of extending a polynucleotide synthesis molecule, wherein the polynucleotide synthesis molecule is one strand of a double-stranded molecule comprising nucleic acid. In order to extend a polynucleotide synthesis molecule, an enzyme, for example a polymerase, may require the polynucleotide synthesis molecule to be hybridised to another nucleic acid molecule. In this way, the polynucleotide synthesis molecule acts as a primer for the enzyme, and the primer is extended by the normal function of the enzyme.

Prior to the first extension process, the polynucleotide synthesis molecule is provided, in proximity with the enzyme, with a 3'-OH group if required by the enzyme to catalyse the extension process, e.g. a 3'-OH group at the terminal end of the polynucleotide synthesis molecule wherein the terminal end of the polynucleotide synthesis molecule is hybridised to another nucleic acid molecule.

Prior to the first extension process, the polynucleotide synthesis molecule may be provided as an oligonucleotide having a length of six or more nucleotides.

Preferably, the polynucleotide synthesis molecule is provided in proximity to the enzyme by virtue of the fact that the enzyme will naturally associate with the polynucleotide synthesis molecule in order to perform its function, e.g. to act as a polymerase or transferase etc. In this way, it is not necessary to provide the enzyme and/or polynucleotide synthesis molecule with any specific chemical group(s) or functionality to facilitate their association.

Association between the polynucleotide synthesis molecule comprising a double-stranded polynucleotide molecule or portion thereof and enzyme may be promoted or facilitated by providing one or more coupling moieties. The coupling moiety may be a protein, protein complex, chemical group(s) and/or chemical complex which may act to tether the polynucleotide synthesis molecule to the enzyme. The coupling moiety may be any suitable linker disclosed herein.

In one embodiment of the methods of the invention, a polynucleotide synthesis molecule is extended by the action of an enzyme, typically a polymerase, which requires for its function the polynucleotide synthesis molecule to be hybridised to another nucleic acid molecule, so as to act as a primer for the enzyme, and the primer is extended by the normal function of the enzyme. In such an embodiment, a normal function of the enzyme may be to extend the primer by making a "copy" of the other nucleic acid molecule. By "copy" it is meant the synthesis of a new portion of the strand extended from the primer having a nucleotide sequence that is complementary to the nucleotide sequence of the other nucleic acid molecule in terms of Watson-Crick base-pairing. The present invention relates to methods wherein the polynucleotide synthesis molecule is extended with desired transfer nucleotides in a template-independent manner. Thus in embodiments wherein a polynucleotide synthesis molecule is extended by the action of an enzyme which requires for its function the polynucleotide synthesis molecule to be hybridised to another nucleic acid molecule, so as to act as a primer for the enzyme, each extension process uses the other nucleic acid molecule as a scaffold which supports the newly-synthesised strand, rather than a template per se which is "copied" to form complementary Watson-Crick base-pairing in the newly-synthesised strand.

In one embodiment a scaffold polynucleotide molecule which can act as a support for the polynucleotide synthesis molecule may be provided with multiple universal nucleotides. A universal nucleotide is capable of pairing with multiple different nucleotides. The universal nucleotide may or may not form a bond with a paired nucleotide. The universal nucleotide may bond to some degree with a paired nucleotide. For example, inosine is capable of pairing with adenine, guanine, thymine, uracil or cytosine. A universal nucleotide is described further herein. Thus, if an enzyme such as polymerase acts to extend the terminal nucleotide of a polynucleotide synthesis molecule at the terminal, e.g. 3' end, and the hybridised scaffold polynucleotide molecule comprises a universal nucleotide such as inosine at the next nucleotide position opposite the terminal end of the polynucleotide synthesis molecule in the "downstream" (i.e. extended) direction, then the polymerase will extend the polynucleotide synthesis molecule downstream with the transfer nucleotide which is presented to the enzyme by the feeder molecule, irrespective of which nucleobase the transfer nucleotide harbours. The transfer nucleotide, once incorporated into the polynucleotide synthesis molecule, will then pair with the inosine which occupies the opposite position in the scaffold polynucleotide molecule. In this way, the inosine nucleotide of the scaffold polynucleotide molecule is not "copied" to the extended polynucleotide synthesis molecule in strict Watson-Crick base pairing terms, but rather merely "supports" the incoming transfer nucleotide which is transferred to the terminal end of the polynucleotide synthesis molecule by the action of the enzyme.

Figure 3:
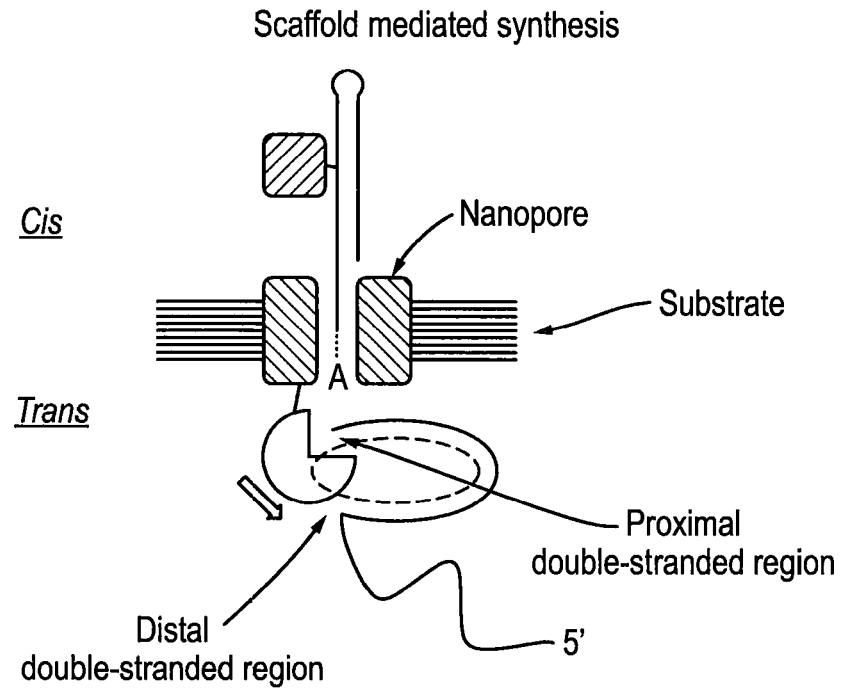
FIG. 3 depicts the use of an example scaffold molecule.

With reference to FIG. 3, merely by way of illustration, a scaffold polynucleotide molecule, such as described above, may be a circular polynucleotide molecule, and wherein the polynucleotide synthesis molecule or extended polynucleotide synthesis molecule or a portion thereof is hybridised to at least a portion of the scaffold polynucleotide molecule to form a double-stranded molecule or to form a double-stranded portion of the polynucleotide synthesis molecule and a single stranded portion of the polynucleotide synthesis molecule. In such an embodiment, the terminal end of the polynucleotide synthesis molecule to be extended in the next extension process (typically the 3' end) is comprised in a region which may be referred to, for example, as the proximal double-stranded region of the polynucleotide synthesis molecule. The opposite end of the polynucleotide synthesis molecule (typically the 5' end) may be comprised in a region which may be referred to, for example, as the distal double-stranded region of the polynucleotide synthesis molecule. Or, the distal double-stranded region of the polynucleotide synthesis molecule may be the region which comprises the end of the double-stranded portion of the polynucleotide synthesis molecule and the beginning of the single-stranded portion of the polynucleotide synthesis molecule. In such an embodiment, the enzyme extends the polynucleotide synthesis molecule at its terminal end in the proximal double-stranded region of the polynucleotide synthesis molecule. As the enzyme continues to extend the polynucleotide synthesis molecule in the proximal double-stranded region it may, due to the circularity of the polynucleotide scaffold molecule, simultaneously displace the polynucleotide synthesis molecule from the scaffold molecule in the distal double-stranded region. In this way the enzyme may "ratchet around" the scaffold molecule leading to the synthesised strand of the extended polynucleotide synthesis molecule gradually extending as a single-stranded molecule displaced from the scaffold molecule away from distal double-stranded region. Thus in such an embodiment the enzyme may preferably be provided with a nucleic strand displacement activity.

The polynucleotide synthesis molecule which was provided prior to the first extension process may become incorporated as part of the final desired synthetic polynucleotide molecule. In this case, the polynucleotide synthesis molecule which was provided prior to the first extension process may itself comprise a desired transfer nucleotide sequence. Alternatively, it may be desirable to remove all or a portion of the polynucleotide synthesis molecule which was provided prior to the first extension process, so that it is not part of the final synthetic polynucleotide molecule. In such cases, the polynucleotide synthesis molecule which was provided prior to the first extension process may comprise a cleavage site, for example a recognition sequence for a cleavage enzyme such as a restriction endonuclease. Alternatively, such a cleavage site may be synthesised as part of the process of extending the polynucleotide synthesis molecule.

Thus in any of the methods of the invention the polynucleotide synthesis molecule may be provided with a cleavage site prior to a first extension process. Any of the methods of the invention may comprise repeating the extension process multiple times to further extend the polynucleotide synthesis molecule with further transfer nucleotides so as to synthesise a polynucleotide synthesis molecule comprising a cleavage site to remove the polynucleotide synthesis molecule which was provided prior to the first extension process, or to remove a portion thereof. In any of the methods of the invention the polynucleotide synthesis molecule may be extended with a cleavable nucleotide.

In all synthesis methods described herein the polynucleotide synthesis molecule is extended in any given cycle. Such an extended polynucleotide synthesis molecule is then referred to as a polynucleotide synthesis molecule with respect to the next cycle of synthesis. Thus the term "polynucleotide synthesis molecule" is not intended to refer exclusively to the molecule prior to the first extension reaction but is a general term which refers to the polynucleotide molecule which is being extended in any given cycle of synthesis.

Scaffold Molecule

The scaffold molecule may comprise any suitable material provided that it is compatible with the enzyme and allows the enzyme and other components of the methods to perform their respective functions.

In any of the methods of the invention the scaffold molecule may comprise a molecule comprising DNA, RNA, peptide nucleic acid (PNA), locked nucleic acid (LNA), unlocked nucleic acid (UNA), bridged nucleic acid (BNA), glycerol nucleic acid (GNA), threose nucleic acid (TNA), morpholino nucleic acid, phosphorothioate nucleic acid, methylphosphonate nucleic acid, other nucleic acid, morpholino, peptide, oligopeptide, polypeptide, or other polymer.

The scaffold molecule can be composed of a molecule comprising composites of the above-described materials. For example, the scaffold molecule may comprise a portion comprising a polynucleotide and a portion comprising another different polymer. Any suitable combination of materials is envisaged provided that the scaffold molecule is capable of performing its function as described above. The scaffold molecule can be composed of a molecule comprising any combination of the above materials.

The scaffold molecule may be linear or continuous, e.g. circular. Preferably, the scaffold molecule is continuous, e.g. circular.

The scaffold molecule may support extension of a polynucleotide synthesis molecule which comprises DNA or RNA. For example, the scaffold molecule may support extension of a polynucleotide synthesis molecule which comprises DNA by the use of a DNA dependent DNA polymerase enzyme. The scaffold molecule may support extension of a polynucleotide synthesis molecule which comprises RNA by the use of an DNA dependent RNA polymerase enzyme.

Reduction of Unbinding of Enzyme from Polynucleotide Synthesis Molecule or Scaffold Molecule In any of the methods defined or described herein, the enzyme used to catalyse incorporation of the transfer nucleotide may comprise a functionality which reduces or inhibits unbinding of the polynucleotide synthesis molecule and/or the scaffold molecule from the enzyme. Such a functionality is provided to allow the polynucleotide synthesis molecule to remain tethered to the enzyme for many cycles of transfer nucleotide incorporation.

Any suitable means for achieving a reduction of unbinding function may be employed.

Directed evolution techniques, conventional screening, rational or semi-rational engineering/mutagenesis methods or any other suitable methods may be used to modify the enzyme used to catalyse incorporation of the transfer nucleotide to provide and/or optimise the required unbinding function.

Alternatively, another enzyme or protein associated with the incorporation enzyme may be provided, and optionally modified as above if necessary or desirable, to provide the required function. For example, the enzyme used to catalyse incorporation of the transfer nucleotide may be coupled to another protein or molecule which provides reduced unbinding function. An example of another such enzyme is a helicase enzyme.

Closed-complex chemistry techniques for modifying proteins and enzymes to provide polynucleotide unbinding function by "closing" the enzyme around the polynucleotide molecule are known in the art. One example is disclosed in WO2014/013260. Engineering of artificial disulphide bonds into the enzyme may also provide closed-complex functionality. Such techniques may be applied in the present methods to increase binding between incorporation enzyme and the polynucleotide synthesis molecule. The unbinding function may be applied to the polynucleotide synthesis molecule itself and/or the scaffold molecule.

Transfer Nucleotides

A nucleotide for use in extending a polynucleotide synthesis molecule in accordance with the methods of the invention is referred to as a transfer nucleotide. Preferably, the transfer nucleotide which is used to extend a polynucleotide synthesis molecule in any given cycle is pre-defined. In otherwords, the identity of the transfer nucleotide is pre-selected, e.g. pre-selected to be adenine, thymine, cytosine, guanine, uracil, or any other nucleotide as required. By pre-defining one, more or each nucleotide to be transferred to the polynucleotide synthesis molecule it is possible to synthesise a polynucleotide synthesis molecule having a pre-defined sequence.

A transfer nucleotide for use in extending a polynucleotide synthesis molecule in accordance with the methods of the invention typically contains a nucleobase, a sugar and at least one phosphate group. The nucleobase is typically heterocyclic. Suitable nucleobases include purines and pyrimidines and more specifically adenine, guanine, thymine, uracil and cytosine. The sugar is typically a pentose sugar. Suitable sugars include, but are not limited to, ribose and deoxyribose. The nucleotide is typically a ribonucleotide or deoxyribonucleotide. The nucleotide typically contains a monophosphate, diphosphate or triphosphate.

The transfer nucleotide can be a naturally occurring nucleotide. The transfer nucleotide can be an artificial nucleotide such as a non-natural nucleotide or nucleotide analogue, or a universal nucleotide. An artificial nucleotide may be modified structurally either in the base, sugar or phosphate or combination and may still be utilised by a polymerase, transferase or other enzyme for the purposes of extending a polynucleotide synthesis molecule.

As noted previously, in any of the methods of the invention reference to the extension of a polynucleotide synthesis molecule with "a" transfer nucleotide in any given cycle of synthesis also relates to the extension of a polynucleotide synthesis molecule with multiple transfer nucleotides in a single transfer reaction, for example extension of a polynucleotide synthesis molecule simultaneously with dinucleotides, trinucleotides etc.

Methods and reagents for extension of polynucleotide synthesis molecules with multiple nucleotides in a single transfer reaction are known in the art, such as disclosed in e.g. U.S. Pat. No. 7,060,440B1. Such methods may also be implemented with the use of ligase enzymes, as described herein.

Any of the following nucleotides may be used as transfer nucleotides to extend a polynucleotide synthesis molecule using the methods of the invention described herein.

Natural Nucleotides

Natural nucleotides may be used to extend a polynucleotide synthesis molecule. Natural nucleotides contain a natural nucleobase, a sugar and a phosphate group. Natural nucleobases comprise adenosine (A), thymine (T), uracil (U), guanine (G) and cytosine (C).

Non-Natural Nucleotides, Nucleotide Analogues and Universal Nucleotides

A non-natural nucleotide may also be used to extend a polynucleotide synthesis molecule using any of the methods described herein. Any of the following non-natural nucleotides, nucleotide analogues, universal nucleotides, including any modifications, may be incorporated using any of the methods described herein, provided the incorporation reaction is not undesirably inhibited.

A non-natural nucleotide may be a nucleotide unit of a peptide nucleic acid (PNA), a locked nucleic acid (LNA), an unlocked nucleic acid (UNA), a bridged nucleic acid (BNA), a glycerol nucleic acid (GNA), a threose nucleic acid (TNA), a morpholino nucleic acid, a phosphorothioate nucleic acid, a methylphosphonate nucleic acid or other nucleic acid.

A non-natural nucleotide may comprise a modified sugar and/or a modified nucleobase.

Modified sugars include but are not limited to 2'-O-methylribose sugar.

Modified nucleobases include but are not limited to methylated nucleobases. Methylation of nucleobases is a recognised form of epigenetic modification which has the capability of altering the expression of genes and other elements such as microRNAs. Methylation of nucleobases occurs at discrete loci which are predominately dinucleotide consisting of a CpG motif, but may also occur at CHH motifs (where H is A, C, or T). Typically, during methylation a methyl group is added to the fifth carbon of cytosine bases to create methylcytosine. Thus modified nucleobases include but are not limited to 5-methylcytosine such as 5-hydroxymethylcytosine (HOMeC).

Methods of the invention may use a universal nucleotide as a transfer nucleotide. A universal nucleotide is one wherein the nucleobase will bond, e.g. hydrogen bond, to some degree to the nucleobase of any nucleotide of the predefined sequence. A universal nucleotide is preferably one which will bond, e.g. hydrogen bond, to some degree to nucleotides comprising the nucleosides adenosine (A), thymine (T), uracil (U), guanine (G) and cytosine (C). The universal nucleotide may bond more strongly to some nucleotides than to others. For instance, a universal nucleotide (I) comprising the nucleoside, 2'-deoxyinosine, will show a preferential order of pairing of I-C>I-A>I-G approximately =I-T.

Examples of possible universal nucleotides which may be used are inosines or nitro-indoles. The universal nucleotide preferably comprises one of the following nucleobases: hypoxanthine, 4-nitroindole, 5-nitroindole, 6-nitroindole, 3-nitropyrrole, nitroimidazole, 4-nitropyrazole, 4-nitrobenzimidazole, 5-nitroindazole, 4-aminobenzimidazole or phenyl (C6-aromatic ring. The universal nucleotide more preferably comprises one of the following nucleosides: 2'-deoxyinosine, inosine, 7-deaza-2'-deoxyinosine, 7-deazainosine, 2-aza-deoxyinosine, 2-aza-inosine, 4-nitroindole 2'-deoxyribonucleoside, 4-nitroindole ribonucleoside, 5-nitroindole 2' deoxyribonucleoside, 5-nitroindole ribonucleoside, 6-nitroindole 2' deoxyribonucleoside, 6-nitroindole ribonucleoside, 3-nitropyrrole 2' deoxyribonucleoside, 3-nitropyrrole ribonucleoside, an acyclic sugar analogue of hypoxanthine, nitroimidazole 2' deoxyribonucleoside, nitroimidazole ribonucleoside, 4-nitropyrazole 2' deoxyribonucleoside, 4-nitropyrazole ribonucleoside, 4-nitrobenzimidazole 2' deoxyribonucleoside, 4-nitrobenzimidazole ribonucleoside, 5-nitroindazole 2' deoxyribonucleoside, 5-nitroindazole ribonucleoside, 4-aminobenzimidazole 2' deoxyribonucleoside, 4-aminobenzimidazole ribonucleoside, phenyl C-ribonucleoside or phenyl C-2'-deoxyribosyl nucleoside.

Some examples of universal bases are shown below:

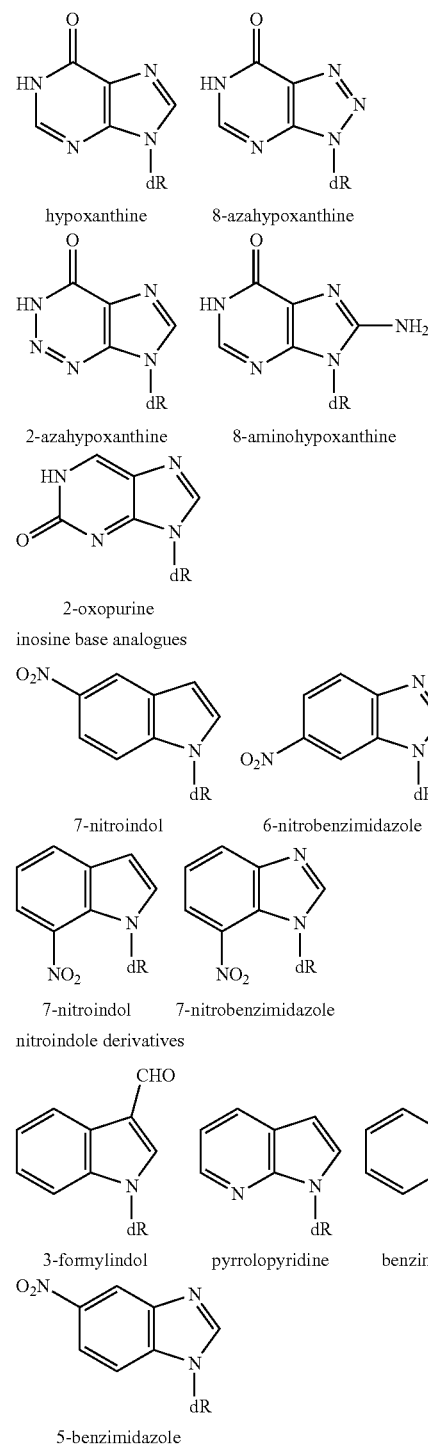

hypoxanthine  8-azahypoxanthine 2-azahypoxanthine  8-aminohypoxanthine 2-oxopurine inosine base analogues 7-nitroindol  6-nitrobenzimidazole 7-nitroindol  7-nitrobenzimidazole nitroindole derivatives 3-formylindol  pyrrolopyridine  benzimidazole 5-benzimidazole nitropyrrol and nitrobenzene derivatives

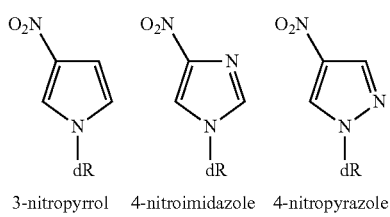

3-nitropyrrol    4-nitroimidazole    4-nitropyrazole

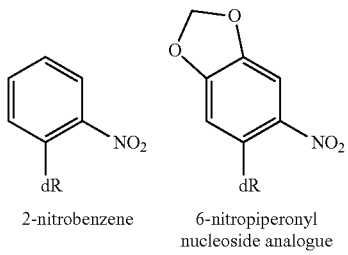

2-nitrobenzene    6-nitropiperonyl
                  nucleoside analogue

Universal nucleotides incorporating cleavable bases may also be used, including photo- and enzymatically-cleavable bases, some examples of which are shown below.

Photocleavable Bases:

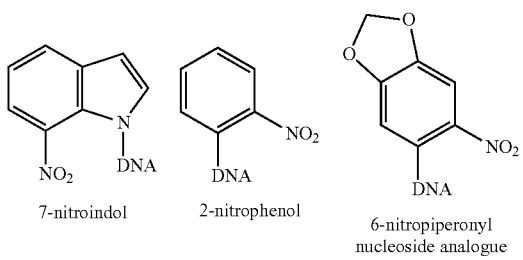

7-nitroindol    2-nitrophenol    6-nitropiperonyl
                                 nucleoside analogue Base Analogues Cleavable by Endonuclease III:

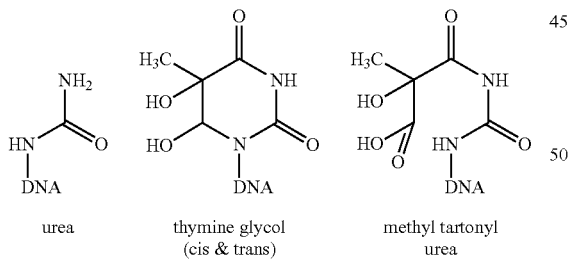

urea    thymine glycol    methyl tartonyl
        (cis & trans)     urea

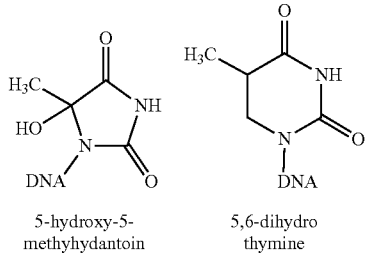

5-hydroxy-5-       5,6-dihydro
methyhydantoin     thymine

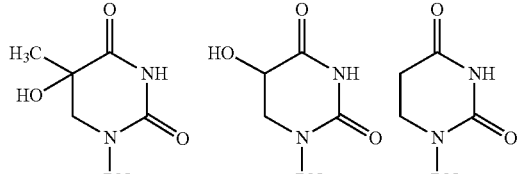

5-hydroxy-6-       5-hydroxy-6-       5,6-dihydro-
hydrothymine       hydrouracil        uracil

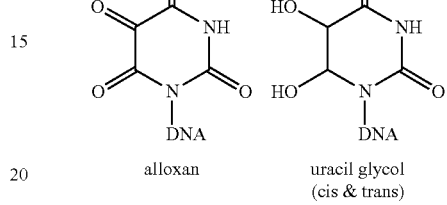

alloxan            uracil glycol
                   (cis & trans)

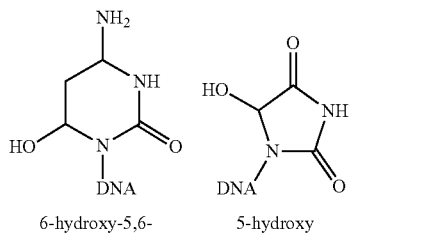

6-hydroxy-5,6-     5-hydroxy
dihydrocytosine    hydantoin

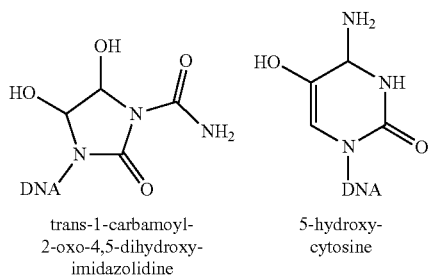

trans-1-carbamoyl-         5-hydroxy-
2-oxo-4,5-dihydroxy-       cytosine
imidazolidine

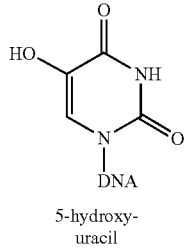

5-hydroxy-
uracil

Base Analogues Cleavable by Formamidopyrimidine DNA Glycosylase (Fpg):

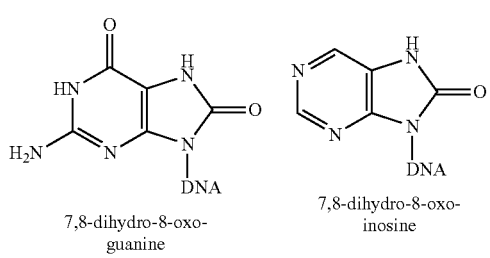

7,8-dihydro-8-oxo-    7,8-dihydro-8-oxo-
guanine               inosine

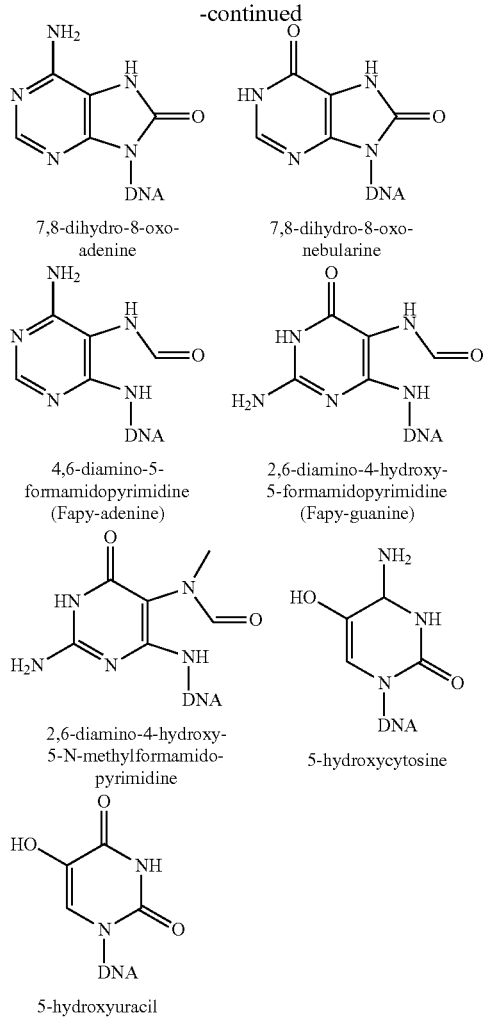

7,8-dihydro-8-oxo-adenine 7,8-dihydro-8-oxo-nebularine 4,6-diamino-5-formamidopyrimidine
(Fapy-adenine)

2,6-diamino-4-hydroxy-5-formamidopyrimidine
(Fapy-guanine)

2,6-diamino-4-hydroxy-5-N-methylformamido-pyrimidine 5-hydroxycytosine 5-hydroxyuracil Base Analogues Cleavable by 8-Oxoguanine DNA Glycosylase (hOGG1):

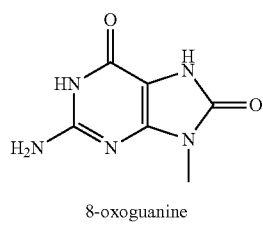

8-oxoguanine

Base Analogues Cleavable by hNeil1:

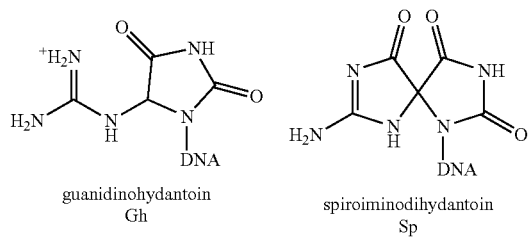

guanidinohydantoin
Gh spiroiminodihydantoin
Sp

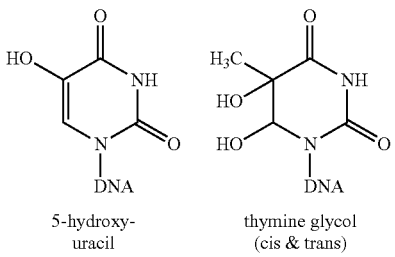

5-hydroxy-uracil thymine glycol
(cis & trans)

Base Analogues Cleavable by Thymine DNA Glycosylase (TDG):

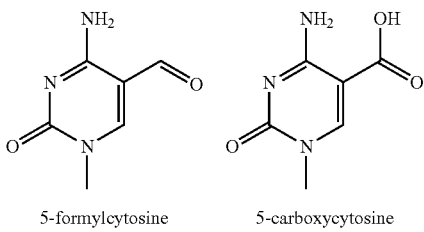

5-formylcytosine 5-carboxycytosine

Base Analogues Cleavable by Human Alkyladenine DNA Glycosylase (hAAG):

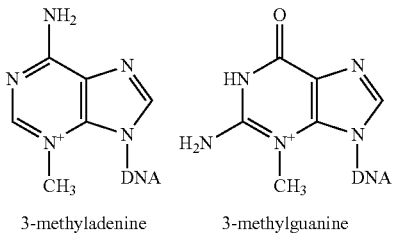

3-methyladenine 3-methylguanine

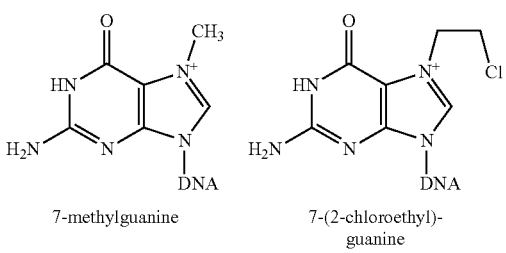

7-methylguanine 7-(2-chloroethyl)-guanine

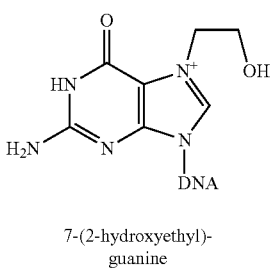

7-(2-hydroxyethyl)-guanine

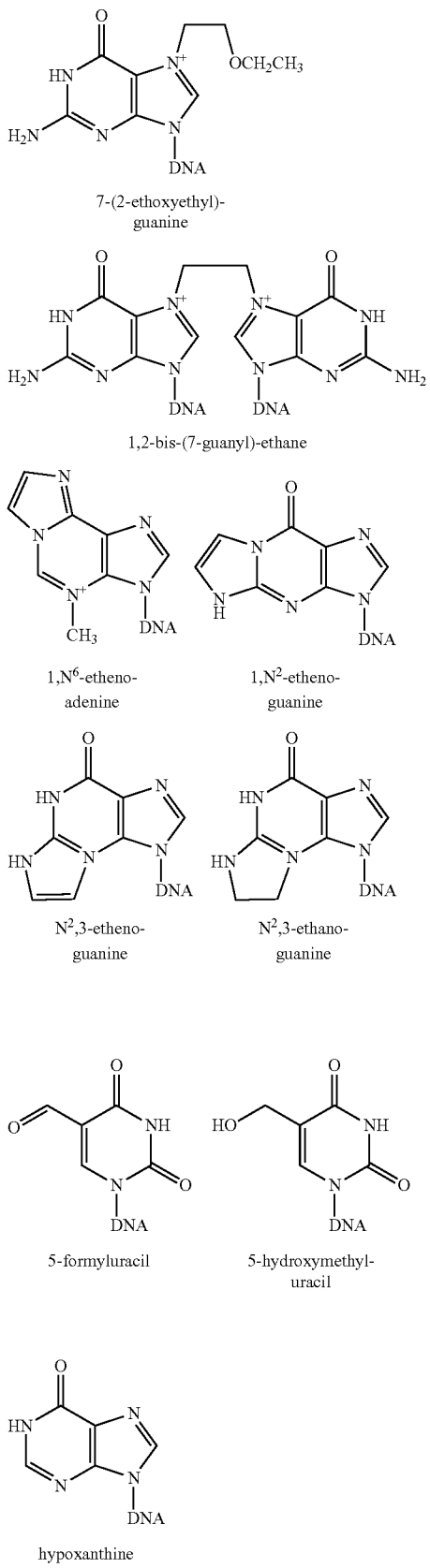

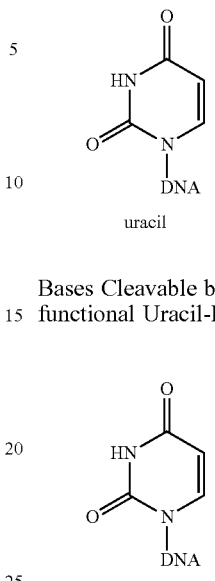

Bases Cleavable by Uracil DNA Glycosylase:

uracil

Bases Cleavable by Human Single-Strand-Selective Monofunctional Uracil-DNA Glycosylase (SMUG1):

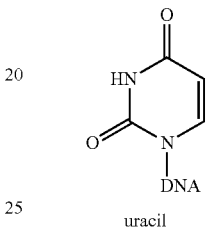

uracil

Bases Cleavable by 5-Methylcytosine DNA Glycosylase (ROS1):

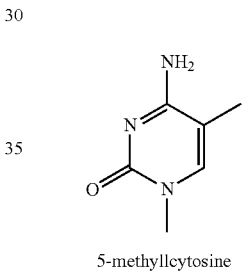

5-methylcytosine (see S. S. David, S. D. Williams *Chemical reviews* 1998, 98, 1221-1262 and M. I. Ponferrada-Marín, T. Roldán-Arjona, R. R. Ariza' *Nucleic Acids Res* 2009, 37, 4264-4274).

Artificial nucleotides also include nucleotides incorporating bases such as 2'-deoxynucleoside, alpha phosphorothiolate, phosphorothioate nucleotide triphosphates, purine or pyrimidine conjugates that have other desirable properties, such as fluorescence. Other examples of purine and pyrimidine bases include pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, imidazo[1,5-a]1,3,5 triazinones, 9-deazapurines, imidazo[4,5-d]pyrazines, thiazolo[4,5-d]pyrimidines, pyrazin-2-ones, 1,2, 4-triazine, pyridazine; and 1,3,5 triazine.

Typically, the nucleotide, such as in the form attached the feeder molecule, will be a nucleoside triphosphate.

Typically, the enzyme will catalyse the extension of the polynucleotide synthesis molecule with the addition of a nucleoside monophate unit derived from the nucleoside triphosphate, optionally attached to the feeder molecule.

Thus in any of the methods of the invention in order to extend a polynucleotide synthesis molecule to form a molecule comprising DNA, a nucleotide may be incorporated from a dNTP, e.g. via the action of a DNA polymerase enzyme, ligase enzyme or transferase enzyme.

In any of the methods of the invention in order to extend a polynucleotide synthesis molecule to form a molecule comprising RNA, a nucleotide may be incorporated from a NTP, e.g. via the action of a RNA polymerase enzyme, ligase enzyme or transferase enzyme.

Alternatively, triphosphates can be substituted by tetraphosphates or pentaphosphates (generally oligophosphate). These oligophosphates can be substituted by other alkyl or acyl groups:

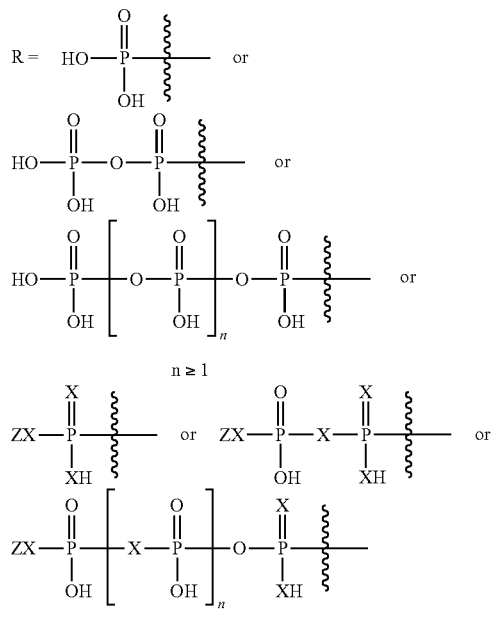

In any of the methods described and defined herein, enzymes which may conventionally be used to incorporate dNTP to form a molecule comprising DNA may also be used to incorporate NTP to form a molecule comprising RNA. Conversely, enzymes which may conventionally be used to incorporate NTP to form a molecule comprising RNA may also be used to incorporate dNTP to form a molecule comprising DNA. Directed evolution techniques, conventional screening, rational or semi-rational engineering/mutagenesis methods or any other suitable methods may be used to alter any such enzyme to provide and/or optimise the required nucleotide incorporation function.

Reversible Blocking Groups

As described herein, the methods of the present invention do not require the extension of a polynucleotide synthesis molecule by the incorporation of a nucleotide comprising a reversible blocking group followed by a de-blocking step prior to the next extension cycle. Nevertheless, in certain situations it may be desirable to incorporate one or more nucleotides including at least one nucleotide which comprises a reversible blocking group in order to halt the extension processes at a desired point, for example at the end of a cycle of synthesising a polynucleotide of desired length and sequence in order to prevent further undesirable incorporation.

Any suitable reversible blocking group may be attached to a nucleotide to prevent further extension by the enzyme following the incorporation of a nucleotide in a given cycle. In any the methods of the invention the reversible blocking group is preferably a reversible terminator group. Examples of reversible terminators are provided below.

Propargyl Reversible Terminators:

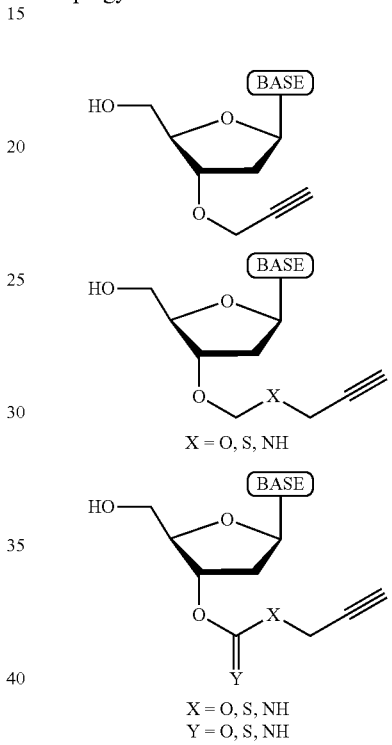

Allyl Reversible Terminators:

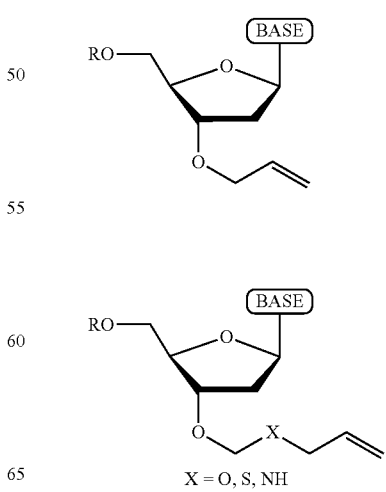

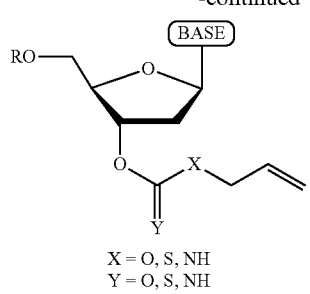
X = O, S, NH
Y = O, S, NH
Cyclooctene Reversible Terminators:
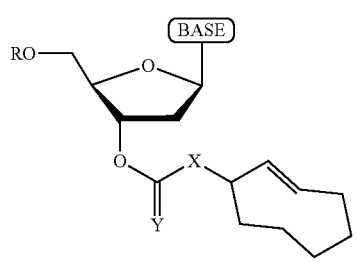
X = O, S, NH
Y = O, S, NH
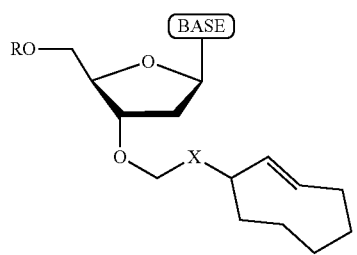
X = O, S, NH
Y = O, S, NH
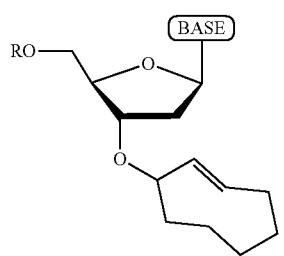
Cyanoethyl Reversible Terminators:
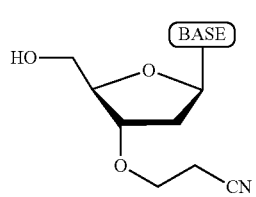
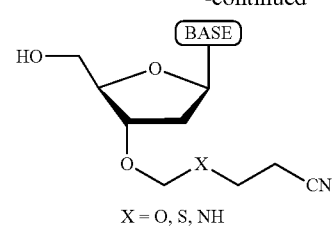
X = O, S, NH
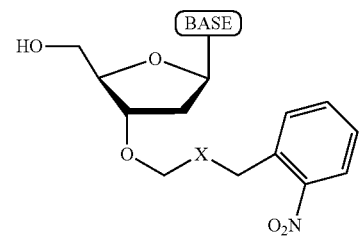
X = O, S, NH
Y = O, S, NH
Nitrobenzyl Reversible Terminators:
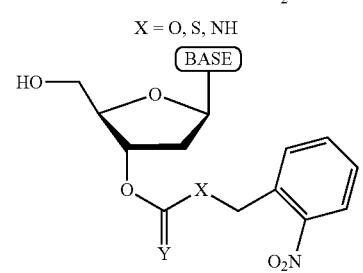
X = O, S, NH
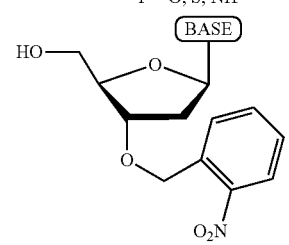
X = O, S, NH
Y = O, S, NH Disulfide Reversible Terminators:

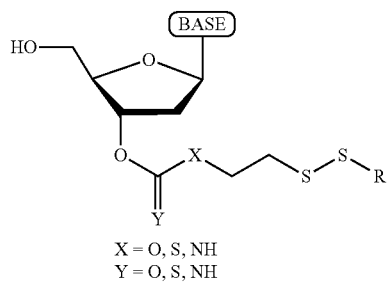

X = O, S, NH
Y = O, S, NH

Azidomethyl Reversible Terminators:

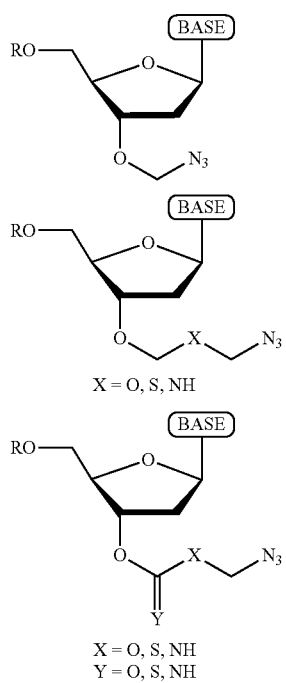

X = O, S, NH

X = O, S, NH
Y = O, S, NH

Aminoalkoxy Reversible Terminators:

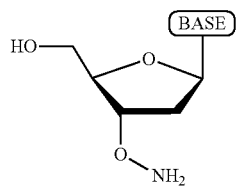

Nucleosides with bulky groups attached to the nucleobase can serve as substitutes for a reversible terminator group on the 3'-hydroxy group and can block further incorporation. This group can be deprotected by TCEP or DTT producing natural nucleotides.

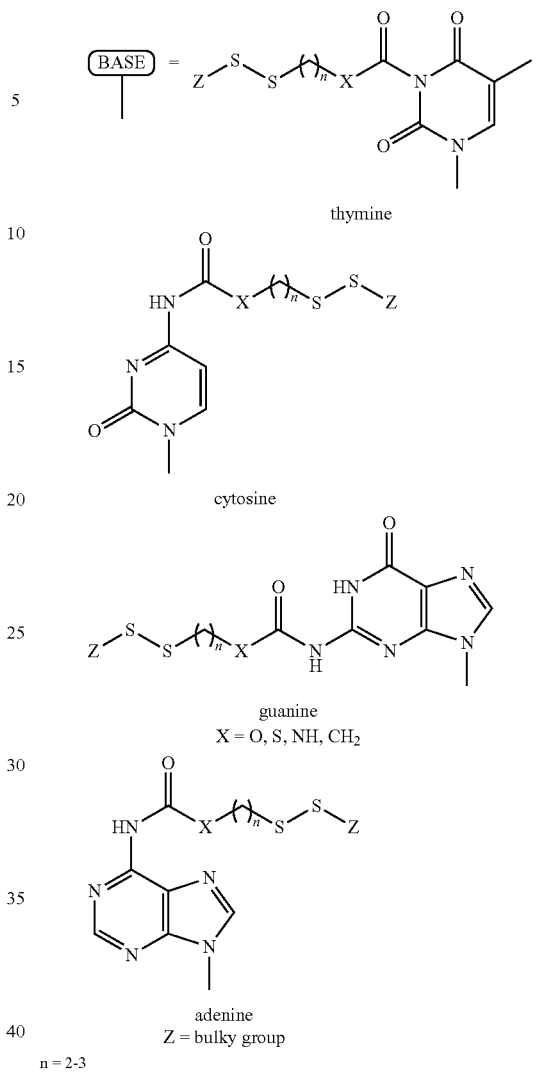

thymine cytosine guanine
X = O, S, NH, CH$_2$ adenine
Z = bulky group n = 2-3

For synthesising DNA polynucleotides according to any of the methods of the invention, modified nucleosides may be 3'-O-modified-2'-deoxyribonucleoside-5'-O-triphosphate. For synthesising RNA polynucleotides according to any of the methods of the invention, modified nucleosides may be 3'-O-modified-2'-ribonucleoside-5'-O-triphosphate. Modified dNTPs may be 3'-O-allyl-dNTPs and 3'-O-azidomethyl-dNTPs.

3'-O-allyl-dNTPs are shown below.

3'-O-allyl-dTTP:

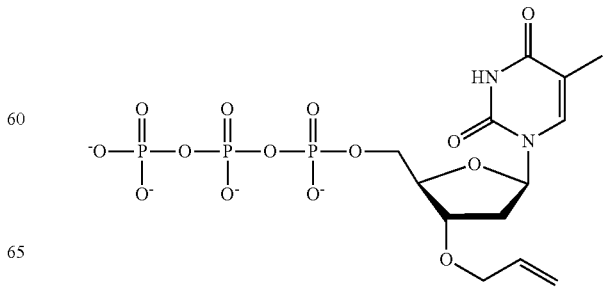

-continued

3'-O-allyl-dCTP:

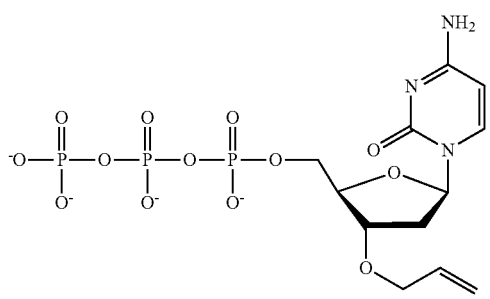

3'-O-allyl-dATP:

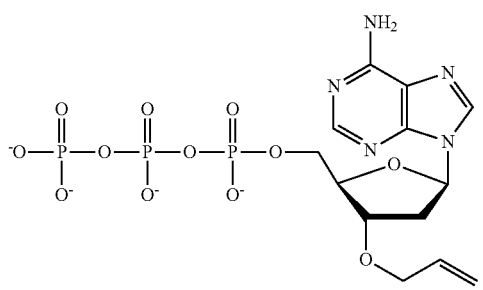

3'-O-allyl-dGTP:

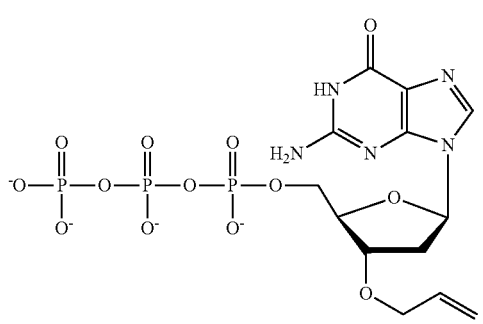

3'-O-azidomethyl-dNTPs are shown below.

3'-O-azidomethyl-dTTP:

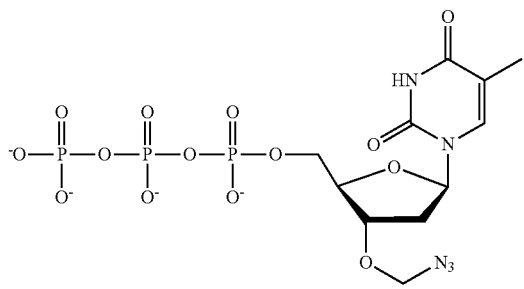

-continued

3'-O-azidomethyl-dCTP:

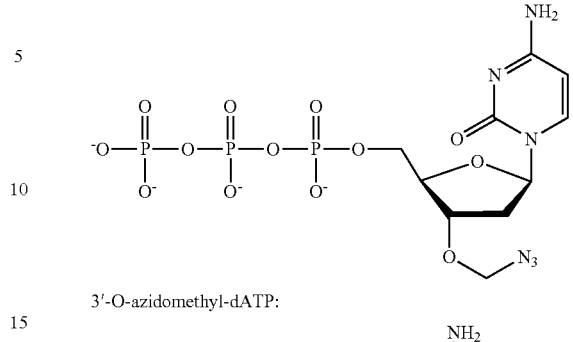

3'-O-azidomethyl-dATP:

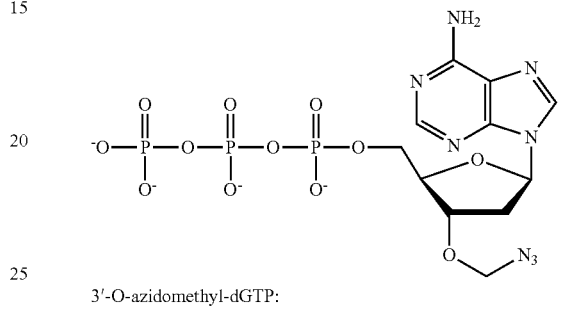

3'-O-azidomethyl-dGTP:

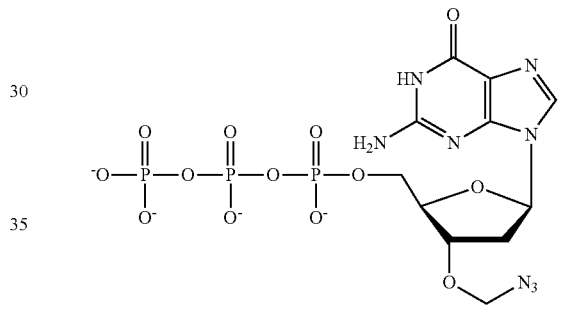

Any suitable reagent may be used to remove a reversible terminator group via deprotection step if desired.

A deprotecting reagent may be tris(carboxyethyl)phosphine (TCEP). TCEP may be used to remove reversible terminator groups from 3'-O-allyl-nucleotides (in conjunction with Pd°) and 3'-O-azidomethyl-nucleotides following incorporation.

Examples of deprotecting reagents are provided below.

Propargyl Reversible Terminators:
Treatment by Pd catalysts—$Na_2PdCl_4$, $PdCl_2$.
Ligands can be used e. g.: Triphenylphosphine-3,3',3"-trisulfonic acid trisodium salt.

Allyl Reversible Terminators:
Treatment by Pd catalysts—$Na_2PdCl_4$, $PdCl_2$.
Ligands can be used e. g.: Triphenylphosphine-3,3',3"-trisulfonic acid trisodium salt.

Azidomethyl Reversible Terminators:
Treatment by thiol (mercaptoethanol or dithiothreitol), or Tris (2-carboxyethyl)phosphine—TCEP.

Cyanoethyl Reversible Terminators:
Treatment by fluoride—ammonium fluoride, tetrabutylammonium fluoride (TBAF).

Nitrobenzyl Reversible Terminators:
Exposure to UV light

Disulfide Reversible Terminators:
Treatment by thiol (mercaptoethanol or dithiothreitol), or Tris (2-carboxyethyl)phosphine—TCEP.

Aminoalkoxy Reversible Terminators:
Treatment by nitrite ($NO_2^-$, $HNO_2$) pH=5.5

Feeder Molecules

In the methods of the invention a transfer nucleotide is moved through a nanopore in a substrate and incorporated into a polynucleotide synthesis molecule by the action of an enzyme.

In certain embodiments described and defined herein, the transfer nucleotide may be moved through the nanopore without attachment to any other molecule, such as a feeder molecule. In such methods verification processes may performed by determining the identity and/or integrity of the transfer nucleotide by direct detection of the nucleotide in the nanopore. Such means are disclosed in e.g. Clarke et al. Nature Nanotechnology volume 4, pages 265-270 (2009). In any such method the nanopore may for example comprise an internalised molecular adaptor such as cyclodextrin.

A nucleotide may alternatively be moved through a nanopore by a feeder molecule. In such methods the nucleotide is provided on the cis side of the substrate attached to the feeder molecule. The feeder molecule is then moved into the nanopore such that the nucleotide is translocated to the trans side of the substrate and such that the nucleotide is contacted with the enzyme, as described in more detail herein. By "contacted" it is meant that the nucleotide is brought sufficiently close to the enzyme that the enzyme is capable of catalysing the transfer of the nucleotide from the feeder molecule to the polynucleotide synthesis molecule. Thus the feeder molecule acts as a vehicle for moving the nucleotide from the cis side to the trans side of the substrate.

A portion of the feeder molecule is passed through the nanopore from the cis side of the substrate to the trans side of the substrate. Preferably, the entire feeder molecule is not passed through the nanopore to the trans side. Rather the feeder molecule may be passed through the nanopore such that a portion of the feeder molecule remains positioned within the nanopore with the terminal end and a further portion of the feeder molecule protruding through the nanopore at the trans side of the substrate. Thus by use of the term "through" as used herein it is not meant that the feeder molecule is necessarily passed in its entirety through the nanopore and across the substrate to the trans side. The feeder molecule may be positioned within the nanopore by the action of one or more blocking moieties, as described further herein.

The feeder molecule with an attached nucleotide may be provided on the cis side of the substrate free in solution. Alternatively the feeder molecule may be tethered to surface of the substrate, as described further herein, such as disclosed in international patent application publication umber WO2012164270. The feeder molecule is then moved toward and into a nanopore. Movement of the feeder molecule is typically achieved under an applied potential, typically by applying a voltage across the substrate as described further herein. Application of a voltage across the substrate leads to ion current flow through the nanopore and attraction of the feeder molecule and its capture within the nanopore, as described in more detail herein. The feeder molecule may be provided as a charged molecule capable of responding to electrical charge and capable of moving under electrical control. The feeder molecule is preferably comprised of a charged material. Alternatively, an applied potential can create an electroosmotic flow around and within the channel of a nanopore which may act to capture neutral molecules. Thus the feeder molecule may be uncharged.

The dimensions, form and composition of the feeder molecule can vary, provided that the feeder molecule is capable of moving into and within a nanopore under electrical control so as to perform its function as described herein.

In any of the methods of the invention the feeder molecule may comprise a molecule comprising DNA, RNA, peptide nucleic acid (PNA), locked nucleic acid (LNA), unlocked nucleic acid (UNA), bridged nucleic acid (BNA), glycerol nucleic acid (GNA), threose nucleic acid (TNA), morpholino nucleic acid, phosphorothioate nucleic acid, methylphosphonate nucleic acid, other nucleic acid, morpholino, peptide, oligopeptide, polypeptide, or other polymer.

The feeder molecule can be composed of a molecule comprising composites of the above-described materials. For example, the feeder molecule may comprise a portion comprising a polynucleotide and a portion comprising another different polymer. Any suitable combination of materials is envisaged provided that the feeder molecule is capable of performing its function as described herein. The feeder molecule can be composed of a molecule comprising any combination of the above materials.

The feeder molecule may be single-stranded, may be double-stranded or may comprise both single-stranded and double-stranded regions. Typically cDNA, RNA, GNA, TNA or LNA are single stranded. The feeder molecule may comprise a region of secondary or tertiary structure, e.g. as described herein in relation to blocking moieties. The feeder molecule may e.g. comprise a hairpin structure.

Figure 4:
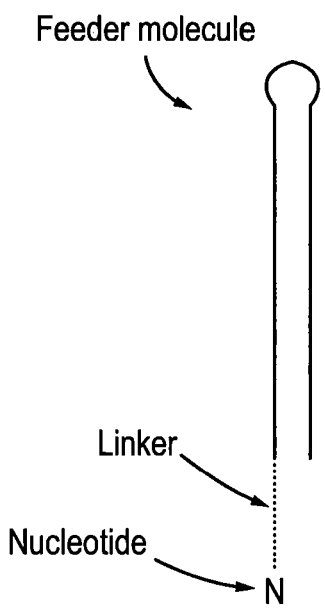
FIG. 4 depicts an example feeder molecule.
Figure 5:
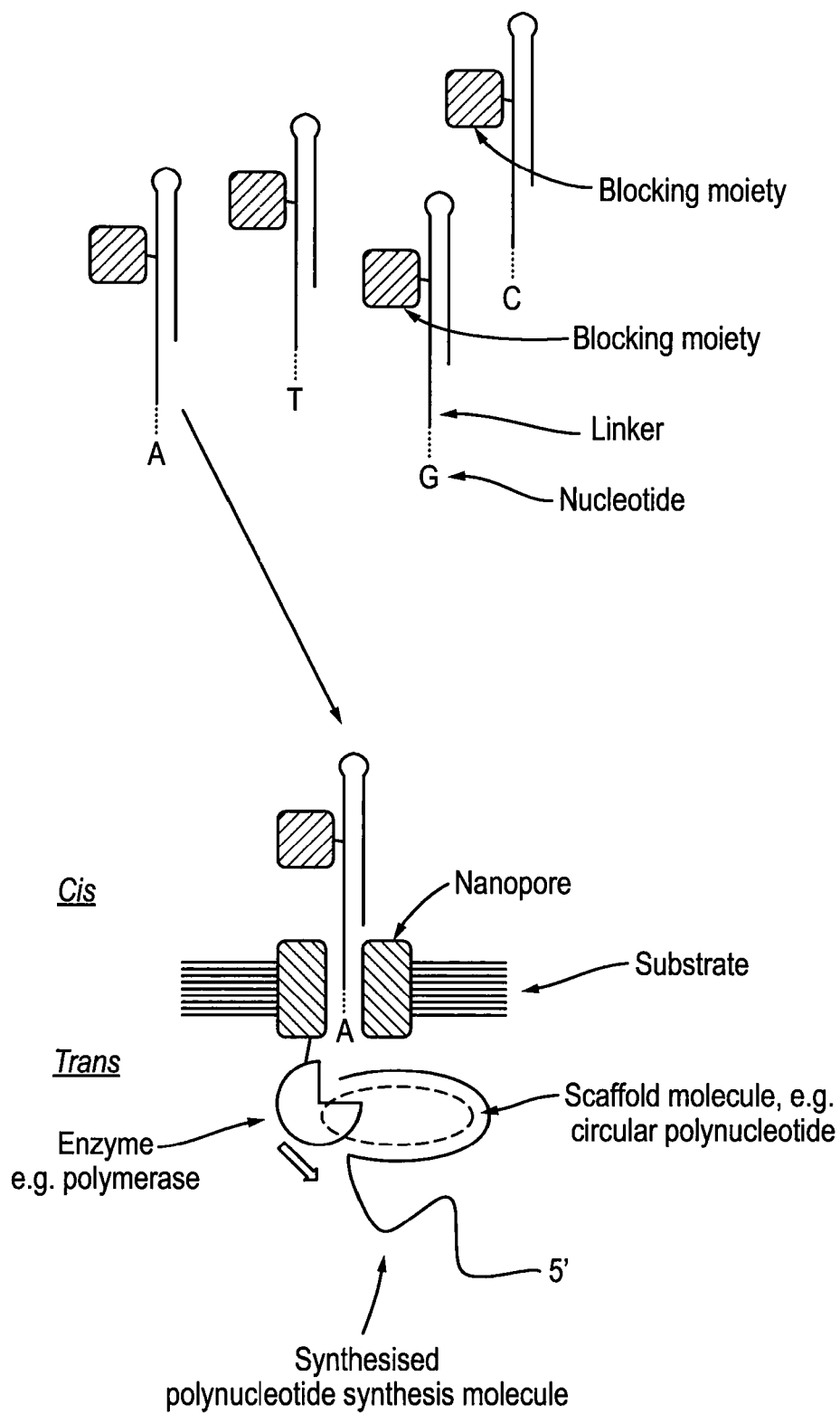
FIG. 5 shows examples of feeder molecules and use in the present methods.

The feeder molecule may be provided with a transfer nucleotide attached to the feeder molecule via a linker as described in more detail herein. Examples of feeder molecules and use in the present methods are shown in FIGS. 4 and 5.

In a preferred embodiment the feeder molecule comprises a polynucleotide molecule comprising DNA.

A feeder molecule typically consists of or comprises an oligonucleotide of any composition described above. The feeder molecule may consist of or comprise an oligonucleotide of any suitable length. The length of the oligonucleotide may be 10 nucleotides or more, 11 nucleotides or more, 12 nucleotides or more, 13 nucleotides or more, 14 nucleotides or more, 15 nucleotides or more, 16 nucleotides or more, 17 nucleotides or more, 18 nucleotides or more, 19 nucleotides or more, 20 nucleotides or more, 21 nucleotides or more, 22 nucleotides or more, 23 nucleotides or more, 24 nucleotides or more, 25 nucleotides or more, 26 nucleotides or more, 27 nucleotides or more, 28 nucleotides or more, 29 nucleotides or more, 30 nucleotides or more, 40 nucleotides or more, 50 nucleotides or more, 60 nucleotides or more, 70 nucleotides or more, 18 nucleotides or more, 90 nucleotides or more, 100 nucleotides or more, 110 nucleotides or more, 120 nucleotides or more, 130 nucleotides or more, 140 nucleotides or more, 150 nucleotides or more, 160 nucleotides or more, 170 nucleotides or more, 180 nucleotides or more, 190 nucleotides or more, 200 nucleotides or more, 210 nucleotides or more, 220 nucleotides or more, 230 nucleotides or more, 240 nucleotides or more, 250 nucleotides or more, 260 nucleotides or more, 270 nucleotides or more, 280 nucleotides or more, 290 nucleotides or more or 300 nucleotides or more.

Linkers and Attachment Moieties

The feeder molecule is provided on the cis side of the substrate with an attached nucleotide. The nucleotide is attached to the feeder molecule by any suitable means known in the art.

The nucleotide is typically provided as an attached nucleoside triphosphate (either NTP or dNTP).

The nucleotide may be attached directly to the feeder molecule, such as via a covalent bond between the third phosphate group of the nucleoside triphosphate and any suitable chemical group of the feeder molecule.

The nucleotide may be attached to the feeder molecule by a linker. Any suitable linker may be used, provided that it is capable of allowing the feeder molecule to pass into and through a nanopore under control as described herein. The choice of linker may depend upon the choice of material of which the feeder molecule is comprised.

The linker may comprises a phosphate group linker comprising one phosphate group, or a polyphosphate group linker comprising two, three or more phosphate groups.

For example, the phosphate group linker of the feeder molecule may comprise one or more phosphate groups attached in tandem to the three tandem phosphate groups of the nucleoside triphosphate.

In any of the methods of the invention a linker may comprise a hydrocarbon chain. A hydrocarbon chain may comprise from 2 to 20 or more carbon atoms. The hydrocarbon chain may comprise an alkylene group, e.g. a C2-20 alkylene group. The hydrocarbon chain may be optionally interrupted by an aryl or a heteroaryl ring e.g. a triazole ring, e.g. a 1,2,3-triazole ring. The hydrocarbon chain may be optionally interrupted by an ester group (i.e. —C(O)—O—) or an amide group (i.e. —C(O)—N(H)—), preferably an amide group.

The linker may be defined by the formula:

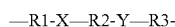

wherein:
R1, R2 and R3 are C2-10 alkylene groups, preferably C3-6 alkylene groups,
X is an aryl or a heteroaryl ring, preferably a 1,2,3-triazole ring, and
Y is —C(O)—O— or —C(O)—N(H)—, preferably a —C(O)—N(H)— group.

A $C_{2-20}$ alkylene group is an unsubstituted or substituted bidentate moiety obtained by removing two hydrogen atoms, either both from the same carbon atom, or one from each of two different carbon atoms, of a hydrocarbon compound having from 2 to 20 carbon atoms (unless otherwise specified), which may be aliphatic or alicyclic, and which may be saturated, partially unsaturated, or fully unsaturated. Thus, the term "alkylene" includes the subclasses alkenylene, alkynylene, cycloalkylene, etc. An alkylene group may be unsubstituted or substituted, for instance, as specified above for alkyl. Typically a substituted alkylene group carries 1, 2 or 3 substituents, for instance 1 or 2. In this context, the prefix $C_{2-20}$ denotes the number of carbon atoms, or range of number of carbon atoms. For example, the term "C2-20 alkylene," as used herein, pertains to an alkylene group having from 2 to 20 carbon atoms.

An aryl group is a substituted or unsubstituted, monocyclic or bicyclic aromatic group which typically contains from 5 to 20 carbon atoms, more typically from 5 to 14 carbon atoms, preferably from 6 to 14, or for instance from 6 to 10, or from 5 to 10, carbon atoms in the ring portion. Examples include phenyl, naphthyl, indenyl and indanyl groups. The ring atoms of an aryl group may include one or more heteroatoms (as in a heteroaryl group). Such a heteroaryl group is a substituted or unsubstituted mono- or bicyclic heteroaromatic group which typically contains from 5 to 10 atoms in the ring portion (i.e. it is a 5- to 10-membered ring) including one or more heteroatoms.

The linker may comprise the following structure:

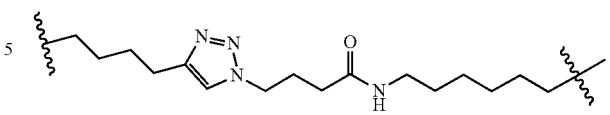

A nucleotide may be attached to a feeder molecule by any suitable method known in the art, provided that the attachment maintains the capability of the feeder molecule to move through the nanopore so as to allow the nucleotide to contact the enzyme, and provided that the attachment maintains the capability of the nucleotide to act as a substrate for the enzyme.

A nucleotide may be attached to a feeder molecule by means such as chemical interactions and co-valent attachment. Any of the attachment methods described herein in the section "Attachment of feeder molecule handling moieties to substrates" may be applied mutatis mutandis for the purposes of attaching a nucleotide to a feeder molecule, provided the relevant functions and capabilities of the nucleotide and feeder molecule are maintained, as described above.

In addition to the disclosure as provided herein, a nucleotide may be attached to a feeder molecule by any suitable means disclosed in WO2010/086603, WO2010/004273, WO2010/004265 and/or WO 2012/033524.

A linker may optionally comprise one or more spacer molecules (units).

The linker may comprise e.g. a C3 spacer or an Sp9 spacer.

The linker may comprise e.g. a poly(ethylene glycol) (PEG) spacer.

The linker may comprise e.g. a polyphosphate spacer.

The linker may comprise one or more further spacer molecules attached to the first spacer molecule. For example, the linker may comprise multiple e.g. C3 spacer molecules.

Shown below are some non-limiting examples of spacer molecules (C3 and Sp9) which may be used to attach a nucleotide to a feeder molecule.

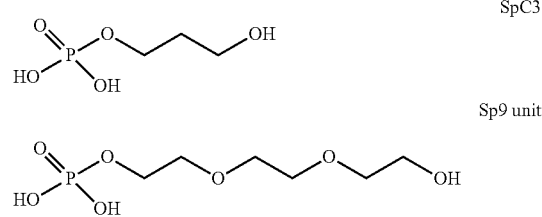

Attachment Point of Nucleotide to Feeder Molecule

The linker, or the nucleotide itself in the absence of a linker, may be attached to the feeder molecule at any suitable position on the feeder molecule, provided that the nucleotide is capable of contacting the enzyme when the feeder molecule is moved to a suitable position within the nanopore, as described herein, and provided that the attachment maintains the capability of the nucleotide to act as a substrate for the enzyme.

The linker or nucleotide may be attached to the feeder molecule at or near the terminal end of the feeder molecule, being the terminal end which is passed through the nanopore from the cis side of the substrate to the trans side, such as depicted in FIG. 6A. The linker or nucleotide may be attached to the feeder molecule at a positon along the length of the feeder molecule such as depicted in FIG. 6B.

Leader

The terminal end of the feeder molecule which is passed through the nanopore from the cis side of the substrate to the trans side may comprise a leader sequence or leader molecule, particularly in embodiments wherein the linker or nucleotide is not attached to the terminal end of the feeder molecule.

A leader molecule may help facilitate orientation, passage and movement of the feeder molecule into and through the nanopore. It may protect the terminal end of the feeder molecule and prevent unwanted functional effects, such as undesirable reactions between the terminal end of the feeder molecule and other components of the system, such as the enzyme and/or polynucleotide synthesis molecule.

A leader molecule may comprise any suitable group, molecule or moiety provided the above-described function is maintained.

A leader molecule may comprise a hydrocarbon chain. The hydrocarbon chain may comprise an alkyl group, e.g. comprising from 2 to 20 carbon atoms, e.g. a C2-20 alkyl group.

The leader may comprise a "C3 Spacer" comprising 3 carbon atoms (http://www.idtdna.com/site/Catalog/Modifications/Category/6).

The leader may comprise a poly T DNA.

Identification Moiety

A feeder molecule may comprise an identification moiety. The identification moiety can provide the capability of identifying the feeder molecule as having a particular characteristic, e.g. as having an attached nucleotide comprising a specific nucleobase, such as adenine, thymine, cytosine, guanine or uracil.

The identification moiety comprises a characteristic that can be measured or detected so as to establish its identity, and thus to identify the feeder molecule.

An identification moiety may be an identification motif forming part of the feeder molecule, such as a specific polynucleotide sequence. Such a sequence is often referred to as a "barcode" sequence, and provides the capability to uniquely identify a molecule within which the sequence is comprised. Thus in embodiments wherein a feeder molecule may be formed of a molecule comprising a polynucleotide, the feeder molecule may comprise a polynucleotide sequence identification motif (barcode). The polynucleotide motif acting as a barcode may be "read", for example sequenced, as the feeder molecule moves through the nanopore. Alternatively, the barcode may produce a single unique current level so as to establish the identity of the feeder molecule. In addition, the feeder molecule may be moved through the nanopore in a stepped manner comprising one or more pauses or halts in the movement of the feeder molecule through the nanopore so as to facilitate detection of the barcode and thus establish the identity of the feeder molecule. Such stepped movement of a polymer through a nanopore is known in the art, see e.g. Derrington, I. M, et al., PNAS, 2010, 107 (37) 16060-16065.

The use of a nanopore for sequencing a polynucleotide molecule is an established methodology (see e.g. WO2016/059427). These sequencing methods may be combined with the polynucleotide extension methods of the invention.

In these sequencing methods, successive measurements of a polynucleotide molecule are taken from a detection element comprising a nanopore during translocation of the polynucleotide molecule through the nanopore. Some property of the system depends on the nucleotide units of the polynucleotide molecule in the nanopore, and measurements of that property are taken. The data gathered in this way comprises measurements, such as measurements of ion current, where each translocation of the sequence through the sensitive part of the nanopore results in a slight change in the measured property. The electrical operation of a detection element comprising a nanopore for the purposes of determining a polynucleotide sequence is described further herein.

Feeder molecules having attached nucleotides comprising specific nucleobases, such as adenine, thymine, cytosine or guanine can each be provided with polynucleotide sequence identification motifs (barcodes). Translocation of the feeder molecule, or portion thereof, through a nanopore can allow the barcode sequence to be determined by measurement of a property with respect to the nanopore, typically ion current flow under application of an applied potential.

A system of providing an identification moiety to feeder molecules, such as a polynucleotide sequence identification motif, may provide a means of implementing a verification process performed to establish whether a given feeder molecule is attached to the desired transfer nucleotide, as described further herein.

In addition to or as an alternative to a barcode identification moiety, any suitable molecule that creates a unique change in current in the nanopore may be used for electrical detection so as to establish the identity of the feeder molecule. As a further example, an identification moiety may be a fluorescent molecule attached to the feeder molecule.

The identity of a transfer nucleotide may be established without the requirement for a separate identification moiety. In such a case the transfer nucleotide itself may be identified directly when positioned within the nanopore. Such detection may be achieved when the transfer nucleotide is attached to a feeder molecule, or when the transfer nucleotide is moved through the nanopore in the absence of a feeder molecule. Such detection of an individual nucleotide within a nanopore is known in the art, see e.g. Astier et al. J. Am. Chem. Soc., 2006, 128 (5), pp 1705-1710.

Nanopores

A nanopore is or comprises any pore, channel, aperture, hole etc. in a substrate. A nanopore typically has a size of the order of nanometres, that allows the passage of molecules, such as polymers, therethrough.

A nanopore may be disposed within a substrate. A nanopore may be an aperture formed in a substrate. A nanopore may be disposed within an aperture formed in a substrate. As described further herein, the presence of a substrate defines a cis side of the substrate and a trans side of the substrate. The cis side of the substrate and the trans side of the substrate are typically substantially fluidically isolated from each other, but wherein movement of molecules, such as ions, nucleotides and polymers, from the cis side of the substrate to the trans side of the substrate and vice versa through the channel of the nanopore may be controllably permitted by applying a stimulus, typically an applied potential, across the substrate. The cis side of the substrate may be referred to herein as a cis chamber, a cis reaction chamber, a cis portion, a cis reaction portion or a cis reservoir. Similarly, the trans side of the substrate may be referred to herein as a trans chamber, a trans reaction chamber, a trans portion, a trans reaction portion or a trans reservoir.

It is to be understood that the terms "cis" and "trans" are used herein merely to distinguish one side of a substrate comprising a nanopore from the other side of the substrate.

The terms could equally be used in the opposite orientation provided that consistency is maintained.

The nanopore permits polymer units such as nucleotides to flow from one side of a substrate to the other under the action of an applied potential. The nanopore allows a nucleic acid, such as DNA or RNA, to be moved through a channel in the nanopore under a driving force, typically ionic current flow. A nucleic acid may also move through the channel of its own accord, in the absence of a driving force.

A property that depends on the polymer units translocating through the nanopore may be measured. The property may be associated with an interaction between the polymer and the nanopore. Interaction of the polymer may occur at a constricted region of the nanopore. An analysis system measures the property, producing a measurement that is dependent on the polymer units of the polymer. Preferably, the analysis system measures the property with respect to the nanopore, preferably the analysis system measures the ion current flowing through the nanopore under the action of an applied potential. Thus, a nanopore is structured to permit ions driven by an applied potential to flow from one side of a substrate to the other side of the substrate.

In any of the methods described herein the nanopore may be a biological nanopore, a solid state nanopore, a synthetic nanopore or a hybrid nanopore comprising a biological or synthetic nanopore within a solid state substrate.

Biological Nanopores

A biological nanopore may be a pore comprising a polypeptide or a collection of polypeptides. The nanopore may be a transmembrane protein pore.

The biological nanopore may be a biological monomer or a biological oligomer. The nanopore is preferably made up of several repeating subunits, such as 6, 7 or 8 subunits. The nanopore is more preferably a heptameric pore. The nanopore typically comprises a barrel or channel through which ions may flow. The subunits of the nanopore typically surround a central axis and contribute strands to a transmembrane β barrel or channel or a transmembrane α-helix bundle or channel.

A biological nanopore may be a transmembrane protein pore. Transmembrane protein pores for use in the methods described herein may comprise or be derived from β-barrel pores or α-helix bundle pores. The barrel or channel of the nanopore typically comprises amino acids that facilitate interaction with polymer units such as nucleotides or nucleic acids. These amino acids are preferably located near a constriction of the barrel or channel. The nanopore typically comprises one or more positively charged amino acids, such as arginine, lysine or histidine. These amino acids typically facilitate the interaction between the nanopore and polymer units such as the nucleotides or nucleic acids. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA and ClyA toxin (Cytolysin A (ClyA) portal protein). The transmembrane pore may comprise or be derived from Msp or from α-hemolysin (α-HL) or from Phi29 portal protein.

The transmembrane pore may comprise or be derived from Curli production assembly/transport component (CsgG), alpha-Hemolysin, *Mycobacterium smegmatis* porin A (MspA), Lysenin, aerolysin, cytotoxin K (cytk) or actinoporin fragaceatoxin C (FraC).

A suitable transmembrane protein pore may be derived from Msp, preferably from MspA. Such a pore will be oligomeric and typically comprises 7, 8, 9 or 10 monomers derived from Msp. The nanopore may be a homo-oligomeric pore derived from Msp comprising identical monomers. Alternatively, the nanopore may be a hetero-oligomeric pore derived from Msp comprising at least one monomer that differs from the others. The nanopore may also comprise one or more constructs that comprise two or more covalently attached monomers derived from Msp. Suitable pores are disclosed in WO2012/107778. The nanopore may be derived from MspA or a homolog or paralog thereof.

The biological pore may be a naturally occurring pore or may be a mutant pore. Typical pores are described in WO2010/109197; Stoddart D et al., Proc Natl Acad Sci, 2009, 106(19), pp 7702-7707; Stoddart D et al., Angew Chem Int Ed Engl. 2010, 49(3), pp 556-559; Stoddart D et al., Nano Lett. 2010, 10(9), pp 3633-3637; Butler T et al., Proc Natl Acad Sci, 2008, 105(52), pp 20647-20652; Haque F et al., Nano Today, 2013, 8(1): pp 56-74 and WO2012/107778.

The biological pore may be MS-(B1)8 or MS-(B2)8 as described in WO2016/059427. The amino acid sequence of B2 is identical to that of B1 except for the mutation L88N. The nucleotide sequences encoding MS-(B1)8 and MS-(B2)8 are described in WO2016/059427.

Solid State, Synthetic and Hybrid Nanopores

The nanopore may be a solid state nanopore comprising an aperture formed in a solid state substrate. Solid state substrates are described further herein.

Suitable solid state nanopores may be formed by known processes including for example those described in WO2000/79257.

When the solid state nanopore is an aperture in a solid state substrate, the aperture may be modified, chemically, or otherwise, to enhance its properties as a nanopore.

Any of the nanopores formed in solid state substrate described in Haque F et al. (Nano Today, 2013, 8(1): pp 56-74) may be used in the present methods. Other suitable solid state nanopores and methods of producing them which may be used in the present methods are discussed in U.S. Pat. No. 6,464,842, WO2003/003446, WO2005/061373, U.S. Pat. Nos. 7,258,838, 7,466,069, 7,468,271 and 7,253,434.

The solid state substrate may comprise glass, silicon, such as silicon nitride (SiN) and/or a ($SiO_2$); aluminium, such as aluminium oxide ($Al_2O_3$); titanium, such as titanium oxide ($TiO_2$); hafnium, such as hafnium oxide ($HfO_2$); graphene; and a composite substrate or stack structure substrate comprising two or more of the materials defined above, such as a $SiO_2$/SiN/$SiO_2$ substrate.

The nanopore may be a synthetic nanopore formed, for example, from molecules including proteins, peptides, synthetic organic compounds and nucleic acids. A synthetic nanopore may be, for example, a DNA origami nanopore. Synthetic nanopores are known in the art, see e.g. Howorka, S., 2017, Nature Nanotechnology, 12, pp 619-630.

The nanopore may comprise an aperture formed in a solid state substrate into which aperture is inserted a biological or synthetic nanopore as described above. Such a nanopore may be referred to as a hybrid nanopore as described further herein. In any of the methods of the invention, any suitable biological or synthetic nanopore as described herein may be used in conjunction with any suitable solid state substrate as described herein. The nanopore may comprise a DNA origami-graphene hybrid nanopore, see e.g. Farimani, A. B., et al., 2017, ACS Appl. Mater. Interfaces, 9 (1), pp 92-100.
Devices Comprising Nanopores Since the methods of the invention involve the movement of a transfer nucleotide, e.g. attached to a feeder molecule, through a nanopore under the control of an applied potential, as described herein, in all methods of the invention the nanopore is provided as a component of a device comprising a nanopore and electrical control means.

Furthermore, the methods of the invention optionally involve the use of verification processes, as described herein, to determine the identity and optionally the integrity of a nucleotide e.g. attached to a feeder molecule, and optionally to determine the presence or absence of a nucleotide e.g. attached to a feeder molecule so as to determine whether the enzyme has catalysed the transfer of the nucleotide to the polynucleotide synthesis molecule. As such, in any of the methods of the invention the nanopore may be provided as a component of a detection element comprising a nanopore, electrical control means and detection means, wherein the detection means are operable to determine the presence of, identity of and optionally the integrity of a nucleotide e.g. attached to a feeder molecule. Yet further, in any of the methods of the invention a verification processes, as described herein, may be performed to determine the identity of a nucleotide attached to a feeder molecule by determining the sequence of a polynucleotide sequence identification motif (barcode). As such, in any of the methods of the invention the nanopore may be provided as a component of a detection element comprising a nanopore, electrical control means and detection means, wherein the detection means are operable to take successive measurements of the feeder molecule during movement of the feeder molecule through the nanopore of the detection element.

Devices comprising nanopores are described further herein.

Substrates

In any of the methods described herein the nanopore is provided positioned in a substrate. The substrate may be a biological substrate or a solid state substrate as described herein. Hybrid systems may be provided comprising a biological nanopore provided within a solid state substrate.

Biological Substrates

A biological nanopore may be provided in a biological substrate. The biological nanopore is inserted into the biological substrate.

A biological substrate may be a membrane, such as an amphiphilic layer, for example a lipid bilayer.

An amphiphilic layer is a layer formed from amphiphilic molecules, such as phospholipids, which have both hydrophilic and lipophilic properties. The amphiphilic layer may be a monolayer or a bilayer. The amphiphilic layer may be a block copolymer such as disclosed by Gonzalez-Perez et al., (Langmuir, 2009, 25, pp 10447-10450) or in WO2014/064444.

The membrane may be a lipid bilayer. Analysis of polymers in biological nanopores inserted into lipid bilayers can be performed by single-channel recording. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in WO2006/100484, WO2008/102121, WO2009/077734 and WO2012/033524.

Methods for forming lipid bilayers are known in the art. Suitable methods are disclosed in WO2006/100484, WO2008/102121, WO2009/077734 and WO2012/033524, as well as in Mental and Mueller (Proc. Natl. Acad. Sci. USA., 1972; 69: 3561-3566), in which a lipid monolayer is carried on aqueous solution/air interface past either side of an aperture which is perpendicular to that interface. The method is suitable for protein nanopore insertion. Other common methods of bilayer formation include tip-dipping, painting bilayers and patch-clamping of liposome bilayers. In WO2009/077734, a method is described in which the lipid bilayer is formed from dried lipids, and a method is described in which the lipid bilayer is formed across an opening.

A biological substrate may comprise an outer layer of amphipathic molecules. A biological substrate may comprise a bilayer of amphipathic molecules. The amphipathic molecules may be lipid molecules. The amphipathic molecules may comprise phospholipid molecules. The phospholipid molecules may comprise non-PEGylated phospholipids and PEGylated phospholipids.

In any biological substrate which may comprise an outer layer or bilayer of amphipathic molecules comprising non-PEGylated phospholipid molecules and PEGylated phospholipid molecules, the non-PEGylated phospholipid molecules may be glycerophospholipids and/or the PEGylated phospholipids may be glycerophospholipids.

In any biological substrate which may comprise an outer layer or bilayer of amphipathic molecules comprising non-PEGylated phospholipids which are glycerophospholipids, the non-PEGylated phospholipids may comprise DPhPC.

Any of the amphiphilic molecules described in WO2017/149293 may optionally be used to make biological substrates for performing the methods of the invention.

Where phospholipid molecules comprise non-PEGylated phospholipids and PEGylated phospholipids, from 2.5 to 15 mol % of the phospholipids may be PEGylated phospholipids. Alternatively, from 7.5 to 15 mol % of the phospholipids may be PEGylated phospholipids. Alternatively, from 5 to 15 mol % of the phospholipids may be PEGylated phospholipids. From 10 to 15 mol % of the phospholipids may be PEGylated phospholipids.

Any biological substrate which may comprise an outer layer or bilayer of amphipathic molecules comprising PEGylated phospholipids may comprise phospholipids having a PEG group which has a molecular weight of from 1500 to 5000 g/mol, optionally from 1800 to 2200 g/mol.

In any biological substrate which may comprise an outer layer or bilayer of amphipathic molecules comprising non-PEGylated glycerophospholipids, the non-PEGylated phospholipids may be phospholipids of formula (I):

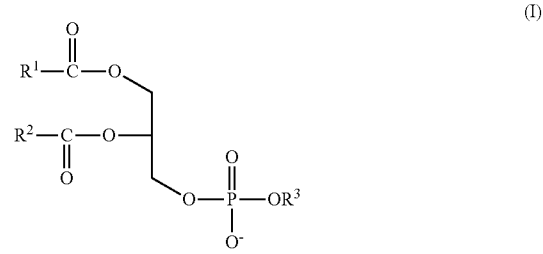

wherein:
R¹ and R², which are the same or different, are selected from $C_{10}$-$C_{25}$ alkyl groups and $C_{10}$-$C_{25}$ alkenyl groups;
R³ is absent such that $OR_3$ is O⁻, or R³ is present and is H, $CH_2CH_2N(R_4)_3^+$, a sugar group, or an amino acid group; and
each R⁴, which is the same or different, is independently selected from H and unsubstituted $C_1$-$C_4$ alkyl.

In any reaction vessel which may comprise an outer layer of amphipathic molecules comprising PEGylated glycerophospholipids the PEGylated phospholipids may be phospholipids of the following formula (II)

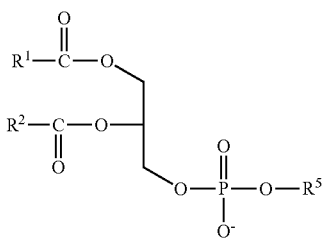

(II)

wherein:
R¹ and R² are as defined above for the phospholipids of formula (I), and R⁵ is a group which comprises poly (ethylene glycol). R⁵ may be —$CH_2CH_2NHC(O)$—$(OCH_2CH_2)_qOCH_3$, —$CH_2CH_2NHC(O)(CH_2)_3C(O)$—$(OCH_2CH_2)_qOCH_3$, —$CH_2CH_2NHC(O)$—$(OCH_2CH_2)_qOH$, or —$CH_2CH_2NHC(O)(CH_2)_3C(O)$—$(OCH_2CH_2)_qOH$, wherein q is an integer from 5 to 10,000.

In any biological substrate which may comprise an outer layer or bilayer of amphipathic molecules comprising PEGylated phospholipids which are glycerophospholipids, the PEGylated phospholipids may comprise DPPE-mPEG2000. The PEGylated phospholipids may comprise from 5 to 15 mol % of DPPE-mPEG2000.

In any biological substrate which may comprise an outer layer or bilayer of amphipathic molecules comprising PEGylated phospholipids which are glycerophospholipids and non-PEGylated phospholipids which are glycerophospholipids, the non-PEGylated phospholipids may comprise DPhPC and the PEGylated phospholipids may comprise DPPE-mPEG2000. In such cases the phospholipids may comprise, for example, from 2.5 to 15 mol % of DPPE-mPEG2000, preferably from 5 to 15 mol % of DPPE-mPEG2000.

A biological substrate may be provided in the form of one or more droplets. A droplet may comprise e.g. a water-in-oil droplet. A nanopore may be positioned within a layer or a bilayer formed as part of a droplet or droplet interface. By way of illustration, droplet interface technology is known in the art, see e.g. Bayley H., et al., 2008, Mol Biosyst. 4(12) pp 1191-1208. A droplet may be composed of any suitable material, such as described further herein.

Solid State Substrates

A solid state substrate is typically not of biological origin. In other words, a solid state layer is typically not derived from or isolated from a biological environment such as an organism or cell, or a synthetically manufactured version of a biologically available structure. Solid state substrates can be formed as layers from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from graphene. Suitable graphene layers are disclosed in WO2009/035647 and WO2011/046706.

A solid state nanopore may be used in combination with additional components which provide an alternative or additional measurement of a polymer, such as tunnelling electrodes (Ivanov A P et al., Nano Lett. 2011 Jan. 12; 11(1): 279-85), or a field effect transistor (FET) device (WO2005/124888) or a complementary-metal-oxide-semiconductor (CMOS) device (Magierowski, S., Biosensors (Basel), 2016, September; 6(3): 42).

Any of the solid state substrates described in Haque F et al. (Nano Today, 2013, 8(1): pp 56-74), U.S. Pat. No. 6,464,842, WO2003/003446, WO2005/061373, U.S. Pat. Nos. 7,258,838, 7,466,069, 7,468,271 and 7,253,434 may be used in the present methods.

Electrical Operation of Nanopore Devices

Techniques for the induced movement of a charged polymer, such as a polynucleotide molecule, through a nanopore and detection of polymer units using a nanopore as a component of a detection device have become well established in recent years (see e.g. Stoddart D et al., Proc Natl Acad Sci, 2009, 106(19), pp 7702-7707; Lieberman K et al, J Am Chem Soc. 2010; 132(50):17961-72, and WO2000/28312). In the present invention, the movement of a feeder molecule through a nanopore in any of the methods described herein, as well as processes for the detection and verification of nucleotides, operates, mutatis mutandis, via such established techniques.

Thus a nanopore is formed in an electrically resistant substrate, as defined herein. An enzyme is provided adjacent the nanopore on one side of the substrate, establishing a trans side and a cis side of the nanopore/substrate. The polynucleotide synthesis molecule to be extended is also provided in proximity to the enzyme. As defined herein, the trans side of the substrate is the side on which the enzyme and polynucleotide synthesis molecule are provided. The cis side of the substrate is the side on which free transfer nucleotides and/or feeder molecules with attached transfer nucleotides are initially provided. A potential gradient may be applied across the nanopore between respective electrodes provided in the cis and trans chambers to induce ion flow through the nanopore. A feeder molecule comprising the transfer nucleotide or a feeder molecule without the transfer nucleotide would be typically charged and drawn into the nanopore under a potential difference depending upon the polarity of the electrodes and the charge of the molecule being drawn into the nanopore. Conversely the transfer nucleotide or feeder molecule may be ejected from the nanopore, moved in an opposite direction or held within the nanopore by reversing or otherwise controlling the potential difference. Ion flow through the nanopore may also contribute to drawing the feeder molecule towards the nanopore aperture and into the nanopore. At least a portion of the feeder molecule, including the attached transfer nucleotide, is translocated into and through the nanopore in the cis to trans direction. Movement of the portion of the feeder molecule through the nanopore may be driven inter alia by the ionic current flow under an applied potential gradient. Other gradients may be applied across the nanopore to induce movement of the feeder molecule through the nanopore such as a pressure or chemical gradient. Movement of the portion of the feeder molecule back through the nanopore in the trans to cis direction can be achieved by the action of a reverse applied potential, e.g. a reverse voltage bias, applied across the substrate.

The present methods preferably involve processes for the detection and verification of nucleotides as described in more detail herein. There processes involve taking of measurements of a property with respect to a nanopore.

The measurements are electrical measurements, in particular current measurements of the ion current flowing through the nanopore. In general, these and other electrical measurements may be made using standard single channel recording equipment such as describes in Stoddart D et al., Proc Natl Acad Sci, 2009, 106(19), pp 7702-7707; Lieberman K et al, J Am Chem Soc. 2010, 132(50), pp 17961-17972, and WO2000/28312. Alternatively, electrical measurements may be made using a multi-channel system, for example as described in WO2009/077734 and WO2011/067559.

In general, when the measurement is current, measurement is of the ion current flow through the nanopore. The ion current may typically be the DC ion current, although in principle an alternative is to use the AC current flow (i.e. the magnitude of the AC current flowing under application of an AC voltage).

Thus sensors can be created by placing a nanopore in an insulating substrate and measuring voltage-driven ionic transport through the pore in the presence of analyte molecules. Fluctuations in the current may reveal the identity of an analyte, such as a nucleotide, that occupies a space within the nanopore. The identity of an analyte is revealed through its distinctive current signature, notably the duration and extent of current block (Braha, O., Walker, B., Cheley, S., Kasianowicz, J. J., Song, L., Gouaux, J. E., and Bayley, H. (1997) Chem. Biol. 4, 497-505; and Bayley, H., and Cremer, P. S. (2001) Nature 413, 226-230). The frequency of occurrence of fluctuations in the current may reveal the concentration of the analyte.

During the interaction between a nucleotide and the nanopore, the nucleotide affects the current flowing through the nanopore in a manner specific for that nucleotide. For example, a particular nucleotide will reduce the current flowing through the nanopore for a particular mean time period and to a particular extent. In other words, the current flowing through the nanopore is distinctive for a particular nucleotide. Control experiments may be carried out to determine the effect a particular nucleotide has on the current flowing through the nanopore. Results from carrying out the method of the invention on a test sample can then be compared with those derived from such a control experiment in order to identify a particular nucleotide.

Exemplary means for detecting the current between the cis and the trans chambers have been described in WO2000/79257, WO 2012/033524, U.S. Pat. Nos. 6,746,594, 6,673, 615, 6,627,067, 6,464,842, 6,362,002, 6,267,872, 6,015,714, and 5,795,782 and U.S. Patent Publication Nos. 2004/0121525, 2003/0104428, and 2003/0104428. Such means include, but are not limited to, electrodes directly associated with the nanopore, at or near the aperture of the nanopore, or placed within chambers on the cis and the trans sides of the substrate. Electrodes may be capable of, but not limited to, detecting ionic current differences across the two chambers or electron tunneling currents across the nanopore aperture or channel. The transport property may be electron flow across the diameter of the aperture, which may be monitored by electrodes disposed adjacent to or abutting the nanopore circumference. Such electrodes can be attached to e.g. an Axopatch 200B amplifier for amplifying a signal.

Electrical measurements of types other than current measurements of ion current through a nanopore as described above may be made. Other possible electrical measurement include: current measurements, impedance measurements, tunnelling measurements (for example as disclosed in Ivanov A et al., Nano Lett. 2011, 11(1), pp 279-285), and field effect transistor (FET) measurements (for example as disclosed in WO2005/124888).

As an alternative to electrical measurements, optical measurements are possible. A suitable optical method involving the measurement of fluorescence is disclosed in Heron J. et al., J. Am. Chem. Soc. 2009, 131(5), pp 1652-1653. Optical measurements may be combined with electrical measurements (Heron J. et al., J. Am. Chem. Soc. 2009, 131(5), pp 1652-1653, and Soni G. et al., Rev Sci Instrum. 2010, 81(1), 014301).

Simultaneous measurements of different natures may be made. The measurement may be of different natures because they are measurements of different physical properties, which may be any of those described above. Alternatively, the measurements may be of different natures because they are measurements of the same physical properties but under different conditions, for example electrical measurements such as current measurements under different applied bias voltages.

Blocking Moieties

In any of the methods of the invention it may be desirable to control the movement of a feeder molecule as it translocates through a nanopore. Such control may be achieved by a variety of means. Control may be achieved using nanopore adaptors and/or feeder molecule handling moieties, as described herein. Control may also be achieved by providing the feeder molecule with one or more blocking moieties.

A "blocking moiety" as described herein is any structure or component which can prevent, pause, hinder or slow the movement of a feeder molecule or a portion of the feeder molecule through a nanopore as it translocates through the nanopore under the action of an applied potential.

Typically a blocking moiety is a molecule, molecular complex, chemical or chemical group applied to or appended to the feeder molecule. Any suitable molecule, complex, chemical, or chemical group may be used. A blocking moiety may be a peptide, oligopeptide, polypeptide, nucleic acid or any other suitable polymer. A blocking moiety may be a single molecule such as a small molecule.

A blocking moiety may be attached to a feeder molecule using any suitable attachment means. Any suitable attachment methods described herein in the section "Linkers and attachment moieties" may be applied mutatis mutandis for the purposes of attaching a blocking moiety to a feeder molecule, depending on the nature and composition of the feeder molecule.

A blocking moiety may be attached to a feeder molecule using one or more linkers. Any of the suitable linkers disclosed herein, and e.g. in WO2010/086603, WO2010/004273, WO2010/004265 and/or WO 2012/033524, may be used.

A blocking moiety may be a molecule of a single species, for example a protein such as horseradish peroxidase (HP).

A blocking moiety may be a complex of one or more molecules such as biotin complexed to avidin/streptavidin.

A blocking moiety may also comprise a portion of the feeder molecule itself. For example, a blocking moiety may comprise a portion of secondary or tertiary structure of the feeder molecule. A blocking moiety may comprise, for example, one or more regions of double stranded nucleic acid, e.g. helix, one or more regions of nucleic acid stem-loop structure (hairpin), one or more nucleic acid cruciform or nucleic acid pseudoknot structures, one or more looped region of unpaired nucleotides, one or more bulge regions, one or more quadruplex regions, one or more regions of cross-linked nucleic acid, or any combination thereof.

One or more blocking moieties may be applied to a feeder molecule at any suitable position along the length of the feeder molecule as desired.

Figure 7:
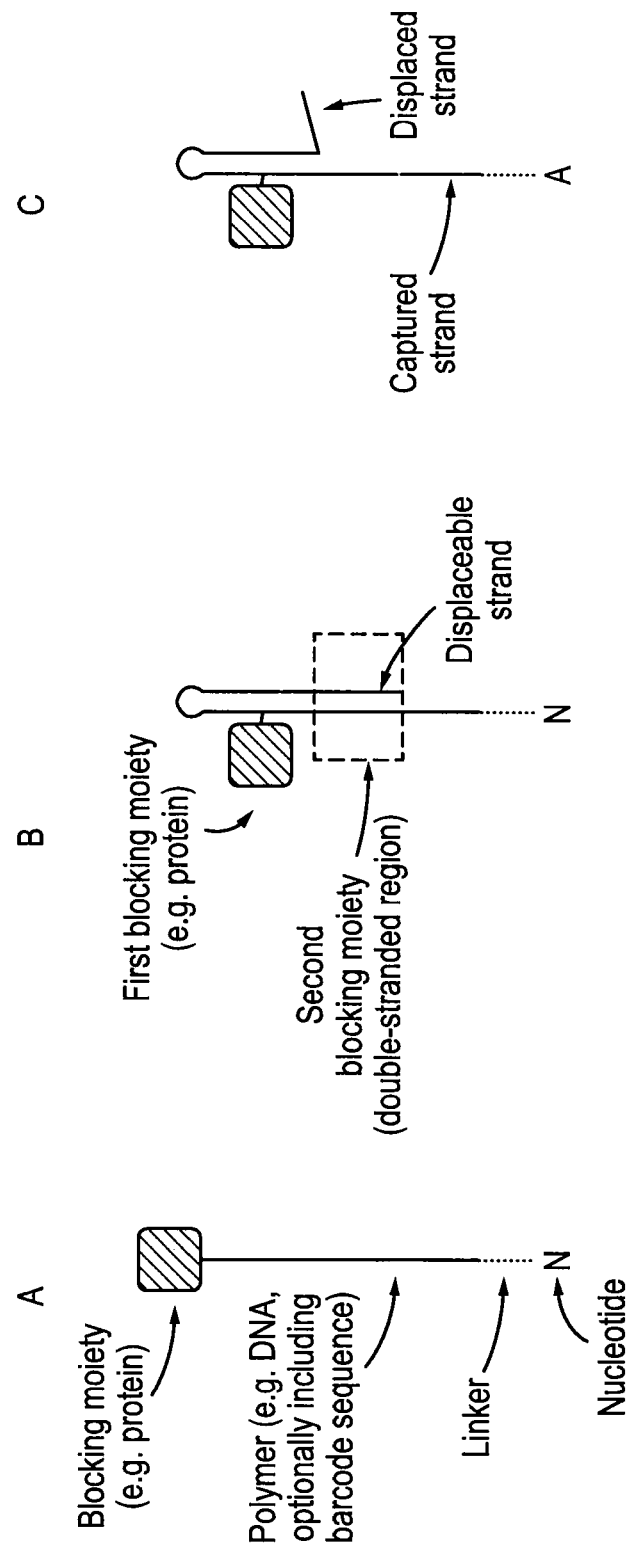
FIG. 7 provides a depiction of blocking moieties applied to feeder molecules.

A blocking moiety may a molecule, molecular complex, chemical or chemical group applied to the feeder molecule indirectly. For example, a blocking moiety may comprise a protein or other molecule associated with the substrate or nanopore, e.g. provided on the trans side of the substrate. Such a protein or other molecule may be attached to the substrate or nanopore by any suitable means, such as described herein. For example any suitable attachment methods described in the section "Linkers and attachment moieties" may be applied mutatis mutandis for the purposes of attaching a blocking moiety to a substrate or nanopore as required. Thus, for example, as the feeder molecule or a portion thereof is translocated across the nanopore a portion of the feeder molecule may contact the blocking moiety attached to the substrate or nanopore whereupon the movement of the feeder molecule may be altered, e.g. slowed or otherwise hindered. Such a protein may comprise, for example, a nucleic acid binding protein, such as a helicase or topoisomerase. Any suitable protein or molecule may be used provided that the desired functions of the components of the system are maintained. FIG. 7 provides a depiction of blocking moieties applied to feeder molecules.

A blocking moiety may be structured so that its effect on the feeder molecule may be removed upon the application of a stimulus. Any suitable stimulus may be applied, such as a change in the applied potential, means for breaking a bond or other attachment such as chemical or photo-cleavage and/or a means for changing the configuration or form of the blocking moiety. A blocking moiety may be structured so that its effect on the feeder molecule may be removed upon the application of a first stimulus and then re-applied upon the application of a second stimulus.

Figure 8:
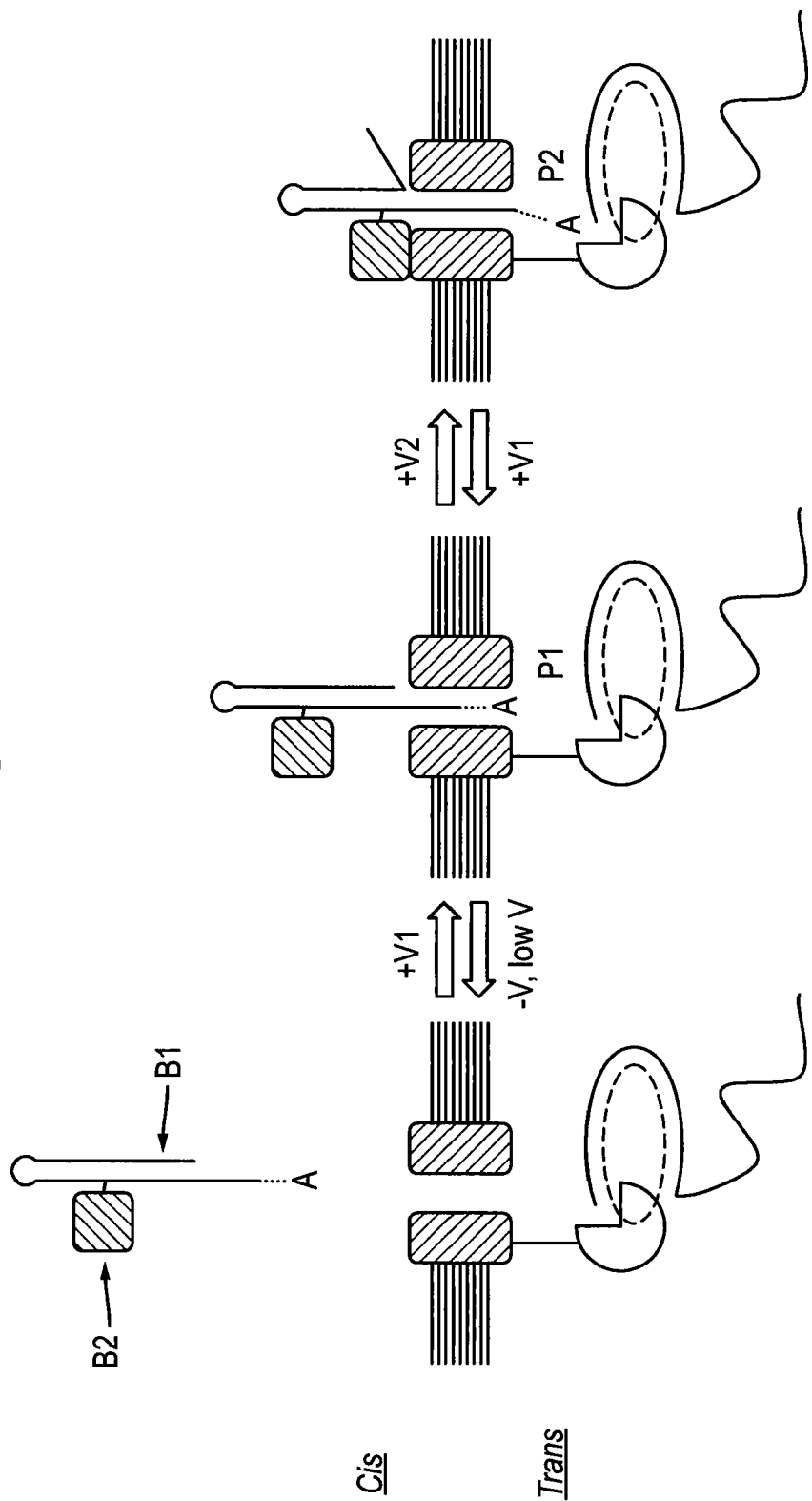
FIG. 8 provides a depiction of blocking moieties applied to feeder molecules.

With reference to FIG. 8, merely by way of illustration, first and second blocking moieties B1 (double-stranded region) and B2 (attached protein) may each be provided to the feeder molecule. When the feeder molecule moves, under the action of an applied potential V1 to a first position in a nanopore, the effect of the blocking moiety B1 may be to arrest or slow the movement of the feeder molecule such that it is held in the nanopore under application of V1 with the transfer nucleotide at positon P1. In such a situation the force of the ion current flowing through the nanopore under V1 is insufficient to overcome the strength of the hydrogen bonds comprising the double-stranded region of B1 and the transfer nucleotide remains at positon P1. Upon an increase in the applied voltage to V2, the strength of the ionic current increases and is able to overcome the strength of the hydrogen bonds comprising the double-stranded region of the blocking moiety B1, whereupon the strands of the double-stranded region of B1 separate. The feeder molecule or portion is able to move further into the nanopore in the trans direction until the effect of the blocking moiety B2 arrests the movement of the feeder molecule such that it is held in the nanopore under application of V2 with the transfer nucleotide at positon P2. P2 may define a desired position for the feeder molecule, such as a position in the nanopore whereby the attached transfer nucleotide may contact the enzyme. By returning the voltage back to V1 the feeder molecule is moved back in the nanopore in the cis direction and the nucleic acid strands re-hybridise to re-form the double-stranded region of blocking moiety B1 whereupon the feeder molecule is returned to position P1. By applying a reverse applied potential −V the feeder molecule may be ejected from the nanopore and returned to the cis side of the substrate.

Figure 9:
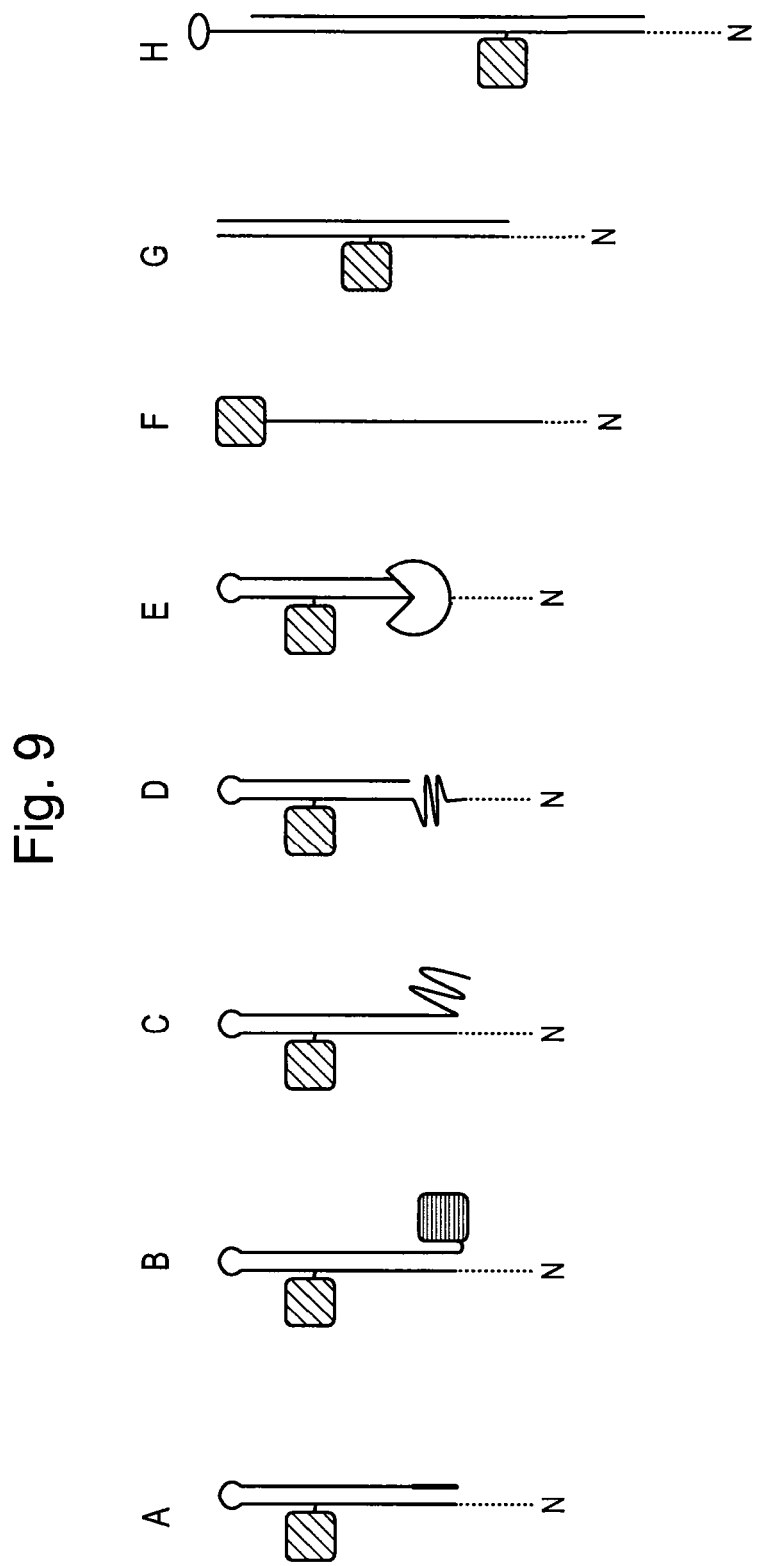
FIG. 9 shows some exemplary arrangements of blocking moieties provided to feeder molecules.
Figure 10:
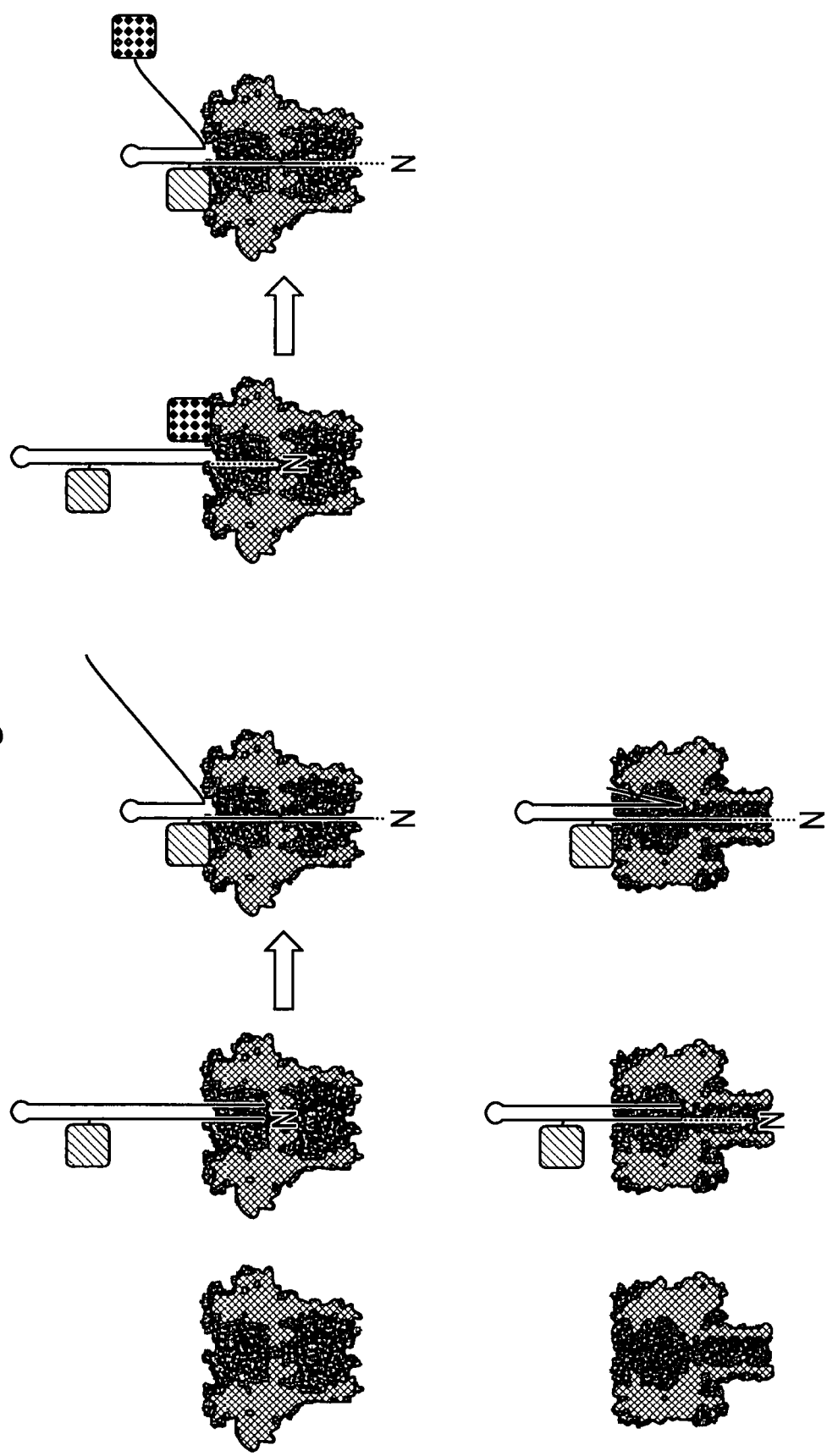
FIG. 10 depicts the requirement to tailor the design of feeder molecules depending upon the dimensions of the nanopore.

The nature of, type of and number of blocking moieties applied, as well as the positioning of the one or more blocking moieties along the length of the feeder molecule may depend upon the particular conditions and circumstances in which the feeder molecule is expected to function. For instance, the rate of translocation of a feeder molecule in a nanopore may be influenced by a variety of variable factors, such as the type of and structural arrangement of the feeder molecule itself, the type of nanopore to be used, the diameter of the channel of the nanopore through which the feeder molecule or portion thereof will move, whether or not a feeder molecule handling moiety and/or adaptor is used in conjunction with the nanopore, the size and polarity of the applied voltage, concentration of ions in the reaction solution and the type of substrate. Thus depending on the particular pattern of movement which is desired for the feeder molecule, the arrangement of the one or more blocking moieties along the length of the feeder molecule may be tailored in a bespoke fashion. For instance, in the illustrative example described above, the composition of nucleotides in B1 and the position and size of B2 may be adjusted so as to "tune" the feeder molecule for use and application in a given circumstance. Some exemplary arrangements of blocking moieties provided to feeder molecules are shown in FIG. 9. FIG. 10 depicts the requirement to tailor the design of feeder molecules depending upon the dimensions of the nanopore.

Tethering Moieties

A feeder molecule may optionally comprise a feeder molecule tethering moiety. A feeder molecule tethering moiety may be provided e.g. preferably wherein the substrate is a biological substrate, particularly a membrane, e.g. comprising an amphiphilic layer, for example a lipid layer or bilayer.

A feeder molecule tethering moiety reversibly tethers the feeder molecule to the substrate prior to capture and translocation into the nanopore. Application of a feeder molecule tethering moiety has several advantages. It can concentrate the feeder molecules in proximity to the nanopore, reducing the amount of feeder molecule which may need to be provided to synthesise a given polynucleotide molecule, and it can lead to a faster rate of capture by the nanopore.

A feeder molecule tethering moiety is preferably a hydrophobic molecule capable of coupling with a membrane as described and defined herein. For instance, the feeder molecule tethering moiety may be capable of binding to the membrane or incorporating into the membrane. Provided that the required function is performed, a feeder molecule tethering moiety may be any suitable moiety. A feeder molecule tethering moiety may for example comprise a lipid molecule, optionally a sterol molecule such as cholesterol.

A feeder molecule tethering moiety may be incorporated into a feeder molecule as part of its structure. A feeder molecule tethering moiety may be attached to a feeder molecule or to a blocking moiety which blocking moiety is attached to the feeder molecule. A feeder molecule tethering moiety may be attached at any suitable position on the feeder molecule or blocking moiety provided that the functions of all components as described herein are maintained.

A feeder molecule tethering moiety may optionally be attached to a feeder molecule or to a blocking moiety in such a way that the feeder molecule tethering moiety is removable from the feeder molecule or blocking moiety, for example upon application of a stimulus. For example the feeder molecule tethering moiety may be attached to the feeder molecule or blocking moiety with a linker or other suitable attachment group such that as the feeder molecule is moved into and through the nanopore, e.g. under the influence of an applied potential, the feeder molecule tethering moiety is removed or stripped away from the feeder molecule or blocking moiety. Removal of the or blocking moiety in this way may be permanent.

Figure 11:
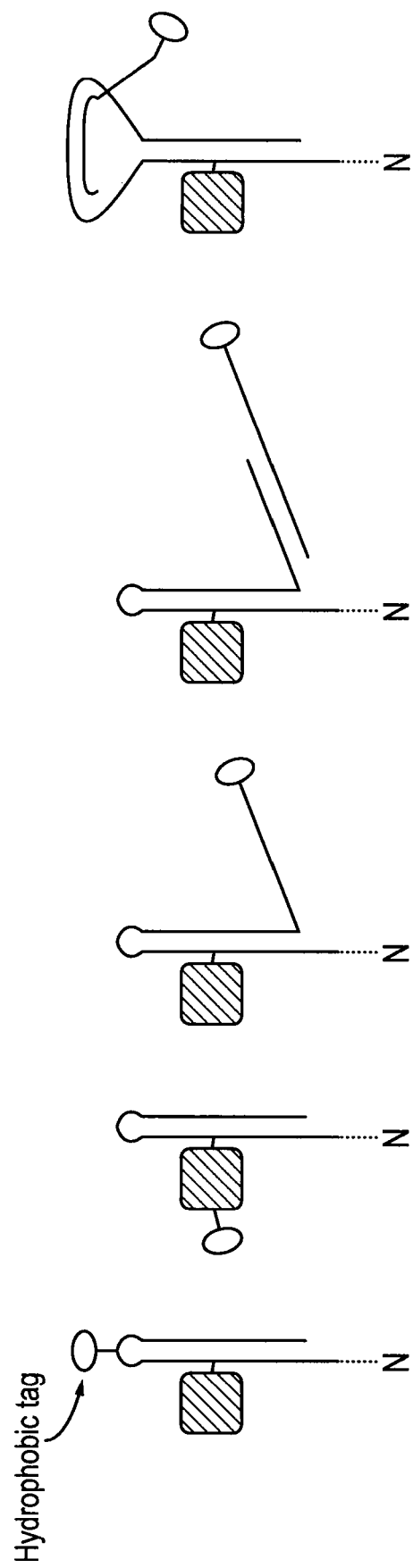
FIG. 11 depicts some example arrangements for feeder molecule tethering moieties.

Some example arrangements for feeder molecule tethering moieties are depicted in FIG. 11 merely by way of illustration.

Any suitable attachment methods described herein in the section "Linkers and attachment moieties" may be applied mutatis mutandis for the purposes of attaching a feeder molecule tethering moiety to a feeder molecule or to a blocking moiety.

In addition to the disclosure as provided herein, a feeder molecule tethering moiety may be attached by any of the suitable means disclosed in e.g. WO2010/086603, WO2010/004273, WO2010/004265 and/or WO 2012/033524.

Verification Processes

Some preferable embodiments of the methods of the invention involve a determination of the identity and/or integrity of the transfer nucleotide e.g. attached to a given feeder molecule prior to the step of contacting the transfer nucleotide with the enzyme.

Some preferable embodiments of the methods of the invention involve a determination as to whether or not the transfer nucleotide remains attached to a given feeder molecule subsequent to the step of contacting the transfer nucleotide with the enzyme.

Some preferable embodiments of the methods of the invention involve a combination of these determinations.

Determination of the presence and/or identity and/or integrity of the transfer nucleotide e.g. attached to a given feeder molecule may be achieved by utilising the same technology that has been established to determine the identity of units of a charged polymer translocating through a nanopore under the action of an applied potential.

As discussed herein, a determination of the identity of a polymer unit may be achieved by measuring a property with respect to the nanopore as the unit passes through the nanopore. In particular, such determination may be achieved by measuring the extent to which a polymer unit alters or perturbs the ionic current flowing through the nanopore under the action of an applied potential. The ionic current flowing through the nanopore which is measured is driven by the same applied potential that is responsible for moving/translocating the polymer, i.e. feeder molecule, through or across the nanopore.

When the transfer nucleotide passes through the pore or near its aperture, this event creates a disruption in the ionic current flow. A given transfer nucleotide optionally attached to a feeder molecule will create a disruption in the ionic current flow which is characteristic of and can uniquely identify that given nucleotide. By measuring these ionic current disruptions, different nucleotides can be distinguished. For example, the disruption or change in the ionic current flow associated with the movement in the nanopore of a nucleotide comprising an adenine nucleobase will be different from the disruption or change in the ionic current flow associated with the movement of a nucleotide comprising a thymine nucleobase. Measurements of ionic current flow characteristics provides a basis for performing verification processes e.g. to determine whether a given feeder molecule within a nanopore is attached to the desired transfer nucleotide. If not, the applied potential may be reversed and the transfer nucleotide, or feeder molecule comprising the attached transfer nucleotide, can be ejected from the nanopore before the transfer nucleotide has contacted the enzyme, and thus before the enzyme has been able to catalyse the extension of the polynucleotide synthesis molecule. The reverse applied potential may be applied for a sufficient period of time to eject the transfer nucleotide or feeder molecule comprising the attached transfer nucleotide from the nanopore, whereupon the initial applied potential may be re-applied so as to draw a different transfer nucleotide or feeder molecule comprising the attached transfer nucleotide into the nanopore. The verification process can then be repeated until the desired transfer nucleotide is captured within a nanopore or until a feeder molecule is captured within a nanopore having the desired transfer nucleotide attached.

Determining the Identity and/or Integrity of a Nucleotide within a Nanopore

Typically in methods of the invention, populations of feeder molecules will be provided on the cis side of the substrate, typically each population respectively comprising feeder molecules having attached nucleotides comprising desired nucleobases to be incorporated into the polynucleotide synthesis molecule. The feeder molecules may be provided as a single heterogenous mixture, all in solution on the cis side of the substrate. In order to extend the polynucleotide synthesis molecule with a transfer nucleotide it is necessary to contact the enzyme with a feeder molecule having the desired transfer nucleotide. Where a given feeder molecule is moved into a nanopore on a random basis from a single heterogenous mixture of feeder molecules, it is desirable to identify, via a verification process, whether the feeder molecule is attached to the desired transfer nucleotide. If the feeder molecule is determined to be attached to the desired transfer nucleotide, it may be allowed to move further through the nanopore such that the transfer nucleotide contacts the enzyme. If the feeder molecule is determined to be attached to a nucleotide which is not the desired transfer nucleotide, it may be moved back through the nanopore towards the cis side of the substrate and returned to the cis side before the nucleotide is contacted with the enzyme, i.e. ejected from the nanopore and back to the cis side of the substrate. Such a process may be repeated until a feeder molecule is provided in the nanopore having the desired transfer nucleotide attached. Only then is the feeder molecule moved further through the nanopore to a position whereby the transfer nucleotide is contacted with the enzyme.

The integrity of the nucleotide attached to the feeder molecule may also be determined using such a process. For example, it is desirable to determine whether the nucleotide attached to the feeder molecule is defective in some way, such as by having a damaged or structurally altered sugar group or nucleobase. Thus the methods described and defined herein may comprise verification processes to determine the integrity of the nucleotide, such as whether the nucleotide comprises the desired structure.

Thus in any of the methods of the invention a first verification process may be performed as the feeder molecule is moved through the nanopore to determine the identity and/or integrity of the transfer nucleotide of the feeder molecule, wherein:

a) if the feeder molecule is determined to have the desired transfer nucleotide attached, moving the feeder molecule to bring the transfer nucleotide into contact with the enzyme; or
b) if the feeder molecule is determined not to have the desired transfer nucleotide attached:
  i. moving the feeder molecule back to the cis side of the substrate;
  ii. moving a feeder molecule from the mixture of feeder molecules at the cis side of the substrate into the nanopore towards the trans side; and
  iii. repeating the first verification process until the feeder molecule is determined to have the desired transfer nucleotide attached, following which the feeder molecule is moved to bring the transfer nucleotide into contact with the enzyme.

The identity and/or integrity of the nucleobase of the nucleotide attached to the feeder molecule may be determined by performing a measurement of the feeder molecule. A feeder molecule may give rise to an identifiable signal to uniquely identify the attached transfer nucleotide and/or to determine the integrity of the attached transfer nucleotide.

Measurement of the feeder molecule may be with respect to the nanopore. For example, the identity of the nucleobases adenine, thymine, cytosine, guanine and uracil may be distinguished from each other by measuring the perturbations in ionic current flowing through the nanopore in the presence of the feeder molecule under an applied potential as described herein.

Thus in any of the methods of the invention the identity and/or integrity of the nucleobase attached to a feeder molecule may be established by measuring the ion current flow through the nanopore under an applied potential.

A verification process wherein the feeder molecule is determined to have the desired transfer nucleotide attached may also be performed by detecting the presence or absence of the desired transfer nucleotide using polynucleotide sequence identification motifs (barcodes) incorporated into feeder molecules. For example, by providing each one of the four populations of feeder molecules with a separate polynucleotide sequence identification motif (barcode), it is possible to sequence the barcode as the feeder molecule is moved through the nanopore. Again, the detection technology described herein involving measuring perturbations of ion current flow through the nanopore under an applied potential may be used to determine the sequence of the barcode.

The same principles of detection and verification of transfer nucleotides within nanopores described above may also be applied to methods disclosed herein which relate to movement of transfer nucleotides which are free transfer nucleotides unattached to feeder molecules.

Determining the Presence or Absence of a Nucleotide Attached to a Feeder Molecule Any of the methods of the invention involving feeder molecules may further comprise a second verification process performed to verify that the enzyme has catalysed the transfer of the transfer nucleotide from the feeder molecule to the polynucleotide synthesis molecule. For example, the feeder molecule may be moved through the nanopore to a position in the nanopore such that it is expected that the transfer nucleotide attached to the feeder molecule will contact the enzyme. Notwithstanding this, the enzyme might for some reason fail to catalyse the transfer of the nucleotide to the polynucleotide synthesis molecule. Before proceeding from a first extension cycle to a second extension cycle, it may be desired to establish whether the polynucleotide synthesis molecule has been extended with the transfer nucleotide in the first extension cycle.

Thus in any of the methods of the invention involving feeder molecules, before moving the feeder molecule to the cis side of the substrate following an assumed transfer of the transfer nucleotide to the polynucleotide synthesis molecule a second verification process may be performed to verify that the enzyme has in fact catalysed the transfer of the transfer nucleotide from the feeder molecule to the synthesis molecule. The second verification process may comprise the steps of:
  i. moving the feeder molecule through the nanopore in the cis direction, and determining the presence or absence of the nucleobase of the attached transfer nucleotide,
  ii. moving the feeder molecule back in the trans direction to bring the nucleotide into contact with the enzyme if the nucleobase of the attached transfer nucleotide is determined to be attached to the feeder molecule; and
  iii. repeating steps (i) and (ii) until the desired transfer nucleotide is determined to have been removed from the feeder molecule.

The step of determining the presence or absence of the nucleobase of the attached transfer nucleotide whilst moving the feeder molecule through the nanopore in the cis direction may be determined by performing a measurement of the feeder molecule, as in the first verification process. A feeder molecule may give rise to an identifiable signal to identify whether or not the transfer nucleotide is attached to the feeder molecule.

As with the first verification process, measurement of the feeder molecule may be with respect to the nanopore. For example, the presence or absence of the nucleobase on the feeder molecule may be established using the detection technology described herein, involving measuring perturbations in the ion current flow through the nanopore under an applied potential when the feeder molecule is positioned within the nanopore.

The second verification process may comprise a measurement comparison performed in conjunction with a first verification process. In such a comparison a first verification process, as described above, is performed to establish the identity, and optionally the integrity, of the transfer nucleotide whilst moving the feeder molecule through the nanopore in the cis direction before the transfer nucleotide is contacted with the enzyme, thus obtaining a first measurement corresponding to the desired transfer nucleotide when attached to the feeder molecule. A second measurement of the same feeder molecule is obtained during the step of determining the presence or absence of the nucleobase of the attached transfer nucleotide whilst moving the feeder molecule back through the nanopore in the cis direction. The first and second measurements are then compared to determine a change in the measurements which may provide an indication that the transfer nucleotide has been removed from the feeder molecule, i.e. by the action of the enzyme. An example of such a method scheme is depicted, merely by way of illustration, in FIG. 12.

Feeder Molecule Handling Moieties

In the methods of the present invention, extension processes may involve the translocation of a feeder molecule through a nanopore. As described in detail herein, a feeder molecule may be comprised of a molecule comprising a polymer. In the methods of the invention the feeder molecule may be provided on the cis side of the substrate such that a change in the form of the feeder molecule is required in order that the feeder molecule, or a desired portion of the feeder molecule, may be translocated into and through the nanopore. Thus it may be necessary to process the feeder molecule as it is translocated into and through the nanopore. Many moieties are available which are capable of processing a polymer, such as a double-stranded nucleic acid, and guiding a portion of the polymer through a nanopore and controlling the movement and translocation of such a portion of a polymer through a nanopore. Such a moiety is referred to herein as a feeder molecule handling moiety. Typically the handling moiety can move the feeder molecule through the nanopore with or against an applied field. The handling moiety can be a molecular motor using, for example, in the case where the moiety is an enzyme, enzymatic activity.

A feeder molecule handling moiety may for example act as a "brake" to slow the movement of a feeder molecule as it translocates through a nanopore. A feeder molecule handling moiety may desirably be provided associated with a nanopore to aid in a variety of functions. For example, it may be desirable to control the movement of a feeder molecule as it translocates through a nanopore from a first to one or more second positions in the nanopore, for example when performing a verification process as described herein.

A feeder molecule handling moiety may be a polypeptide that is capable of interacting with and modifying at least one property of the feeder molecule. The handling moiety may modify the feeder molecule by orientating it or moving it to a specific position. The handling moiety does not need to display enzymatic activity as long as it is capable of binding the target feeder molecule and controlling its movement through the nanopore. For instance, the handling moiety may be modified to remove its enzymatic activity or may be used under conditions which prevent it from acting as an enzyme.

Thus in any of the methods of the invention the nanopore may be provided associated with a feeder molecule handling moiety provided adjacent the nanopore, and most preferably provided on the cis side of the substrate adjacent the nanopore.

In a preferred embodiment the feeder molecule is comprised of a molecule comprising a nucleic acid, in which case the feeder molecule handling moiety may be referred to as a nucleic acid handling moiety. A nucleic acid handling moiety may also be referred to as a nucleic acid handling enzyme, a nucleic acid binding protein/enzyme or a processive enzyme. Nucleic acid handling moieties or processive enzymes are known, and have been described and characterised for use in guiding nucleic acid molecules and other polymers through nanopores and to control the movement and translocation of such molecules and other polymers through nanopores (e.g. WO2010/086603, WO2010/004273, WO2010/004265 and WO 2012/033524).

Many nucleic acid handling enzymes are suitable for use in this application provided they hydrolyse, polymerise or process polynucleotide molecules to form single stranded species. Preferred enzymes are polymerases, nucleases, helicases, single-stranded and double-stranded binding proteins and topoisomerases, such as gyrases.

One advantageous mechanism for use in an extension process of the invention is the controlled translocation of a single-stranded nucleic acid portion of a feeder molecule through a nanopore, in either the cis to trans or trans to cis direction, under the action of an applied potential. Exonucleases that act progressively or processively on double-stranded nucleic acid, such as DNA, can be used on the cis side of the substrate to move the remaining single strand through the nanopore in the cis to trans direction under an applied potential, or in the trans to cis direction under a reverse potential. Likewise, a helicase that unwinds a double-stranded nucleic acid can also be used in a similar manner. There are also possibilities for applications that require feeder molecule translocation against an applied potential, but the feeder molecule must be first "caught" by the handling moiety under a reverse or no potential. With the potential then switched back following binding the feeder molecule will move in the cis to trans direction through the nanopore and will be held in an extended conformation by the current flow. The single strand nucleic acid exonucleases or single strand nucleic acid dependent polymerases can act as molecular motors to pull the recently translocated single strand back through the nanopore in a controlled manner, trans to cis, against the applied potential.

A particularly preferred mechanism for performing the methods of the invention is to move a feeder molecule through a nanopore to bring the attached transfer nucleotide into contact with the enzyme, wherein the feeder molecule comprises a portion of a single stranded polymer as described herein, such as a nucleic acid, PNA etc., and wherein the portion of the feeder molecule which is moved (translocated) through or across the nanopore comprises a single stranded portion. The transfer nucleotide may be attached to the feeder molecule at the terminal end of the single stranded portion of the feeder molecule, or at a position along the length of the single stranded portion of the feeder molecule. Any moieties, techniques or enzymes described in WO2012/107778 or WO2012/033524 could be used to control the movement of the feeder molecule through the nanopore in this way.

Thus any of the methods of the invention comprise an extension process comprising providing a feeder molecule at the cis side of a substrate comprising a nanopore, the feeder molecule having an attached transfer nucleotide, and wherein the nanopore is provided with a feeder molecule handling moiety coupled to the nanopore, and wherein the process comprises contacting the feeder molecule with the feeder molecule handling moiety and moving the feeder molecule through the nanopore. The feeder molecule handling moiety may be a nucleic acid handling moiety such as a polymerase, a nuclease, a helicase or a topoisomerase such as a gyrase. The feeder molecule handling moiety may be a nucleic acid handling moiety comprising a phi29 DNA polymerase, a T7 DNA polymerase, a His 1 DNA polymerase, a His 2 DNA polymerase, a *bacillus* phage M2 DNA polymerase, a *streptococcus* phage CPI DNA polymerase, an *enterobacter* phage PRD1 DNA polymerase, or any variant thereof. The feeder molecule handling moiety may be any disclosed in WO2010/086603, WO2012/107778, WO2010/004273, WO2010/004265, WO 2012/033524 and Lieberman K et al, (J Am Chem Soc., 2010, 132(50), pp 17961-17972), and for voltage gated schemes in Luan B et al., (Phys Rev Lett., 2010, 104(23), 238103).

The handling moiety may be derived from a nucleolytic enzyme. The handling moiety may be derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31.

Other suitable enzymes for use as handling moieties include, but are not limited to, exonuclease I from *E. coli*, exonuclease III enzyme from *E. coli*, RecJ from *T. thermophilus* and bacteriophage lambda exonuclease and variants thereof. Examples of suitable such enzymes are disclosed in WO2016/059427. Three subunits of bacteriophage lambda exonuclease comprising the sequence shown in Seq ID: 8 in WO2016/059427 or a variant thereof interact to form a trimer exonuclease. The enzyme may be derived from a Phi29 DNA polymerase, such as an enzyme comprising the sequence shown in Seq ID: 9 in WO2016/059427 or a variant thereof.

A variant is an enzyme that has an amino acid sequence which varies from that of the original starting reference enzyme sequence and which retains polynucleotide binding ability. The variant may include modifications that facilitate binding of the polynucleotide and/or facilitate its activity at high salt concentrations and/or room temperature. Over the entire length of the amino acid sequence, a variant will preferably be at least 50% homologous to the original starting reference sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity over the entire sequence. There may be at least 80%, for example at least 85%, 90% or 95%, amino acid identity over a stretch of 200 or more, for example 230, 250, 270 or 280 or more, contiguous amino acids.

A feeder molecule handling moiety may comprise an enzyme selected from a bacterium from the group consisting of *Haloferax, Halogeometricum, Halococcus, Haloterrigena, Halorubrum, Haloarcula, Halobacterium, Salinivibrio costicola, Halomonas elongata, Halomonas israelensis, Salinibacter rube, Dunaliella salina, Staphylococcus aureus. Actinopolyspora halophila, Marinococcus halophilus,* and *S. costicola.*

Attachment of Feeder Molecule Handling Moieties to Substrates

A feeder molecule handling moiety such as nucleic acid handling moiety is typically attached to the substrate via one or more of its substrate accessible residues having side chains of a preferred orientation. Any of the preferred attachment residues may be modified by substitution. One or more of the preferred attachment residues may be substituted with cysteine. The moiety may be attached to the substrate via more than one residue.

The moiety may be attached to the substrate via one or more accessible cysteine residues. The moiety may be attached to the substrate at more than one, such as two or three, points. Attaching the moiety to the substrate at more than one point can be used to constrain the mobility of the moiety. For instance, multiple attachments may be used to constrain the freedom of the moiety to rotate or its ability to move away from the substrate.

The moiety may be attached to the substrate directly or indirectly. The moiety may be attached to the substrate via the nanopore, in which case the moiety may be attached directly to the nanopore.

The moiety may be attached to a subunit of an oligomeric nanopore. If the substrate is a subunit of an oligomeric nanopore, the subunit may be in a monomeric form when it is attached to the moiety (post expression modification). Alternatively, the subunit may be part of an oligomeric nanopore when it is attached to the moiety (post oligomerisation modification).

A feeder molecule handling moiety such as a nucleic acid handling moiety can be attached to the substrate using any method known in the art. The moiety and substrate may be produced separately and then attached together. If the substrate is itself a protein, such as a pore subunit, the two components may be attached in any configuration. For instance, they may be attached via their terminal (i.e. amino or carboxy terminal) amino acids. Suitable configurations include, but are not limited to, the amino terminus of the handling moiety being attached to the carboxy terminus of the substrate and vice versa. Alternatively, the two components may be attached via amino acids within their sequences. For instance, the moiety may be attached to one or more amino acids in a loop region of the substrate. In one embodiment, terminal amino acids of the handling moiety are attached to one or more amino acids in the loop region of the substrate.

The handling moiety may be chemically fused to the substrate. A handling moiety may be chemically fused to a substrate if the two parts are chemically attached, for instance via a linker molecule. Any method of chemical fusion or attachment can be used. Suitable methods include, but are not limited to, affinity interactions, histidine tag binding to a metal affinity matrix, Ni-NTA, biotin binding to streptavidin, antibody binding to an antigen, primary amine coupling, GST tag(s) binding to glutathione, MBP tag(s) binding to dextrin, Protein A binding to IgG, reaction between thiols, nucleic acid hybridisation linkers and cysteine linkage. The handling moiety may be covalently attached to the substrate.

If the substrate is a protein, the handling moiety may be genetically fused to the substrate. A handling moiety is genetically fused to a protein substrate if the whole construct is expressed from a single polynucleotide sequence. The coding sequences of the handling moiety and substrate may be combined in any way to form a single polynucleotide sequence encoding the construct.

The handling moiety and substrate may be genetically fused in any configuration, such as via their terminal amino acids. The amino acid sequence of the handling moiety may be added in frame into the amino acid sequence of the substrate. The handling moiety may be inserted into a loop region of a transmembrane protein pore or pore subunit.

A feeder molecule handling moiety, such as a nucleic acid handling moiety, retains its ability to bind nucleic acids. This ability is typically provided by its secondary structural elements ($\alpha$-helices and $\beta$-strands) and tertiary structural elements. In order to avoid adversely affecting the nucleic acid binding ability of the handling moiety, it is preferably attached to the substrate in a manner that does not affect its secondary or tertiary structure.

If the substrate is a pore or pore subunit, the pore or pore subunit retains its ability to form pores. The pore forming ability of subunits is typically provided by their $\alpha$-helices and $\beta$-strands. $\beta$-barrel pores comprise a barrel or channel that is formed from $\beta$-strands, whereas $\alpha$-helix bundle pores comprise a barrel or channel that is formed from $\alpha$-helices. The $\alpha$-helices and $\beta$-strands are typically connected by loop regions. In order to avoid affecting the pore forming ability of the subunit, the handling moiety is preferably attached to a loop region of the subunit.

The handling moiety may be attached directly to the substrate. For instance, native and/or non-native accessible cysteine residues can be attached directly to activated thiol-sepharose.

The handling moiety can be attached to the substrate at one or more positions, such as at one, two, three or four positions. The handling moiety is preferably attached to the substrate at one or two positions. After removal of native cysteine residues from the handling moiety, one or more cysteine residues can be incorporated into the moiety at specific positions for the attachments. Attachments can be done either by direct crosslinking of the cysteine residues in the handling moiety to cysteines in the substrate (i.e. via a disulphide bond) or by using crosslinkers. Attachment at two positions can reduce the flexibility of the complex and can fix the handling moiety on the substrate in a chosen specific orientation.

Exemplary constructs comprising a handling moiety and a nanopore are disclosed in WO2010/086603. Any of these constructs can be used in the methods of the present invention.

The handling moiety is preferably attached to the substrate using one or more, such as two or three, linkers. The one or more linkers may be designed to constrain the mobility of the handling moiety. The linkers are typically attached to the one or more accessible cysteine residues in the handling moiety. The linkers may be attached to one or more reactive groups, such as cysteine residues, reactive lysine residues or non-natural amino acids, in the substrate. Suitable linkers are well known in the art. Suitable linkers include, but are not limited to, chemical crosslinkers and peptide linkers. Chemical crosslinkers include nucleic acid hybridisation linkers. The length, flexibility and hydrophilicity of the nucleic acid hybridisation linkers are typically designed such that they do not to disturb the functions of the handling moiety and substrate. An advantage of using hybridisation linkers is that the formation of unwanted dimers (substrate-substrate or protein-protein) is minimized. The nucleic acid hybridisation linkers can comprise any of the nucleic acids discussed herein. For instance, they may comprise deoxyribonucleic acid (DNA), ribonucleic acid (RNA) or any synthetic nucleic acid known in the art, including those described herein such as peptide nucleic acid (PNA), glycerol nucleic acid (GNA), threose nucleic acid (TNA), locked nucleic acid (LNA) or other synthetic polymers with nucleotide side chains. The linkers can also be modified such they react with one another once they have hybridised. Alternatively, agents may be used to crosslink the linkers once they have hybridised to one another.

Exemplary nucleic acid hybridisation linkers are disclosed in WO2010/086603. For example, nucleic acid hybridisation linkers may correspond to the first 15, 25 or 35 nucleotides from the 5' end of SEQ ID NO: 57 as disclosed in WO2010/086603. The linker may also have TT at the 3' end to provide extra flexibility. At the 3' end, the linkers may have a group, such as maleimide or thiol, that allows the linker to be attached to the handling moiety or substrate. Maleimide or thiol modified oligonucleotides can be obtained commercially, for instance from ATDBio. More linkers are shown in SEQ ID NOs: 58, 59 and 60 of WO2010/086603. Complementary linkers are shown in SEQ ID NOs: 61, 62 and 63 of WO2010/086603. SEQ ID NO: 58, 59 or 60 of WO2010/086603 may be attached to one of the handling moiety and substrate and the complementary linker (SEQ ID NO: 61, 62 or 63 respectively) may be attached to the other of the handling moiety and substrate. The handling moiety and substrate can then be attached together by hybridising the linkers.

The stability of the hybridisation depends on the melting temperature of the hybridising linkers. Depending on the application and the required stability, this can be optimized by changing the sequences of the linkers (e.g. changing the linkers to more GC rich will increase their melting temperature and hence the stability), the length of the linkers (i.e. increasing their length will increase the stability) or the reaction conditions (e.g. increasing their concentration will increase the stability).

For maximum stability of hybridisation, it is desirable to have long hybrising linkers with high melting temperatures, for example linkers more than 15 nucleotides in length, particularly 15 to 45 nucleotides in length, such as 15, 20, 25, 30, 35, 40 or 45 nucleotides in length. However, the use of long linkers increases the distance between the moieties. This may be disadvantageous because interaction between the moieties is disrupted or because proximity is required for the substrate to detect a substrate which has been released from the handling moiety. Increased distance may be advantageous as it may prevent aggregation or electrostatic interactions and may permit flexing. The disadvantages of the increased distance can be overcome by changing the orientation of the nucleic acid attachment. Preferably, the linkers comprise a nucleic acid that is from 6 to 15 nucleotides in length, such as 6, 8 or 10 nucleotides long.

The hybridisation linkers preferably have an affinity of from 1 fM to 1 uM at concentrations of from 1 pM to 1 mM. The linkers more preferably have an affinity of from 1 fM to 10 nM at concentrations of from 1 pM to 1 uM. The linkers most preferably have an affinity of from 1 pM to 100 pM at concentrations of from 100 pM to 10 nM.

An exemplary linker is shown in SEQ ID NO: 64 of WO2010/086603. The 3' end of this linker can be attached to a cysteine residue on the substrate. The linker preferably also has TTTTT at the 3' end to provide extra flexibility. The 5' end of SEQ ID NO: 65 of WO2010/086603 can then be attached to the handling moiety. In this example, the 3' end of the SEQ ID NO 64 is complementary to a stretch of sequence at the 5' end of SEQ ID NO: 65.

Once the linkers are hybridised to each other, they melt (fall apart) under certain conditions (for example, at high temperatures or lower salt conditions) unless there is a permanent bond between the two linkers. To form a permanent bond, the linkers are preferably modified such they react with one another once they have hybridised. Each linker may contain a group capable of forming a covalent bond with a group in another linker. A pair of linkers can be linked by one or more covalent bonds, for example one, two or three, covalent bonds.

Typically the bond will be a simple disulfide bond between the two linkers. The linkers can also be modified to incorporate thiol groups at one or more, such as two, positions. Depending on the application and preferences, thiols groups can be internal or terminal.

Linkers can also be modified either internally or terminally to include one or more, such as two, iodoacetamide groups. A hybridising linker with one or more iodoacetamide groups can be covalently linked to thiols on the complementary hybridising linker.

Linkers can also be modified with alkene groups. One or more internal or terminal alkene groups in preferred positions can be subjected to olefin metathesis to make a covalent bond between the alkenes in the hybridisation linkers.

If necessary, a small linker can be added between the linker and the reactive groups, such as thiol groups, iodoacetamide groups and alkene groups, to obtain the proper distances necessary to make an efficient covalent bond between the linkers.

In a preferred embodiment, the covalent bond between the linkers can be made using "click chemistry" techniques. Click chemistry is a term first introduced by Kolb et al. in 2001 to describe an expanding set of powerful, selective, and modular building blocks that work reliably in both small- and large-scale applications (Kolb H C, Finn, M G, Sharpless K B, Click chemistry: diverse chemical function from a few good reactions, Angew. Chem. Int. Ed. 40 (2001) 2004-2021). They have defined a set of stringent criteria for click chemistry as follows: "The reaction must be modular, wide in scope, give very high yields, generate only inoffensive byproducts that can be removed by nonchromatographic methods, and be stereospecific (but not necessarily enantioselective). The required process characteristics include simple reaction conditions (ideally, the process should be insensitive to oxygen and water), readily available starting materials and reagents, the use of no solvent or a solvent that is benign (such as water) or easily removed, and simple product isolation. Purification if required must be by nonchromatographic methods, such as crystallization or distillation, and the product must be stable under physiological conditions".

Suitable examples of click chemistry include, but are not limited to, the following:
(a) copper-free variant of the 1,3 dipolar cycloaddition reaction, where an azide reacts with an alkyne under strain, for example in a cyclooctane ring;
(b) the reaction of an oxygen nucleophile on one linker with an epoxide or aziridine reactive moiety on the other; and
(c) the Staudinger ligation, where the alkyne moiety can be replaced by an aryl phosphine, resulting in a specific reaction with the azide to give an amide bond.

Preferably the click chemistry reaction is the Cu (I) catalysed 1,3 dipolar cycloaddition reaction between an alkyne and an azide. Nucleic acid bases have already been synthesised incorporating azide and alkyne groups in preferred positions (for example Kocalka P, El-Sagheer A H, Brown T, Rapid and efficient DNA strand crosslinking by click chemistry, Chembiochem. 2008. 9(8):1280-5).

If nucleotides within the linkers' nucleic acid regions are modified to include groups that can form covalent bonds, the modified nucleotides are preferably offset from one another by one nucleotide in order to achieve the link. This follows the published work of Tom Brown (Kocalka et al. (2008) ChemBiochem 9, 8, 1280-1285).

In one embodiment, a single azide group (e.g. SEQ ID NO: 66 of WO2010/086603) or more, such as two (SEQ ID NO: 67 of WO2010/086603), can be incorporated into uracil bases at specific places in a 15 base deoxyribonucleic acid sequence. The cysteine residues on the substrate can then be modified with these azide hybridisation linkers using the thiol group at the 5'end (SEQ ID NOs: 66 and 67). Alkyne groups can also be incorporated into uracil bases at preferred positions in sequences complementary to the SEQ ID NOs: 66 and 67 (SEQ ID NOs: 68 and 69 of WO2010/086603 respectively). These sequences can be used to modify the cysteines on the handling moiety. Using DNA hybridisation followed by 'click chemistry' between the azide and alkyne groups, hybridisation linkers can be covalently crosslinked.

The distance between the substrate and the handling moiety can be modulated by changing the length of the hybridisation linkers. The position of the azide and alkyne modified bases then needs to be changed accordingly.

In one embodiment 6 mer (SEQ ID NO 70 of WO2010/086603), 8 mer (SEQ ID NO 71 of WO2010/086603) or 10 mer (SEQ ID NO 72 of WO2010/086603) DNA in which two uracil bases are modified with azide groups can be attached to the cysteines of the moiety. Complementary sequences of 6 mer (SEQ ID NO 73 of WO2010/086603), 8 mer (SEQ ID NO 74 of WO2010/086603) or 10 mer (SEQ ID NO 75 of WO2010/086603) DNA in which two uracil bases are modified with alkyne groups can be attached to the cysteines of a moiety such as a DNA binding protein. Covalent crosslinking between these hybridisation linkers will bring the moieties closer to each other than with the hybridisation linkers (SEQ ID NO 67 and 69 of WO2010/086603). Incorporation of azide and alkyne groups into uracil base units of DNA has been developed by ATDBio.

Other examples of chemical linkers are shown in the following table.

| Name | Reacts with | Structure |
|---|---|---|
| 1,4-Bis[3-(2-pyridyldithio)propionamido]butane | Thiols | 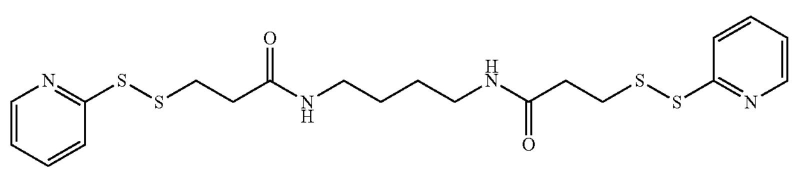 [SMILES: O=C(CCSSc1ccccn1)NCCCCNC(=O)CCSSc1ccccn1] |
| 1,11-bis-Maleimidotriethyleneglycol | Thiols | |
| 3,3'-Dithiodipropionic acid di(N-hydroxysuccinimide ester) | Primary amines | 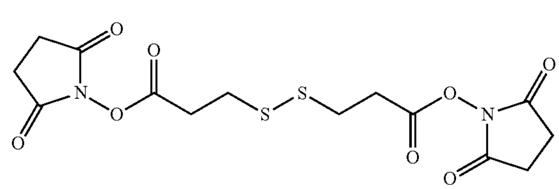 [SMILES: O=C(CCSSCCC(=O)ON1C(=O)CCC1=O)ON1C(=O)CCC1=O] |

-continued

| Name | Reacts with | Structure |
|---|---|---|
| Ethylene glycol-bis(succinic acid N-hydroxysuccinimide ester) | Primary amines | 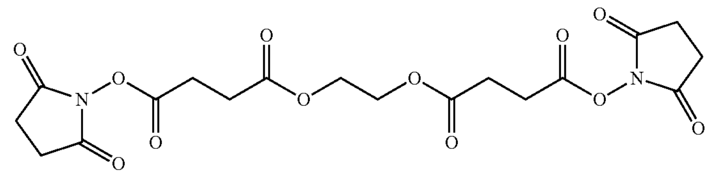 [SMILES: O=C(CCC(=O)ON1C(=O)CCC1=O)OCCOC(=O)CCC(=O)ON1C(=O)CCC1=O] |
| 4,4'-Diisothiocyanatostilbene-2,2'-disulfonic acid disodium salt | Primary amines | 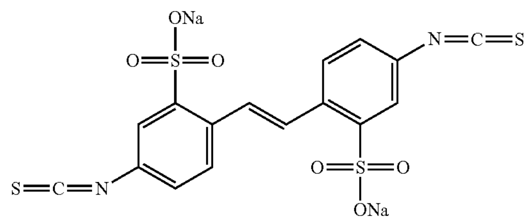 |
| Bis[2-(4-azidosalicylamido)ethyl] disulfide | Photo-activated, non-specific | 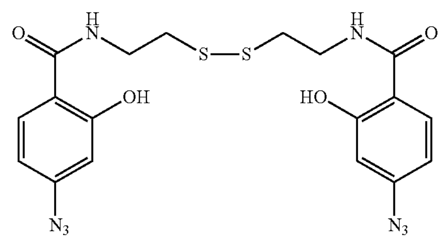 [SMILES: [N-]=[N+]=Nc1ccc(C(=O)NCCSSCCNC(=O)c2ccc(N=[N+]=[N-])cc2O)c(O)c1] |
| 3-(2-Pyridyldithio)propionic acid N-hydroxysuccinimide ester | Thiols, primary amines | 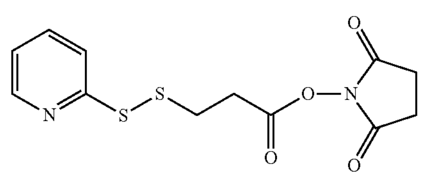 [SMILES: O=C(CCSSc1ccccn1)ON1C(=O)CCC1=O] |
| 4-Maleimidobutyric acid N-hydroxysuccinimide ester | Thiols, primary amines | 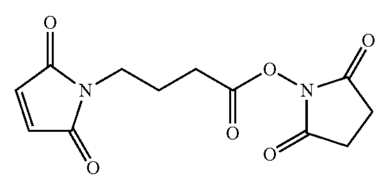 [SMILES: O=C(CCCN1C(=O)C=CC1=O)ON1C(=O)CCC1=O] |
| Iodoacetic acid N-hydroxysuccinimide ester | Thiols, primary amines | 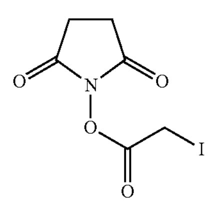 [SMILES: O=C(CI)ON1C(=O)CCC1=O] |
| S-Acetylthioglycolic acid N-hydroxysuccinimide ester | Thiols, primary amines | 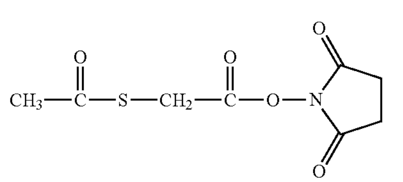 |
| Azide-PEG-maleimide | Thiols, alkyne | 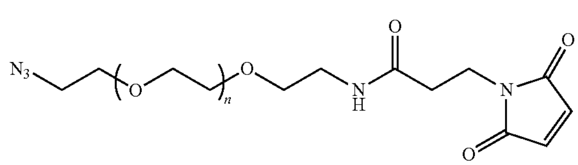 |

$n = 5, 10$

| Name | Reacts with | Structure |
|---|---|---|
| Alkyne-PEG-maleimide | Thiols, azide | 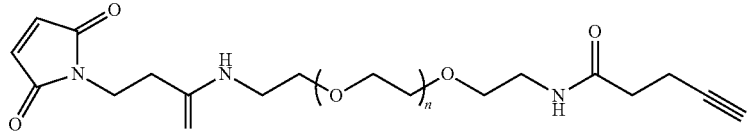<br>$n = 6, 10$ |

Linkers may be attached to the handling moiety first and then the substrate, the substrate first and then the handling moiety or the substrate and handling moiety at the same time. When the linker is attached to a pore subunit (as the substrate), it may be a monomeric subunit, part of an oligomer of two or more monomers or part of complete oligomeric pore. It is preferred that the linker is reacted before any purification step to remove any unbound linker.

One method of attaching the handling moiety to the substrate is via cysteine linkage. This can be mediated by a bi-functional chemical linker or by a polypeptide linker with a terminal presented cysteine residue. α-HL (SEQ ID NO: 2 of WO2010/086603) lacks native cysteine residues so the introduction of a cysteine into the sequence of SEQ ID NO: 2 enables the controlled covalent attachment of the handling moiety to the subunit. Cysteines can be introduced at various positions, such as position K8, T9, N17 or E287 of SEQ ID NO: 2 or at the carboxy terminus of SEQ ID NO: 2. The length, reactivity, specificity, rigidity and solubility of any bi-functional linker may be designed to ensure that the enzyme is positioned correctly in relation to the subunit and the function of both the subunit and enzyme is retained. Suitable linkers include those described above.

Crosslinkage of subunits or enzymes to themselves may be prevented by keeping the concentration of linker in a vast excess of the handling moiety and/or the substrate. Alternatively, a "lock and key" arrangement may be used in which two linkers are used. For instance, click chemistry, such as azide alkyne Huisgen cycloaddition, may be used to ensure that the handling moiety only binds to the substrate and not to itself and vice versa. In one embodiment, the azide-PEG-maleimide and alkyne-PEG-maleimide linkers shown in the table above may be used. One is attached to the handling moiety and the other is attached to the substrate. This ensures that binding only occurs between the handling moiety and the substrate.

Only one end of each linker may react together to form a longer linker and the other ends of the linker each react with a different part of the substrate (i.e. subunit or monomer).

The site and method of covalent attachment is preferably selected such that mobility of the handling moiety is constrained. This helps to ensure that the handling moiety handles the target nucleic acid sequence in such a way that a proportion of the nucleotides in the target sequence interacts with the pore. For instance, constraining the ability of a handling moiety to move means that its active site can be permanently orientated towards the part of the subunit that forms part of the opening of the barrel of channel of the pore. The mobility of the nucleic acid binding protein may be constrained by increasing the number of points at which the protein is attached to the substrate and/or the use of specific linkers. Nucleotides are then distinguished on the basis of the different ways in which they affect the current flowing through the pore during the interaction.

In addition to the above, and the disclosure of WO2010/086603, a feeder molecule handling moiety, such as a nucleic acid handling moiety, may be attached directly to a nanopore, or may be attached indirectly via a linker, as disclosed in WO2010/004273, WO2010/004265 and/or WO 2012/033524.

Nanopore Adaptors

In any of the methods of the invention described herein, a nanopore may comprise a molecular adaptor that facilitates the interaction between the nanopore and the feeder molecule. The presence of the adaptor improves the host-guest chemistry of the nanopore and nucleotides present in the feeder molecule. The principles of host-guest chemistry are well-known in the art. The adaptor has an effect on the physical or chemical properties of the nanopore that improves its interaction with nucleotides. The adaptor typically alters the charge of the barrel or channel of the nanopore or specifically interacts with or binds to nucleotides thereby facilitating their interaction with the nanopore. An adaptor therefore increases the efficiency of the interaction between the nanopore and the feeder molecule compared to the efficiency in the absence of the adaptor. An adaptor may be referred to herein as an adaptor moiety.

The adaptor mediates the interaction between nucleotides present in the feeder molecule and the pore. The nucleotides may reversibly bind to the nanopore via or in conjunction with the adaptor. The nucleotides may reversibly bind to the nanopore via or in conjunction with the adaptor as they pass through the nanopore across the substrate. The nucleotides can also reversibly bind to the barrel or channel of the nanopore via or in conjunction with the adaptor as they pass through the nanopore across the membrane. The adaptor preferably constricts the barrel or channel so that it may interact with the nucleotides.

The adaptor is typically cyclic. The adaptor preferably has the same symmetry as the nanopore. An adaptor having seven-fold symmetry is typically used if the nanopore is heptameric (e.g. has seven subunits around a central axis that contribute 14 strands to a transmembrane β barrel). Likewise, an adaptor having six-fold symmetry is typically used if the nanopore is hexameric (e.g. has six subunits around a central axis that contribute 12 strands to a transmembrane β barrel, or is a 12-stranded β barrel). Any adaptor that facilitates the interaction between the nanopore and the nucleotide can be used. Suitable adaptors include, but are not limited to, cyclodextrins, cyclic peptides and cucurbiturils. The adaptor is preferably a cyclodextrin or a derivative thereof. The adaptor is more preferably heptakis-6-amino-β-cyclodextrin (am$_7$-βCD), 6-monodeoxy-6-monoamino-β-cyclodextrin (am$_1$-βCD) or heptakis-(6-deoxy-6-guanidino)-cyclodextrin (gu$_7$-βCD). The table below shows some suitable combinations of pores and adaptors.

| Pore | Number of strands in the transmembrane β-barrel | Adaptor |
|---|---|---|
| Leukocidin | 16 | γ-cyclodextrin (γ-CD) |
| OmpF | 16 | γ-cyclodextrin (γ-CD) |
| α-hemolysin (or a variant thereof discussed above) | 14 | β-cyclodextrin (β-CD) 6-monodeoxy-6-monoamino- β-cyclodextrin (am$_1$β-CD) heptakis-6-amino-β-cyclodextrin (am$_7$-β-CD) heptakis-(6-deoxy-6-guanidino)-cyclodextrin (gu$_7$-β-CD) |
| OmpG | 14 | β-cyclodextrin (β-CD) 6-monodeoxy-6-monoamino-β-cyclodextrin (am$_1$β-CD) heptakis-6-amino-β-cyclodextrin (am$_7$-β-CD) heptakis-(6-deoxy-6-guanidino)-cyclodextrin (gu$_7$-β-CD) |
| NalP | 12 | α-cyclodextrin (α-CD) |
| OMPLA | 12 | α-cyclodextrin (α-CD) |

The adaptor is preferably covalently attached to the nanopore. The adaptor can be covalently attached to the nanopore using any method known in the art. The adaptor may be attached directly to the nanopore. The adaptor is preferably attached to the pore using a bifunctional crosslinker. Suitable crosslinkers are well-known in the art. Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octananoate. The most preferred crosslinker is succinimidyl 3-(2-pyridyldithio)propionate (SPDP). Typically, the adaptor is covalently attached to the bifunctional crosslinker before the adaptor/crosslinker complex is covalently attached to the nanopore but it is also possible to covalently attach the bifunctional crosslinker to the nanopore before the bifunctional crosslinker/pore complex is attached to the adaptor.

The site of covalent attachment is selected such that the adaptor facilitates interaction of nucleotides released from or present in the target nucleic acid sequence with the nanopore and thereby allows detection of nucleotides. For nanopores based on (α-HL, the correct orientation of the adaptor within the barrel or channel of the nanopore and the covalent attachment of adaptor to the nanopore can be facilitated using specific modifications to the nanopore. In particular, every subunit of the nanopore, including the construct(s) may have a glutamine at position 139 of SEQ ID NO: 2 as disclosed in WO2010/086603. One or more of the subunits of the pore, including the construct(s), may have an arginine at position 113 of SEQ ID NO: 2 of WO2010/086603. One or more of the subunits of the pore, including the construct(s), may have a cysteine at position 119, 121 or 135 of SEQ ID NO: 2 of WO2010/086603 to facilitate attachment of the molecular adaptor to the pore.

Conditions

As described in detail herein, the methods of the invention involve the measuring of a property with respect to a nanopore. This is typically the current, in particular ionic current, passing through the nanopore during interaction with transfer nucleotides, e.g. transfer nucleotides of a feeder molecule, under the action of an applied potential. Suitable conditions for measuring ionic currents through nanopores are well known in the art. Suitable conditions are disclosed in e.g. WO2010/086603 and any of the conditions described therein may be applied to the current methods.

Measurement methods are typically carried out with a voltage applied across the substrate and nanopore. The voltage used is typically from −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 120 mV to 170 mV. It is possible to increase discrimination between different nucleotides using a nanopore by varying the applied potential.

Exemplary voltages include the following. For capture and retention of a feeder molecule in a nanopore (V1) the voltage may be e.g. +40 mV to +100 mV. For movement through the nanopore in the trans direction (V2), e.g. against the action of blocking moiety, the voltage may be e.g. +100 mV to +200 mV. For movement through the nanopore in the cis direction to eject the feeder molecule to the cis side of a substrate, the voltage may be e.g. −100 mV to +40 mV.

The measurement methods are carried out in the presence of any alkali metal chloride salt. In exemplary apparatus, the salt is present in an aqueous solution in a chamber. Potassium chloride (KCl), sodium chloride (NaCl) or caesium chloride (CsCl) is typically used. KCl is preferred. The salt concentration may be from 0.01 to 2.5M. The salt concentration is typically from 0.1 to 2.5M, from 0.3 to 1.9M, from 0.5 to 1.8M, from 0.7 to 1.7M, from 0.9 to 1.6M or from 1M to 1.4M. High salt concentrations provide a high signal to noise ratio and allow for currents indicative of the presence of a nucleotide to be identified against the background of normal current fluctuations. However, lower salt concentrations may have to be used so that the enzyme is capable of functioning.

The methods are typically carried out in the presence of a buffer. In exemplary apparatus, the buffer is present in an aqueous solution in a chamber. Any buffer may be used in the methods. One suitable buffer is Tris-HCl buffer. The methods are typically carried out at a pH of from 4.0 to 10.0, from 4.5 to 9.5, from 5.0 to 9.0, from 5.5 to 8.8, from 6.0 to 8.7 or from 7.0 to 8.8 or 7.5 to 8.5. The pH used is preferably about 7.5.

The methods are typically carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods may be carried out at room temperature. The methods are preferably carried out at a temperature that supports enzyme function, such as about 37° C. Good nucleotide discrimination can be achieved at low salt concentrations if the temperature is increased. However, lower temperatures, particularly those below room temperature, result in longer dwell times and can therefore be used to obtain a higher degree of accuracy.

In addition to increasing the solution temperature, there are a number of other strategies that can be employed to increase the conductance of the solution, while maintaining conditions that are suitable for enzyme activity. One such strategy is to use the lipid bilayer to divide two different concentrations of salt solution, a low concentration of salt on the enzyme side and a higher concentration on the opposite side. One example of this approach is to use 200 mM of KCl on the cis side of the membrane and 500 mM KCl in the trans chamber. At these conditions, the conductance through the pore is expected to be roughly equivalent to 400 mM KCl under normal conditions, and the enzyme only experiences 200 mM if placed on the cis side. Another possible benefit of using asymmetric salt conditions is the osmotic gradient induced across the nanopore. This net flow of water could be used to pull nucleotides into the nanopore for detection. A similar effect can be achieved using a neutral osmolyte, such as sucrose, glycerol or PEG. Another possibility is to use a solution with relatively low levels of KCl and rely on an additional charge carrying species that is less disruptive to enzyme activity.

Processing and Assembly of Polynucleotides

In any of the methods defined herein, the extension process may be a first extension process and wherein the methods further comprise repeating the extension process one or more times to further extend the polynucleotide synthesis molecule with one or more further transfer nucleotides to synthesise a polynucleotide having a predefined sequence.

The synthesised polynucleotides may be further processed as required.

For example in methods for the synthesis of single stranded polynucleotide synthesis molecule, the polynucleotide synthesis molecule may be converted into a double stranded molecule by the action of a further polymerase and primer using the single stranded polynucleotide synthesis molecule as a complementary template.

A double stranded polynucleotide synthesis molecule or any portion or region thereof synthesised using any of the methods defined and described herein may be amplified. Amplification may be performed by any suitable method, such as polymerase chain reaction (PCR), polymerase spiral reaction (PSR), loop mediated isothermal amplification (LAMP), nucleic acid sequence based amplification (NASBA), self-sustained sequence replication (3SR), rolling circle amplification (RCA), strand displacement amplification (SDA), multiple displacement amplification (MDA), ligase chain reaction (LCR), helicase dependent amplification (HDA), ramification amplification method (RAM) etc. Preferably, amplification is performed by polymerase chain reaction (PCR).

A polynucleotide having a predefined sequence synthesised by methods described herein may be joined to one or more other such polynucleotides to create larger synthetic polynucleotides.

Joining of multiple polynucleotides can be achieved by techniques commonly known in the art. A first polynucleotide and one or more additional polynucleotides synthesised by methods described herein may be cleaved to create compatible termini and then polynucleotides joined together by ligation. Cleavage can be achieved by any suitable means. Typically, restriction enzyme cleavage sites may be created in polynucleotides and then restriction enzymes used to perform the cleavage step, thus releasing the synthesised polynucleotides from any anchor/scaffold polynucleotide. Cleavage sites could be designed as part of the anchor/scaffold polynucleotides. Alternatively, cleavage sites could be created within the newly-synthesised polynucleotide as part of the predefined nucleotide sequence.

Assembly of polynucleotides may be performed using solid phase methods. For example, following synthesis a first polynucleotide may be immobilised on a solid surface. The first polynucleotide may be subject to a single cleavage at a suitable position distal to the site of surface immobilisation. The first polynucleotide will thus remain immobilised to the surface, and the single cleavage will generate a terminus compatible for joining to another polynucleotide. An additional polynucleotide may be subject to cleavage at two suitable positions to generate at each terminus a compatible end for joining to other polynucleotides. The additional polynucleotide may be compatibly joined with the first polynucleotide thus creating a larger immobilised polynucleotide having a predefined sequence and having a terminus compatible for joining to yet another additional polynucleotide. Thus iterative cycles of joining of preselected cleaved synthetic polynucleotides may create much longer synthetic polynucleotide molecules. The order of joining of the additional polynucleotides will be determined by the required predefined sequence.

Thus the assembly methods of the invention may allow the creation of synthetic polynucleotide molecules having lengths in the order of one or more Mb.

The synthesis and assembly methods of the invention may be performed using apparatuses known in the art. Techniques and apparatuses are available which allow very small volumes of reagents to be selectively moved, partitioned and combined with other volumes in different locations of an array, typically in the form of droplets Electrowetting techniques, such as electrowetting-on-dielectric (EWOD), may be employed, as described above. Suitable electrowetting techniques and systems that may be employed in the invention that are able to manipulate droplets are disclosed for example in U.S. Pat. Nos. 8,653,832, 8,828,336, US20140197028 and US20140202863. Thus polynucleotides having a predefined sequence may be synthesised and then immobilised to an electrowetting surface, as described above. Synthesised polynucleotides may be cleaved from the electrowetting surface and moved under the influence of an electric field in the form of a droplet. Droplets may be combined at specific reaction sites on the surface where they may deliver cleaved synthesised polynucleotides for ligation with other cleaved synthesised polynucleotides. Polynucleotides can then be joined, for example by ligation. Using such techniques populations of different polynucleotides may be synthesised and attached in order according to the predefined sequence desired. Using such systems a fully automated polynucleotide synthesis and assembly system may be designed. The system may be programmed to receive a desired sequence, supply reagents, perform synthesis cycles and subsequently assemble desired polynucleotides according to the predefined sequence desired.

Apparatus

All of the methods described herein involve the use of a nanopore positioned within a substrate.

The methods may involve verification processes, as described herein, which involve the detection of transfer nucleotides or nucleotide units within a nanopore, e.g. as a feeder molecule is translocated through the nanopore. Thus the methods of the invention relate to a nanopore as a component of a detection element comprising electrical control means and detection means, wherein the device is capable of detecting the presence of, the identity of and/or the integrity of a nucleotide, e.g. attached to a feeder molecule.

The methods may be carried out using apparatus such as described in WO2008/102120.

The methods involve measuring the current passing through the nanopore during interaction of the nanopore with the transfer nucleotide or feeder molecule as described herein. Therefore the apparatus also comprises an electric circuit capable of applying a potential and measuring an electrical signal across the membrane and nanopore. The methods may be carried out using a patch clamp or a voltage clamp. The methods preferably involve the use of a voltage clamp.

Figure 13:
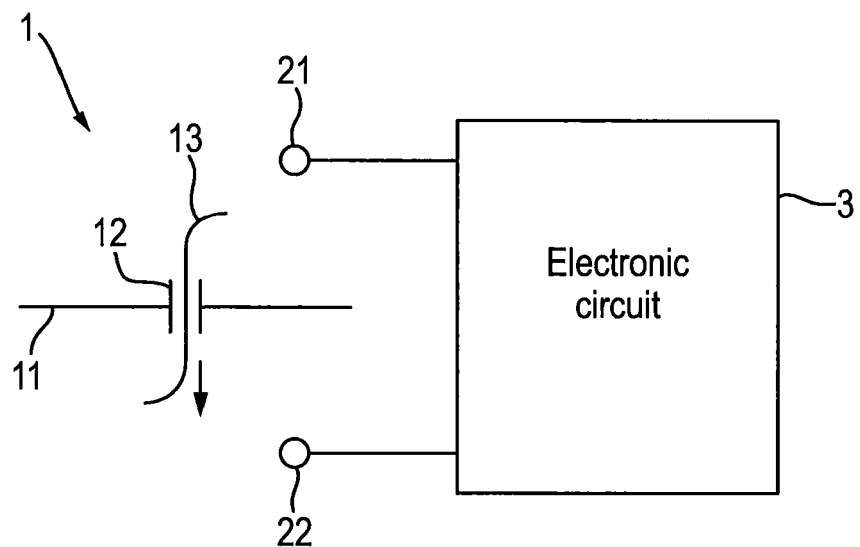
FIG. 13 depicts an example of a reaction unit.

With reference to FIG. 13, merely by way of illustration, a detection device may have any form comprising at least one detection element 1. The element 1 comprises a nanopore 12 positioned within a substrate 11. The element is capable of being operated to take measurements from a feeder molecule 13 comprising an attached transfer nucleotide during translocation of the feeder molecule through the nanopore. An example system capable of providing measurements is depicted. The Figure shows the arrangement of an electronic circuit 3 which can be used to implement one element of a system comprising one or more elements. The electronic circuit 3 may be connected to the electrode 22 in respect of one or more detection elements 1 of the system and to a common electrode 21. The electronic circuit 3 may optionally have an overall arrangement as described in WO2011/067559. The electronic circuit 3 may be arranged as follows to control the application of bias voltages across each detection element 1 and to take the measurements from each detection element 1.

Figure 14:
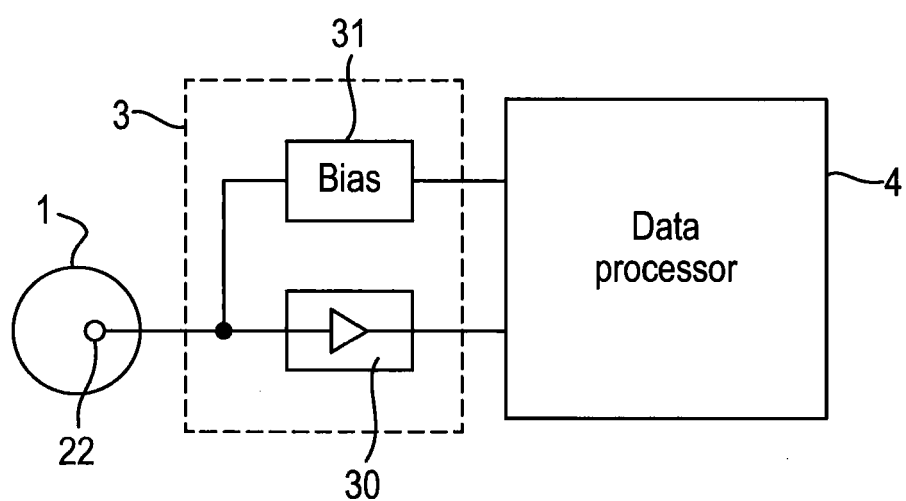
FIG. 14 depicts an example of a reaction unit comprising voltage bias and data processing means.

An exemplary non-limiting arrangement for the electronic circuit 3 is illustrated in FIG. 14 which shows components in respect of a single sensor element 1 that may be replicated for each one of the sensor elements 1 in a multi-element system. In this arrangement, the electronic circuit 3 includes a detection channel 30 and a bias control circuit 31 each connected to the sensor electrode 22 of the sensor element 1.

The detection channel 30 takes measurements from the sensor electrode 22. The detection channel 30 is arranged to amplify the electrical signals from the sensor electrode 22. The detection channel 30 is therefore designed to amplify very small currents with sufficient resolution to detect the characteristic changes caused by the movement of nucleotide units within a nanopore. The detection channel 30 is also designed with a sufficiently high bandwidth to provide the time resolution needed to detect each such interaction. Specifically, the detection channel 30 may be arranged as described in detail in WO2010/122293 or WO2011/067559.

The bias control circuit 31 supplies a bias voltage to the sensor electrode 22 for biasing the sensor electrode 22 with respect to the input of the detection channel 30.

During normal operation, the bias voltage supplied by the bias control circuit 31 is selected to enable translocation of a feeder molecule through the nanopore. Such a bias voltage is described herein and may typically be of a level up to −200 mV.

The bias voltage supplied by the bias control circuit 31 may also be selected so that it is sufficient to eject the translocating feeder molecule from the nanopore. By causing the bias control circuit 31 to supply such a bias voltage, the sensor element 1 is operable to eject a feeder molecule that is translocating through the nanopore. To ensure reliable ejection, the bias voltage is typically a reverse bias, although that is not always essential. When this bias voltage is applied, the input to the detection circuit 30 is designed to remain at a constant bias potential even when presented with a negative current (of similar magnitude to the normal current, typically of magnitude 50 pA to 100 pA).

Typically the electronic circuit 3 of each detection element is connected to a data processor for further analysis.

The methods of the invention may be carried out using any apparatus that is suitable for implementing a nanopore system in which a nanopore is inserted into a substrate as described herein.

In the methods of the invention a nanopore is typically provided as a component of a detection element comprising a nanopore, electrical control means and detection means. The nanopore is positioned within a substrate. As described herein, the substrate defines a cis side of the substrate and a trans side of the substrate. The enzyme and polynucleotide synthesis molecule are provided adjacent the nanopore on the trans side. Free transfer nucleotides or feeder molecules having attached transfer nucleotides are introduced to the nanopore from the cis side.

Apparatus typically comprises a chamber comprising an aqueous solution and the substrate separates the chamber into two sections, a cis chamber on the cis side of the substrate and a trans chamber on the trans side of the substrate comprising the enzyme and polynucleotide synthesis molecule. The cis and trans sides of the substrates typically comprise reaction chambers or reaction volumes which are in fluid communication via the channel of the nanopore. A free transfer nucleotide or a feeder molecule comprising a transfer nucleotide is contacted with the nanopore by introducing the transfer nucleotide or feeder molecule into the cis chamber as described herein.

Multiple detection elements may be provided to form a system of detection elements. Multiple detection elements may be provided to form an array of detection elements comprising a system. The reaction chambers may be components of a reaction unit. Typically, each detection element may be provided as a component of a separate reaction unit. Each reaction unit may be provided with separate reagents and may be structured so as to prevent fluid and electrical communication therebetween. As such, each nanopore in each reaction unit may be provided in a self-contained manner and with the capability of being individually addressable so as to synthesise a different polynucleotide molecule of different pre-defined sequence. By structuring a system comprising multiple reaction units it is possible to perform multiple synthesis reactions in parallel, each synthesising a different polynucleotide molecule having a pre-defined sequence (multiplex synthesis).

In any of the methods described and defined herein a nanopore may be positioned within a reaction chamber of a system, wherein the system comprises an array of nanopores, wherein the substrate separates the reaction chamber into a cis reaction chamber portion and a trans reaction chamber portion, each nanopore providing a channel through the substrate from the cis to the trans reaction chamber portion.

In any such method, the system may comprise a common cis chamber portion and wherein trans reaction chamber portions may comprise an array of trans chambers that are fluidically isolated from each other, wherein each trans chamber is separated from the cis chamber by a substrate comprising a nanopore; wherein polynucleotide synthesis molecules of different sequence may be synthesised in different trans reaction chambers, and wherein the potential difference applied across each trans reaction chamber and the cis chamber may be independently controlled.

Reaction chambers, and preferably trans reaction chambers may be provided as droplets within an electrowetting-on-dielectric system (EWOD) as described above.

EWOD systems provide a dielectric-coated surface which facilitates microfluidic manipulation of very small liquid volumes in the form of microdroplets (e.g. see Chou, W-L., et al. (2015) Recent Advances in Applications of Droplet Microfluidics, Micromachines, 6: 1249-1271.). Droplet volumes can programmably be created, moved, partitioned and combined on-chip by electrowetting techniques.

Thus electrowetting and other systems provide means to move polynucleotides to different locations, e.g. after synthesis for purposes such as ligating polynucleotides to synthesise larger polynucleotides, as described herein. Prior to being moved the polynucleotides may be amplified, e.g. by PCR, or by any other suitable amplification method described herein.

Other microfluidic platforms are available which may be used in the synthesis methods of the invention. For example, the emulsion-based microdroplet techniques which are commonly employed for nucleic acid manipulation can be used in conjunction with microfluidic devices. In such systems microdroplets are formed in an emulsion created by the mixing of two immiscible fluids, typically water and an oil. Emulsion microdroplets can be used as reaction chambers, particularly trans reaction chambers, and can programmably be created, moved, partitioned and combined in microfluidic networks. Hydrogel systems are also available.

In any of the apparatus, devices or systems described and defined herein for performing the synthesis methods of the invention the apparatus, devices or systems may be provided wherein a cis chamber, or a cis reaction chamber, or portion thereof is provided with one or more feeder molecules of any type described and defined herein.

Data Storage

Polynucleotide molecules are naturally capable of storing information encoded within them due to differences in the identity and sequences of nucleobases forming the structure of the polynucleotide molecule. The natural data storage function of polynucleotide molecules can be exploited for the storage of new information by synthesising new polynucleotide molecules according to a specific nucleobase sequence which can thus encode new information within the polynucleotide molecule which can later be accessed or "read" to retrieve the information.

Thus the invention additionally provides a method of storing data in a polynucleotide molecule, the method comprising: (a) performing a first extension reaction by extending a polynucleotide synthesis molecule with one or more transfer nucleotides by any one of the synthesis methods described and defined herein, thereby generating a first nucleotide sequence; and (b) performing one or more further extension reactions by further extending the polynucleotide synthesis molecule with one or more further transfer nucleotides by any one of the synthesis methods described and defined herein, thereby generating a second or further nucleotide sequence in the polynucleotide synthesis molecule, wherein sequences are indicative of information encoded into the extended polynucleotide molecule.

New information can, for example, be encoded into a polynucleotide molecule in a digital form.

Thus the invention additionally provides a method of storing data in digital form in a polynucleotide molecule, the method comprising: (a) performing a first extension reaction by extending a polynucleotide synthesis molecule with one or more transfer nucleotides by any one of the synthesis methods described and defined herein, thereby generating a nucleotide sequence in the polynucleotide synthesis molecule indicative of the "0" or "1" state of a bit of digital information; and (b) performing a second extension reaction by further extending the polynucleotide synthesis molecule with one or more further transfer nucleotides by any one of the synthesis methods described and defined herein, thereby generating a nucleotide sequence in the polynucleotide synthesis molecule indicative of the opposite state of the bit to that generated in step (a).

Any such method may comprise repeating steps (a) and (b) multiple times to generate nucleotide sequences indicative of multiple bits of digital information. In any such method the one or more transfer nucleotides of step (a) are distinguishable from the one or more transfer nucleotides of step (b).

A nucleotide sequence can be incorporated into a polynucleotide synthesis molecule to be indicative of the "0" or "1" state of a bit of digital information in any suitable way. For example bits of digital information can be created using two different species of transfer nucleotide. For example a polynucleotide synthesis molecule can be extended by the incorporation of an adenine (A) nucleobase in a first cycle followed by a cytosine (C) in a second subsequent cycle. The presence of A in the polynucleotide molecule can thus be indicative of the "0" or "1" state of a bit of digital information. The presence of C juxtaposed adjacent to A can thus be indicative of the opposite state of the bit. Incorporation of multiple AC pairs of nucleobases in sequence can therefore allow for digital information to be encoded into the polynucleotide molecule in bit form. A and C are provided as an example only. Any nucleobases can be used provided they can be distinguished from each other.

Incorporation of single nucleobases of alternating species is one way of generating a bit of digital information. Bits can alternatively be generated by the incorporation of two or more, i.e. a first string, of nucleobases of the same or indistinguishable species in the same or successive cycles of synthesis which can thus be indicative of the "0" or "1" state of a bit of digital information. This can then be followed by the incorporation of two or more, i.e. a second string, of nucleobases of the same or indistinguishable species in the same or successive cycles of synthesis which can thus be indicative of the opposite state of the bit to that previously generated. Any nucleobases can be used provided that the nucleobases of the first string can be distinguished from the nucleobases of the second string. First and second strings need not consist of the same number of nucleobases since the transition between first and second string is indicative of the transition between the "0" or "1" state of the bit of digital information and the opposite state of the bit.

Any of the polynucleotide extension methods described and defined herein may be followed by a step of determining the sequence of the extended polynucleotide. Such a step may be carried out using a nanopore (such as the nanopore used in the polynucleotide extension method) using nanopore sequencing techniques which are well known in the art. By way of further example, a step of determining sequence of the extended polynucleotide may be carried out subsequent to a method of storing data in a polynucleotide molecule, such as described herein, for example to provide a write-read system.

Any such method of data storage may be performed using any of the apparatus, devices and systems described and defined herein.

EXAMPLES

The following Examples are provided to illustrate the invention but they do not limit the invention.

Example 1: Example Synthesis Voltage Cycle

Figure 12:
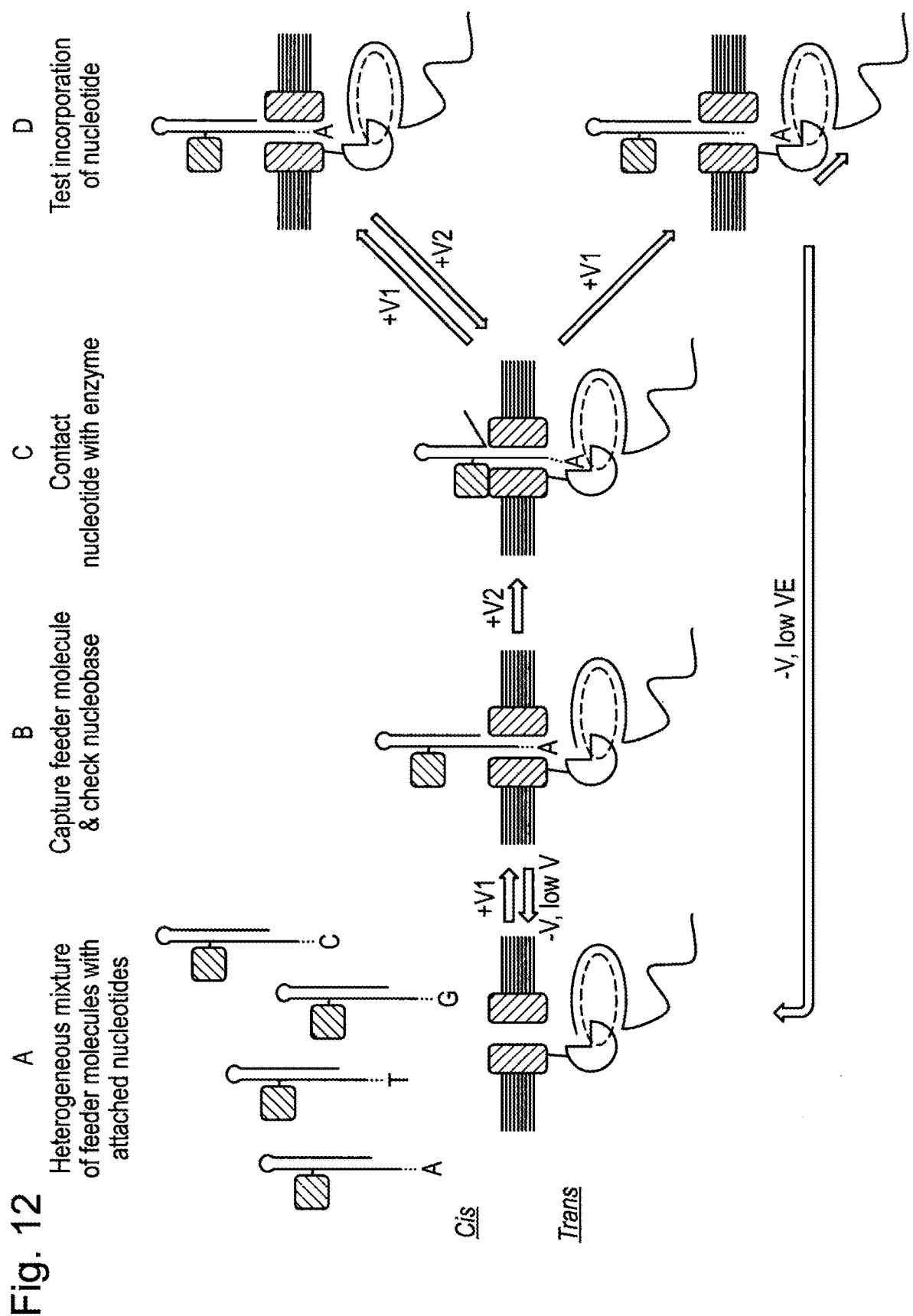
FIG. 12 depicts an example of an extension process of a method of the invention using verification processes.

An example synthesis voltage cycle will be described with reference to FIG. 12 (A to D) merely by way of illustration, and with further reference to FIGS. 1 and 8.

A—Provide a Heterogeneous Mixture of Feeder Molecules with Attached Nucleotides

A nanopore is positioned in a substrate.

An enzyme, such as a polymerase, is provided adjacent the nanopore on the trans side of the substrate. The enzyme is preferably attached to the nanopore by any of the means described herein.

A polynucleotide synthesis molecule to be extended is provided on the trans side of the substrate. The polynucleotide synthesis molecule is preferably tethered to the enzyme, e.g. via a coupling moiety as described herein. In the present example the coupling moiety is a scaffold molecule comprised of a circular polynucleotide molecule hybridised to the polynucleotide synthesis molecule. The circular polynucleotide scaffold molecule preferably comprises universal nucleobases as described herein Populations of feeder molecules are provided on the cis side of the membrane attached to pre-defined transfer nucleotides. Any nucleotide, e.g. as described herein may be attached. Thus the substrate separates the enzyme/polynucleotide synthesis molecule and the feeder molecules. Each population of feeder molecules has the same species of pre-defined transfer nucleotide attached. For the purposes of illustration, in the present example four populations are shown each comprising one feeder molecule. In practice many feeder molecules will be provided in each population. Each population may be provided in combination with the other populations as a heterogenous mixture of populations in solution on the cis side of the membrane.

B—Capture Feeder Molecule & Check Nucleobase

Moving from A to B, voltage +V1 is applied to capture a feeder molecule into a nanopore. The feeder molecule pauses in the nanopore when the nanopore contacts blocking moiety B1, being a double-stranded region of the feeder molecule (FIG. 7), such that the nucleobase to be incorporated is held within the pore itself and can be identified via detection in a first verification process as described herein. At this position the nucleotide to be incorporated is physically separated from the enzyme such that the enzyme cannot act on the nucleotide.

The nucleobase to be incorporated is ideally detected directly, and therefore information regarding its presence, absence, or any damage thereto can be used to make decisions as to whether to move the feeder molecule further through the nanopore and to check successful incorporation of the nucleotide. Alternatively, or additionally, the nucleobase attached to the feeder molecule could be identified by a variable barcode section in the sequence of the feeder molecule.

Moving from B back to A, if, following performance of the first verification process, the nucleobase positioned in the nanopore is determined not to be the desired transfer nucleobase or if the nucleobase is determined to be damaged, then a reverse voltage or a reduced voltage is applied to move the feeder molecule back through the nanopore and release/eject the feeder molecule back to solution on the cis side of the membrane.

C—Contact Nucleotide with Enzyme

Moving from B to C, if the nucleobase positioned in the nanopore is determined to be the desired transfer nucleobase following performance of the first verification process, the voltage can be increased to +V2. The increase in voltage causes a portion of the double-stranded region of the feeder molecule (B1) to de-hybridise. This allows the feeder molecule to move further into the nanopore. Further translocation is prevented when blocking moiety B2 contacts the nanopore and retards further movement. At this position the feeder molecule is positioned in the nanopore such that the attached transfer nucleotide contacts the enzyme and can be incorporated into the polynucleotide synthesis molecule. The feeder molecule may be paused at this position within the nanopore for a defined period of time to maximise the efficiency of successful incorporation.

D—Test Incorporation of Nucleotide

Moving from C to D, the voltage is reduced back to +V1. This allows the double-stranded region of B1 of the feeder molecule to re-form by hybridisation allowing the feeder molecule to move in the cis direction and to be "pulled up" through the nanopore. The lower voltage retains the feeder molecule within the nanopore enabling a detection step to be performed to check for the presence or absence of the nucleobase to verify successful incorporation (second verification process). If the nucleobase is determined to be absent, signaling successful incorporation of the nucleotide into the polynucleotide synthesis molecule, then a reverse voltage or a reduced voltage is applied to move the feeder molecule back through the nanopore and release/eject the feeder molecule back to solution on the cis side of the membrane. The entire cycle may then be repeated in order to incorporate a further and different nucleotide.

Moving from D back to C, if the nucleobase remains attached to the feeder molecule, the voltage can be increased back to +V2 to return the feeder molecule back to a position in the nanopore whereupon the nucleotide may contact the enzyme.

Voltage Cycle

Figure 15:
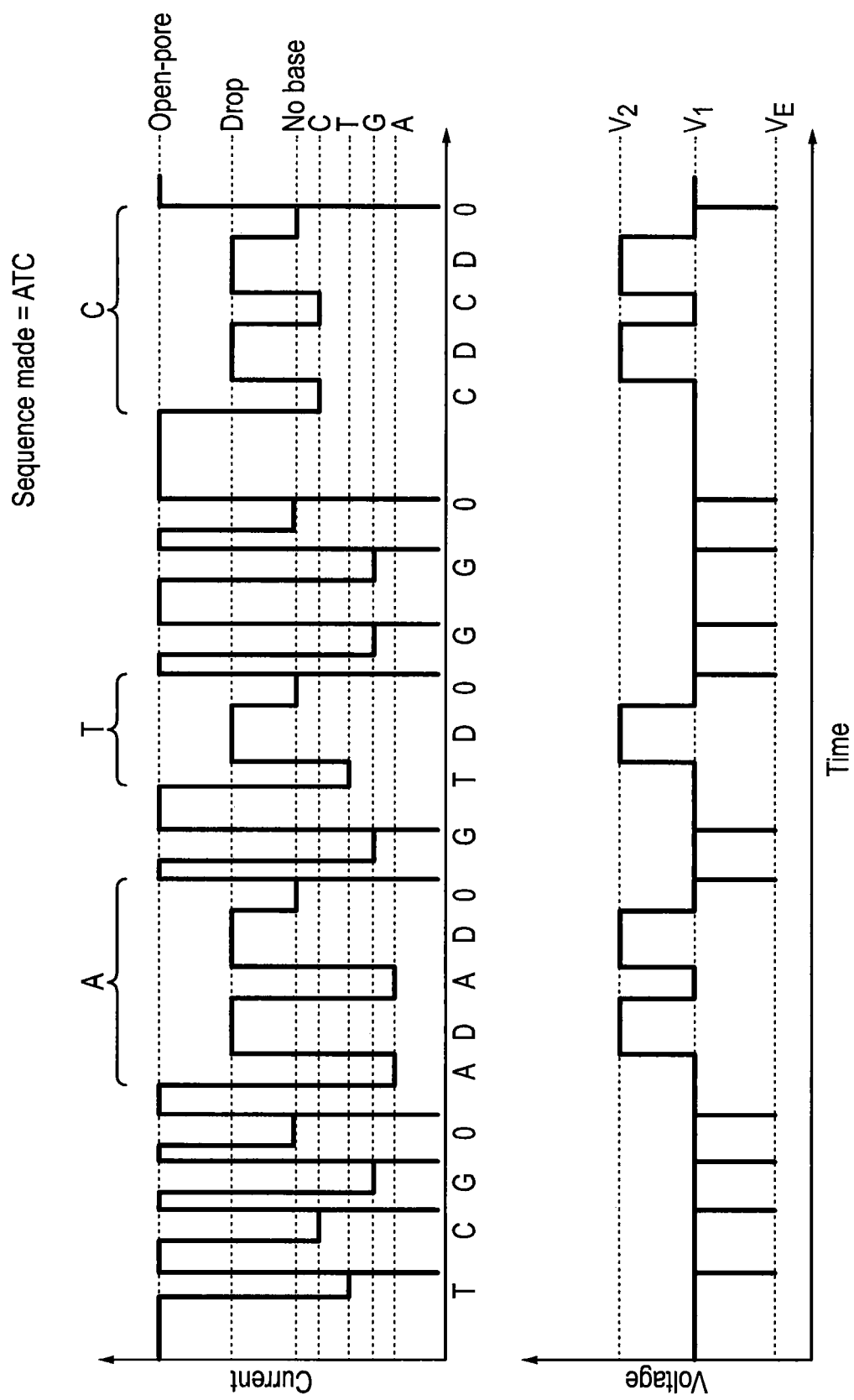
FIG. 15 depicts an example of voltage control cycles for performing synthesis reactions using methods of the invention.

An example voltage cycle and corresponding current values for the illustrative scheme outlined above is shown in FIG. 15.

Voltages:

V1=voltage sufficient to capture a feeder molecule with an attached nucleotide. The nucleotide is held in the nanopore to detect the nucleotide and to check the identity and/or integrity of the nucleobase of the nucleotide.

V2=voltage applied if the desired transfer nucleotide is detected, the higher voltage is capable of moving the feeder molecule through the nanopore in the trans direction to a position whereby the nucleotide may be contacted with the enzyme.

VE=ejection voltage. This may be, for example a reverse voltage, zero voltage, or a voltage lower than V1. The voltage is any voltage sufficient to move the feeder molecule through the nanopore in the cis direction to a point where it is ejected form the nanopore and returned into solution on the cis side of the substrate. VE is expected to be implemented as very short lived pulse before returning the applied voltage back to V1 in order to draw a different feeder molecule into the nanopore.

Current Levels:

Open-pore is the current measured when the nanopore is not occupied by a feeder molecule.

A/T/G/C/0 are the current levels measured for feeder molecules during a first verification process at applied voltage V1 for feeder molecules that have A/T/G/C or no nucleotide (0) attached respectively Drop=current level measured when a feeder molecule is "dropped" under higher V2 voltage. In other words, the current level measured when a feeder molecule is moved further through the nanopore such that the attached transfer nucleotide contacts the enzyme and can be incorporated into the polynucleotide synthesis molecule.

In the present example all feeder molecules are shown with the same drop current—this assumes no barcoding differences in feeder molecules, no differences in linkers, and no current change when the nucleotide is in the "drop" location.

Example Applied Voltage Sequence:

Described below is an example possible sequence of controlled applied voltage and measured current to make the sequence ATC.

Start Cycle:
- V1>capture feeder molecule and detect unwanted T>eject VE>
- V1>capture feeder molecule and detect unwanted C>eject VE>
- V1>capture feeder molecule and detect unwanted G>eject VE>
- V1>capture feeder molecule, detect feeder molecule with damaged base>eject VE>
- V1>capture feeder molecule, detect feeder molecule without base>eject VE>
- V1>capture feeder molecule and detect desired A>drop by applying V2>
- V1 check>A still present>drop again by applying V2>
- V1 check>no base present—indicates successful incorporation>eject VE>

Repeat Cycle:
- V1>capture feeder molecule and detect unwanted G>eject VE>
- V1>capture feeder molecule and detect desired T>drop by applying V2>
- V1 check>no base indicates successful incorporation>eject VE>

Repeat Cycle:
- V1>capture feeder molecule and detect unwanted G>eject VE>
- V1>capture feeder molecule and detect unwanted G>eject VE>
- V1>capture feeder molecule, detect feeder molecule without base>eject VE>
- V1>capture feeder molecule and detect desired C>drop by applying V2>
- V1 check>C still present>drop again by applying V2>
- V1 check>no base indicates successful incorporation.

Example 2—Exemplary System to Capture and Deliver Transfer Molecules

Figure 16:
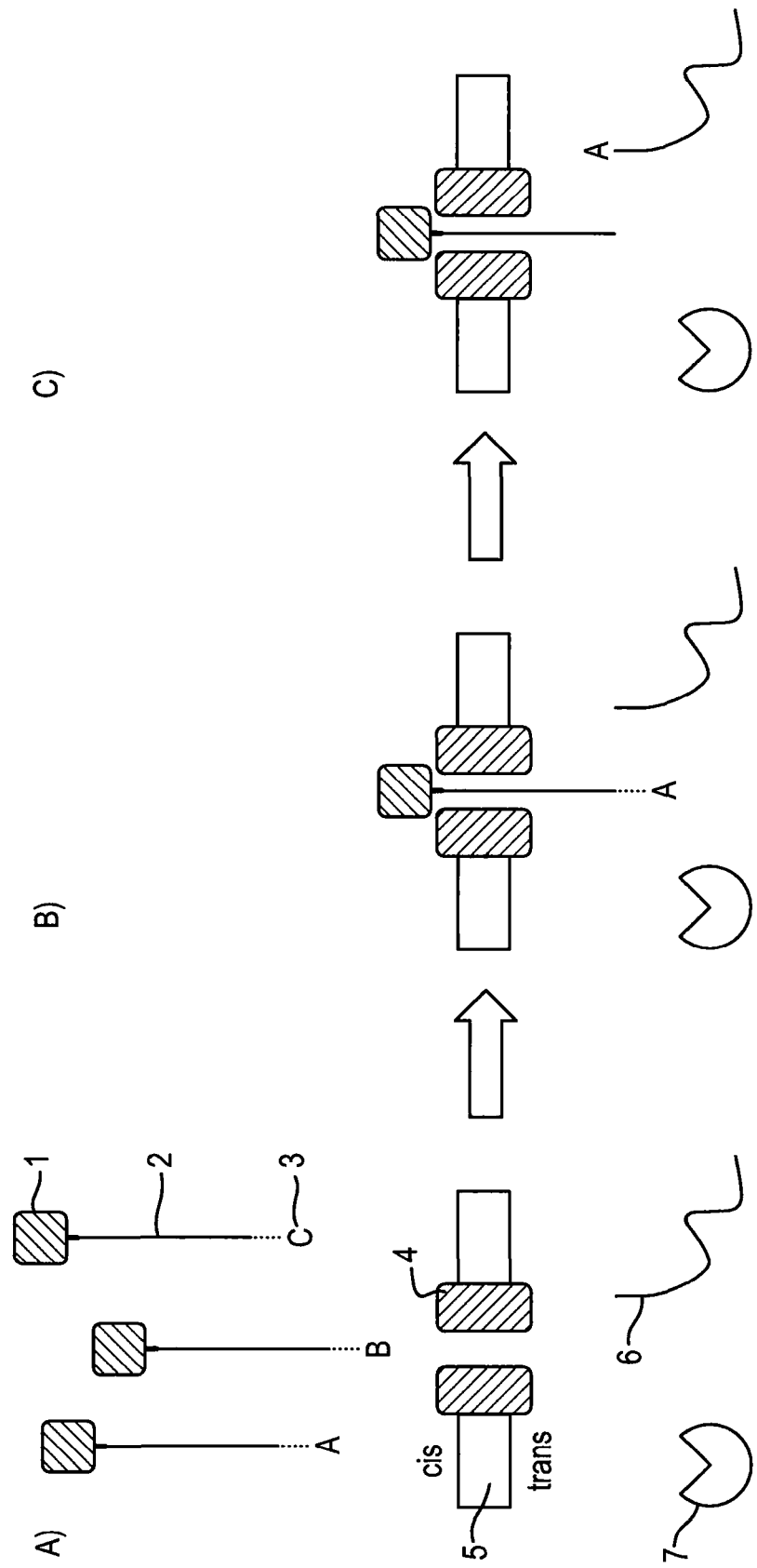
FIG. 16 shows a simplified example overview illustrating features of the method of the invention.

FIG. 16 is a schematic non-limiting exemplary illustration of a system to capture and deliver transfer molecules (3) across a nanopore (4) in a membrane (5) to extend a synthesis molecule (6). FIG. 1B illustrates the capture of a single transfer molecule (3) captured from a mixed pool of transfer molecules (labelled A/B/C). The transfer molecule can for example be a nucleotide (a transfer nucleotide, as described herein). The synthesis molecule can for example be a polynucleotide (a polynucleotide synthesis molecule, as described herein).

Capture and delivery of the transfer molecule can be controlled by altering the conditions of the system, for example the voltage across the system can be controlled using an electronic circuit with electrodes connecting the solutions on either side of the membrane.

Software can monitor the system in real-time, for example measuring the current through the nanopore under an applied voltage across the membrane, and actively control the voltage in response to changes in current. The transfer molecule (3) can be delivered by means of a feeder molecule (2) through the nanopore (4) to the opposite side of a membrane (5), whereupon the transfer molecule is detached from the feeder and transferred to the synthesis molecule (6), for example by enzyme (7) mediated catalysis. The identity of the transfer molecule and feeder can be determined when captured from a pool of transfer molecules. The transfer of desired transfer molecules can be controlled by rejecting unwanted captured transfer molecules back to the mixed source pool. Capture and rejection can be controlled by controlling the voltage and conditions of the system, for example software can monitor the current through the nanopore to determine changes that are indicative of events including capture of transfer molecule or feeder molecule, loss of transfer molecule or feeder molecule, identity of transfer molecule or feeder molecule, etc. The feeder molecule optionally has a blocker (blocking moiety; 1) that pauses or prevents partial or full translocation of the feeder molecule. The blocker holds the transfer molecule in the nanopore in a constrained volume, preventing loss into the bulk solution on the opposite side of the membrane, and enabling sufficient time for a transfer reaction to occur in a controlled location. After transfer to the synthesis molecule the feeder molecule can optionally be ejected back to the origin side of the membrane, or fully translocated through the nanopore to the opposite side.

Example 3—Exemplary System Involving Ligation and Endonucleases

Figure 17:
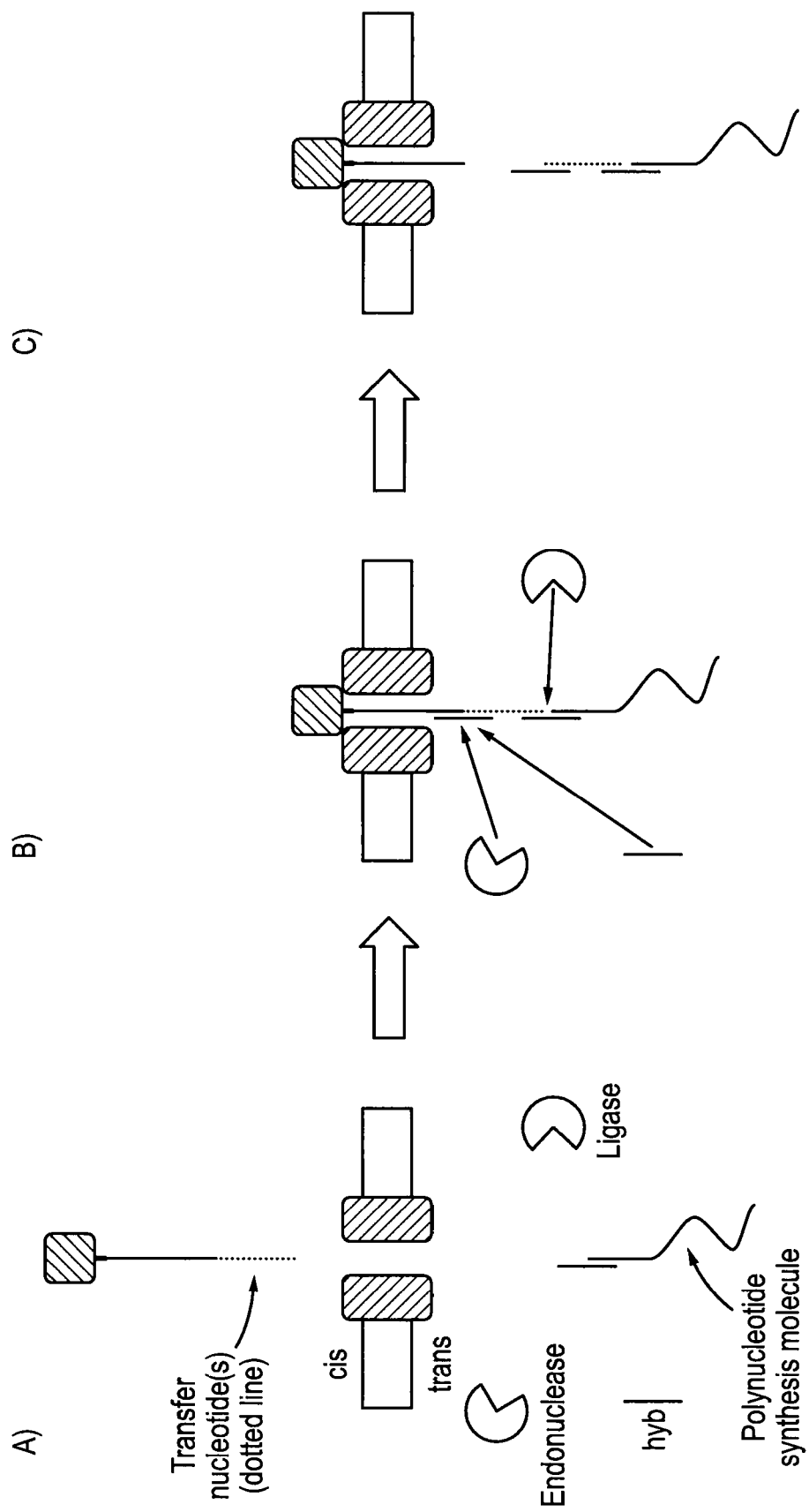
FIG. 17 shows a simplified example overview illustrating features of the method of the invention involving ligation.

FIG. 17 is a non-limiting exemplary schematic illustration of a system setup to extend a polynucleotide synthesis molecule with transfer nucleotides by means of ligation and restriction enzymes. FIG. 17 illustrates a nanopore in a membrane that separates the polynucleotide synthesis molecule on the trans side from a pool of transfer nucleotides on the cis side. The trans side of the membrane also contains the components and/or conditions required for attachment and detachment of the transfer nucleotide (e.g. enzymes, cofactors, polynucleotides). For example, as illustrated in FIG. 17A), the trans side can contain ligases to join nucleotides, restriction enzymes to cut nucleotides, and complementary polynucleotides that can hybridise to either the polynucleotide synthesis molecule and/or the transfer nucleotide to create regions of double-stranded polynucleotide. The components on one side of the membrane are ideally stable and will not cross react. Reaction ideally only occurs when the transfer nucleotide is delivered through the nanopore.

Voltage applied to electrodes across the membrane can be used to control capture of a transfer nucleotide from a mixed pool of transfer nucleotides on the cis side to deliver it through the nanopore into the vicinity of the polynucleotide synthesis molecule. The transfer nucleotide can be measured during capture, by measuring the change in current for example, to determine if it is the desired species, and then either ejected if not the correct species (by reducing or reversing the voltage) or passed through to the adjacent side if it is the correct species (by maintaining or increasing the applied capture voltage). When translocated through the nanopore the transfer nucleotide can be joined to the polynucleotide synthesis molecule by means of ligation. The transfer nucleotide can be separated from the feeder molecule by a restriction endonuclease. FIG. 17 illustrates how a sticky double-stranded overhang on the polynucleotide synthesis molecule can hybridise to the transfer nucleotide to aid ligation. The figure illustrates how a small complementary oligonucleotide (hyb) can hybridize to the transfer nucleotide, which creates a recognition site for a restriction endonuclease to cut the strands, and also regenerates a sticky double-stranded overhang for the next ligation cycle. After transfer of the transfer polynucleotide the feeder molecule can either be ejected by changing the voltage or allowed to escape back to the cis side (in some embodiments the feeder could be fully translocated through to the trans side).

It is to be understood that the above-described system is provided to illustrate one mechanism by which a polynucleotide synthesis molecule could be extended by multiple transfer nucleotides simultaneously. Other mechanisms by which this could be achieved will be readily apparent to a skilled person. The above example is not to be construed as limiting in any way.

Example 4—Further Exemplary System Involving Ligation and Endonucleases

Figure 18:
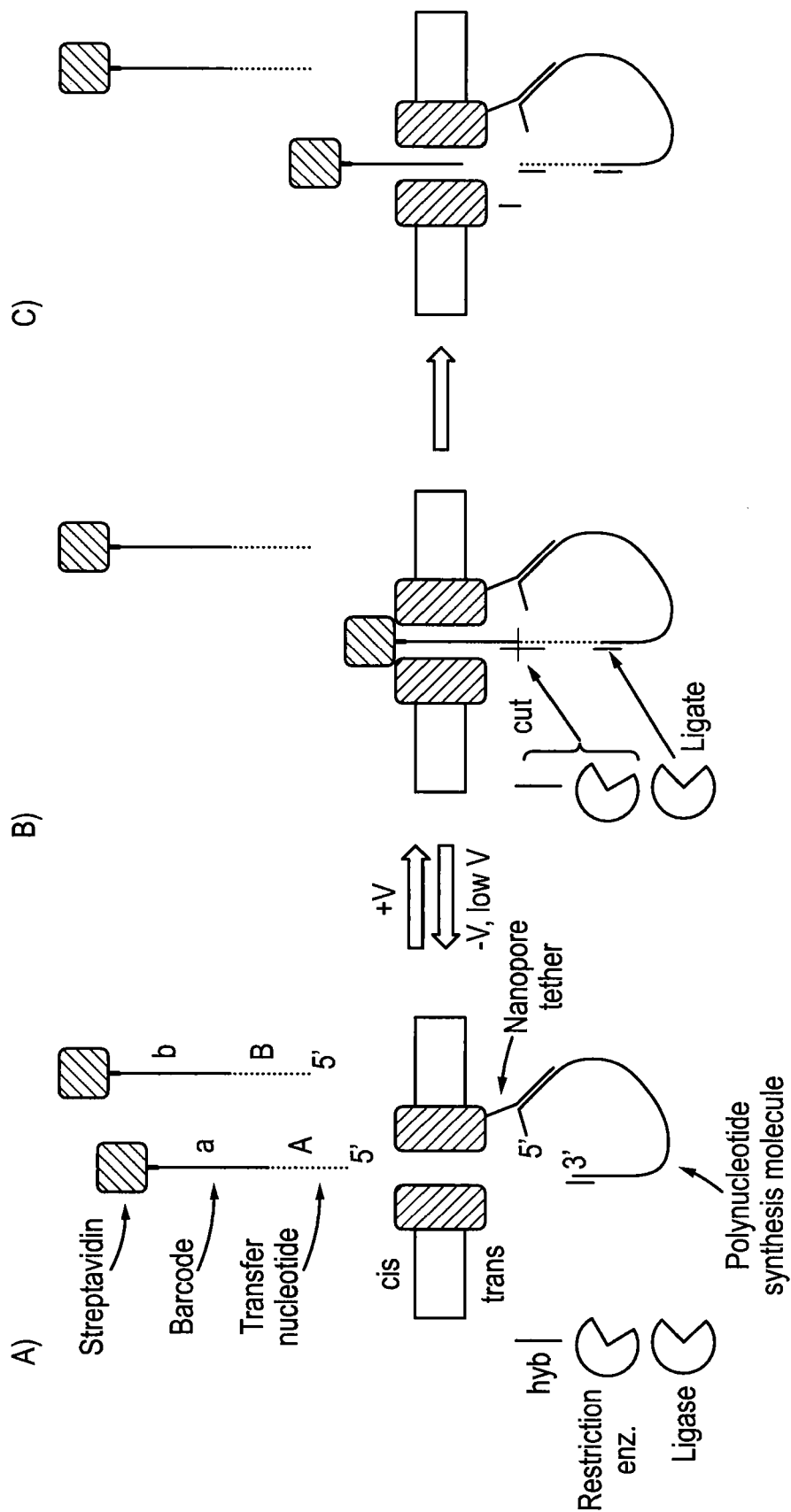
FIG. 18 shows a further simplified example overview illustrating features of the method of the invention involving ligation.

FIG. 18 shows a further non-limiting example of the transfer of transfer nucleotides to a polynucleotide synthesis molecule using ligation and restriction via a nanopore. In FIG. 18(A) the system contains a mixed pool of transfer nucleotides on the cis side of the membrane to extend the polynucleotide synthesis molecule on the trans side of the membrane. The system is designed so that reactions can only occur when the separated components are brought together on the trans side of the membrane.

FIG. 18 illustrates the use of a nanopore with an attached oligonucleotide tether, which is employed to retain the polynucleotide synthesis molecule near to the nanopore. The oligonucleotide tether is attached to the nanopore by means known in the art, for example a maleimide terminated synthetic oligonucleotide that is reacted to a cysteine modification introduced to an appropriate exposed region on the outer region of the nanopore. If the nanopore is oligomeric the nanopore is ideally created to have a single tether by means known in the art, for example by using a mixture of modified and unmodified protein monomers and purifying the species with the desired number of modified units.

The cis side of the membrane contains a mixed pool of transfer nucleotides, for example two species labelled A and B in FIG. 18A. The transfer nucleotides are connected to polynucleotide feeder molecules. The feeder molecules are barcoded so that when captured in the nanopore the identity of the transfer nucleotide can be determined by the characteristics of the current signal (e.g. the extent of the current blockade). In other examples the transfer nucleotide may be determined directly when fed into the nanopore. The feeder molecule has a blocker (blocking moiety), for example a streptavidin bound to a terminal 3'-biotin. When captured under an applied potential the blocker prevents full translocation of the transfer and feeder molecule, enabling it to be held in the vicinity of the synthesis molecule for sufficient time to enable the attachment process to occur. The 5' end of the transfer nucleotides are marked on the figure. The 5' end of the transfer nucleotides are phosphorylated to enable ligation. Ideally none of the nucleotides on the trans side are 5'-phosphorylated to prevent any unwanted ligations.

The trans side contains the synthesis polynucleotide. The 5' and 3' ends of the polynucleotide synthesis molecule are marked in FIG. 18A. The 5' end of the synthesis molecule is complementary to the nanopore tether on the trans side of the nanopore, enabling it to remain hybridised to the nanopore during the synthesis process. The terminal 5'-end has suitable chemistry for attaching a sequencing adapter, for example BCN alkyne click-chemistry to enable attachment to a 3'-azide on sequencing adapter. The 5' end is ideally designed to prevent any interaction with the nanopore under both positive and negative applied voltages until the sequencing adapter is attached. This can be achieved by controlling the geometry, position, and end structure of the polynucleotide. The 3' end of the polynucleotide synthesis molecule is the end that is extended by transfer nucleotides that are delivered through the nanopore. The 3' end has a complementary polynucleotide hybridised to create a double-strand end with a sticky overhang (e.g. a 3'-recessed by 4 bases) to facilitate efficient ligation. It is understood that a person skilled in the art may design any number of ends to control the attachment chemistry, including single-stranded, blunt ended double-strand, and 5' or 3' overhang double-strand structures.

The trans side also contains all the components and cofactors required to facilitate the joining and cutting reactions to deliver the transfer nucleotide to the synthesis polynucleotide. For example, the figure illustrates the use of a ligase, a restriction endonuclease and a complementary oligonucleotide (hyb).

The figure illustrates the capture of transfer nucleotides under an applied voltage (e.g. +100 mV) from the cis side of the membrane through the nanopore (A>B). If the incorrect transfer nucleotide is detected the voltage can be quickly reduced (e.g. to 0 mV allowing the nucleotide to escape by diffusion) or reversed (e.g. to −20 mV) before the ligation/cutting reactions occur (B>A). If the desired transfer nucleotide is detected, the voltage can be held for sufficient time to allow the ligation and cutting reactions to occur (B). The figure illustrates how the 5'-phosphorylated end of the transfer nucleotide hybridises to the complementary overhang of the 3'-end of the polynucleotide synthesis molecule, and joining of the 5'end of the transfer nucleotide to the 3'end of the polynucleotide synthesis molecule by means of ligation. The ligation sequences and end structures can also be designed so that the newly formed connection cannot be cut by the restriction enzyme also present in the solution (for example by choosing nucleotides on the 5'end of the transfer nucleotide that do not recreate the recognition sequence of the restriction enzyme).

The figure illustrates how the transfer nucleotide can be cleaved from the feeder molecule by means of a restriction endonuclease cut. For example, this can involve hybridization of a small oligonucleotide from the solution on the trans side of the membrane to the transfer nucleotide, creating a recognition site for the subsequent binding of the sequence specific restriction endonuclease, which then cuts the transfer nucleotide to release it from the feeder molecule. The sequences can be designed so that, for example, the restriction enzyme leaves a sticky overhang on the 3'end of the polynucleotide synthesis molecule to facilitate the next round of attachment. After the cutting reaction the feeder molecule can be released. Ideally the system is configured such that the feeder molecule is lost back to the cis side upon cutting because there is insufficient force under the electrophoretic conditions of a moderate applied voltage to keep it trapped. This loss and return to open-pore current indicates the cutting reaction has occurred, which can be detected by the software monitoring the pore to initiate the next cycle of the reaction. Alternatively the voltage can be reversed after a designated time (sufficient for a high probability of successful reaction) to eject the feeder molecule. This process can employ gentle voltages that are insufficient to capture the polynucleotide synthesis molecule or other elements on the trans side.

Ideally the attachment reaction occurs before the cutting reaction. This can be controlled for example by controlling the relative concentrations of the ligase and the restriction endonuclease and complementary hyb.

At the end of the extension process the scheme can be repeated, attaching another transfer nucleotide to the polynucleotide synthesis molecule.

Example 5—Exemplary System Describing Repeat Extension

This example details a scheme in which a polynucleotide synthesis molecule, in this case DNA, is repeatedly extended by ligating transfer nucleotides derived from feeder molecules (in this case DNA oligonucleotides) delivered through a nanopore from the cis to the trans of a membrane.

Figure 19:
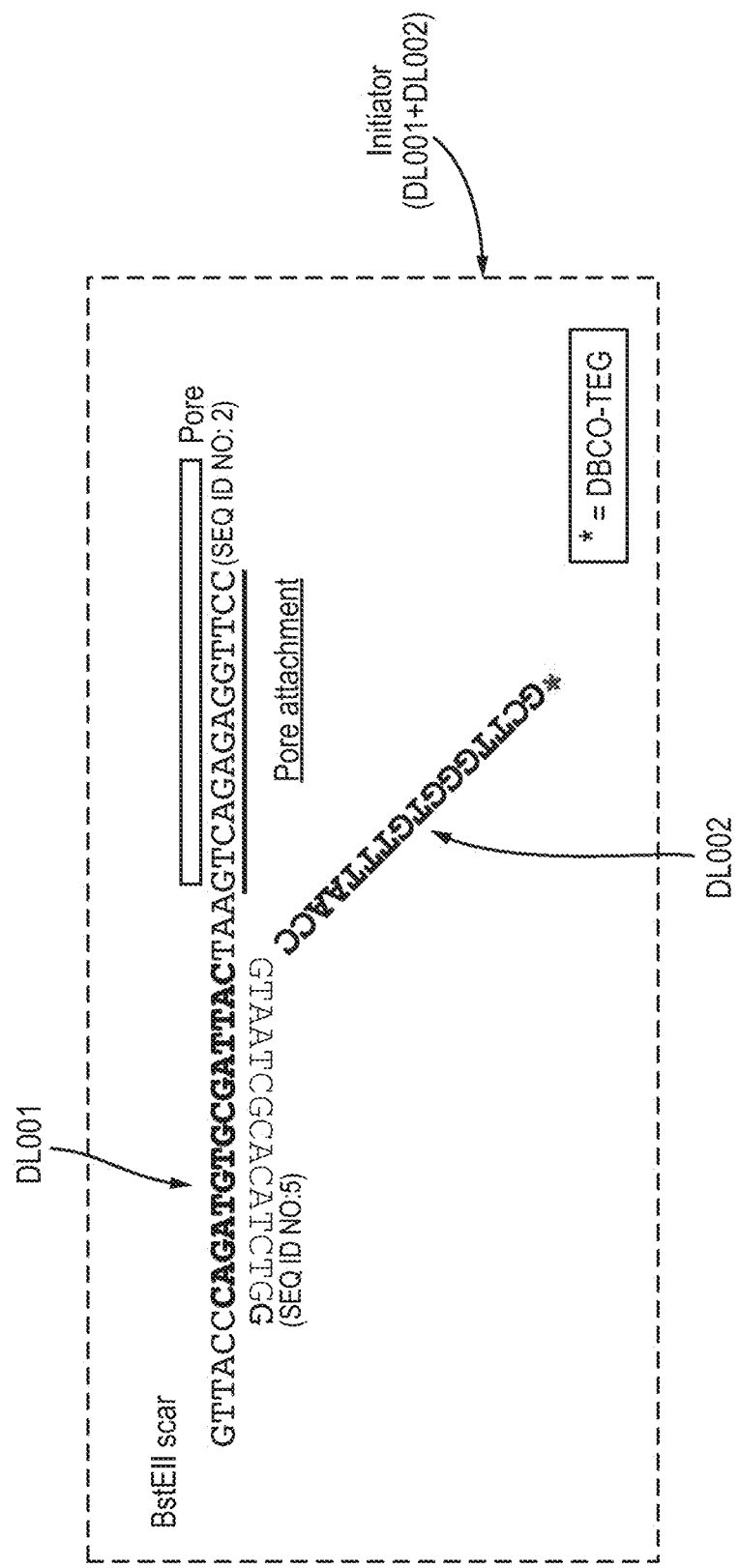
FIG. 19 shows an example overview of attachment of a polynucleotide synthesis molecule to a nanopore. Sequences correspond to SEQ ID NOs: 2-5.
Figure 20:
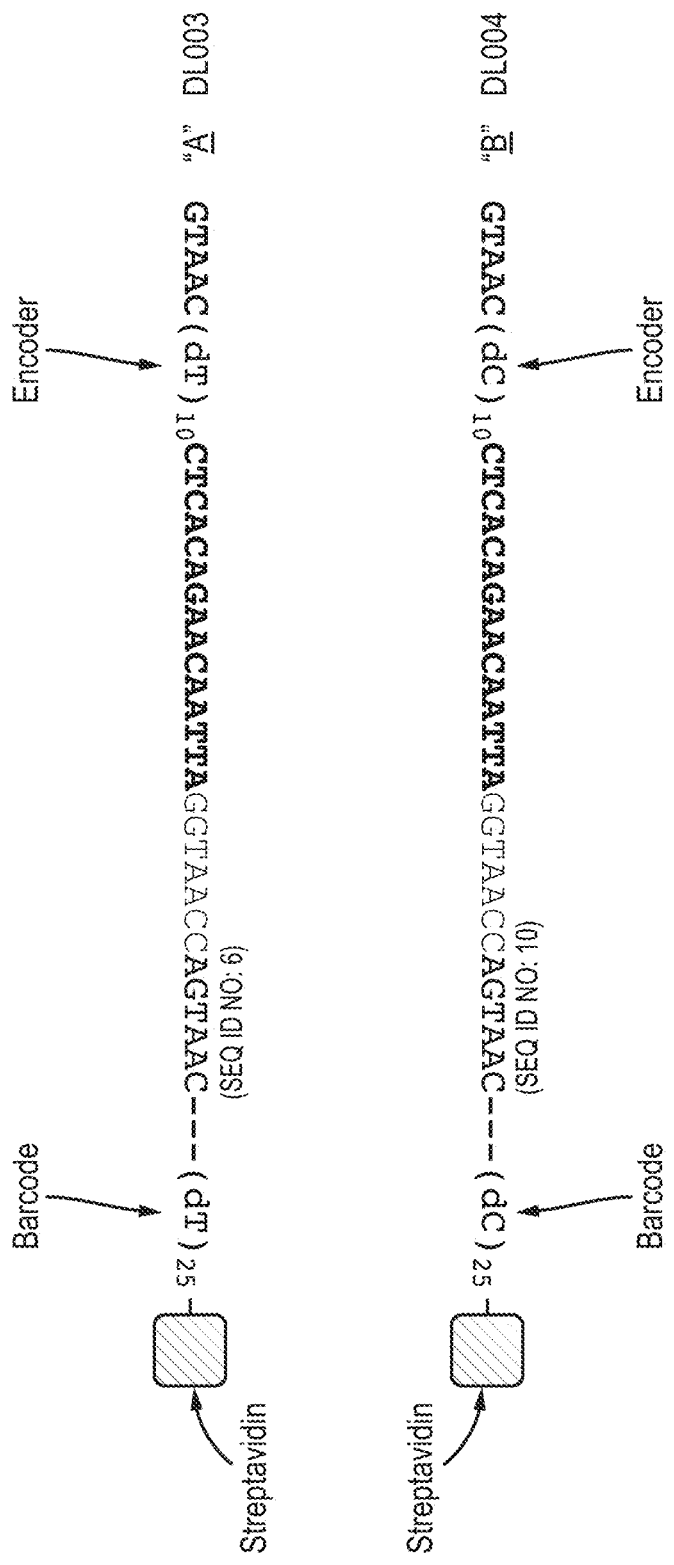
FIG. 20 shows an example of feeder molecules. Sequences correspond to SEQ ID NOs: 6-12.
Figure 21:
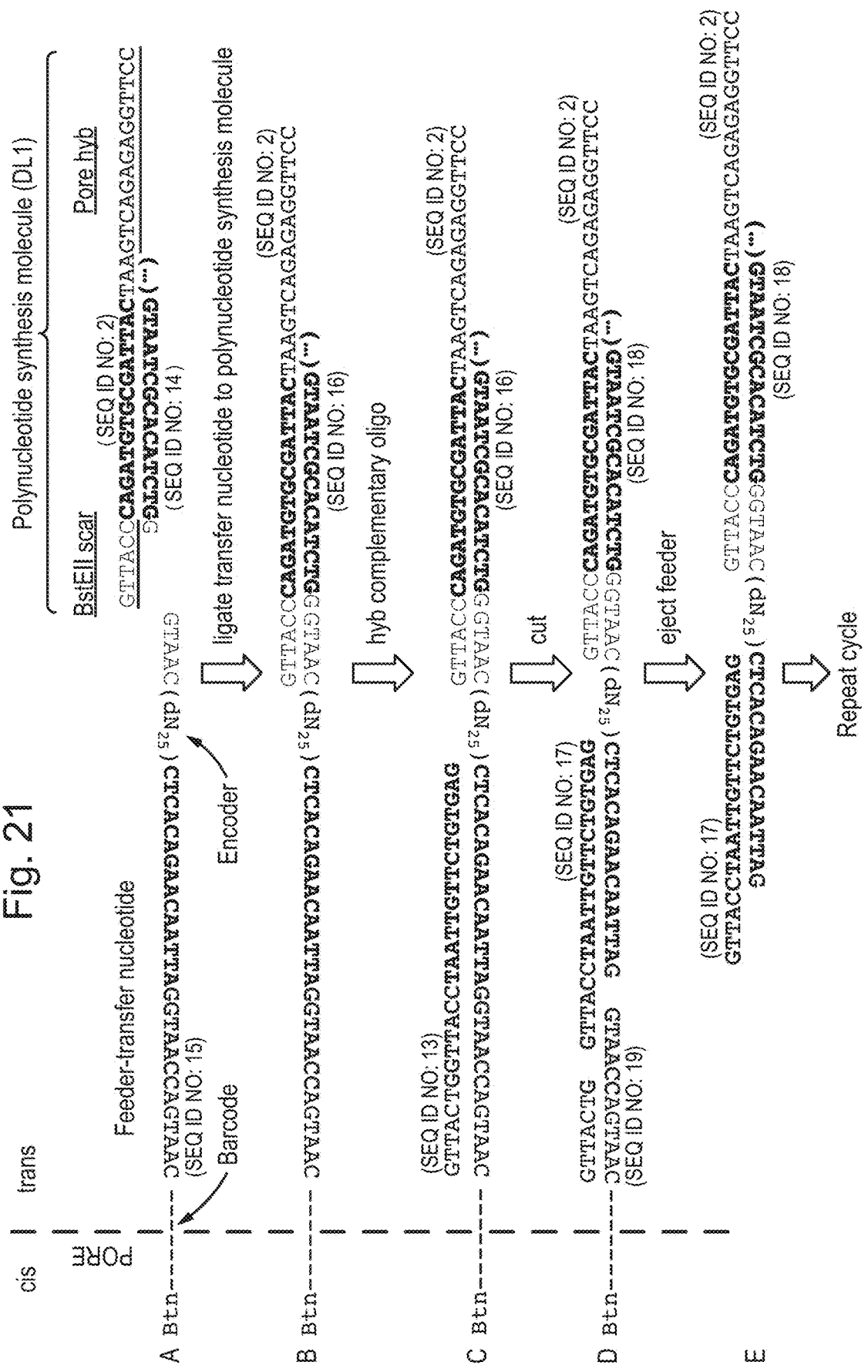
FIG. 21 shows an example overview of a method according to the invention involving ligation. Sequences correspond to SEQ ID NOs: 2 and 14-19.

The sequences described in this example are shown in Table 1 and in FIGS. 19-21. The polynucleotide synthesis molecule (DL2) is hybridized to a complementary oligonucleotide (DL1), which hybridises to the nanopore tether to retain the polynucleotide synthesis molecule on the nanopore. The feeder-transfer nucleotide molecules DL3 ("A") and DL4 ("B") are shown in FIG. 20. They include elements of (see Table 1):

- a barcode portion in the feeder, for identification when captured in the nanopore, in this case either polydT or polydC;
- a universal sequence, for hybridisation of a complementary oligonucleotide (DL5) contained in the trans solution;
- an encoder sequence for encoding the stored information; in this case either polydT or polydC;
- a sequence bearing complementarity to the overhang generated by a restriction endonuclease; in this case 5'-GTAAC
- a 3'-biotin-streptavidin linkage, for attaching a blocker streptavidin to retain the feeder molecule in the nanopore.

An exemplary method for repeatedly extending the initiator is as follows:

- a polynucleotide synthesis DNA molecule (DL2+DL1 bearing a 3'-sticky recess for the incoming transfer nucleotide) is first hybridized to the nanopore tether on the trans side of the nanopore (FIG. 19);
- a feeder-transfer nucleotide molecule bearing a barcode is captured from the cis volume and partially translocates under positive potential applied to cis (e.g. +100 mV) through the nanopore, and is held in the nanopore by the biotin-streptavidin linkage (FIG. 21A);
- the feeder-transfer nucleotide molecule is identified by the barcode region in the nanopore via the current flowing through the nanopore measured while it is held in the nanopore;
- if the incorrect feeder molecule is captured and the potential is either reversed (e.g. −20 mV) or reduced to a lower applied potential (e.g. +20 mV) to eject the feeder molecule, and once ejected the voltage is applied again to capture another feeder molecule (e.g. +100 mV);
- If the correct transfer nucleotide is detected the voltage is held at a moderate voltage to retain the transfer nucleotide (e.g. +50 to +100 mV) to permit the following reactions to occur:
  - a DNA ligase (e.g. T3 or T4 DNA ligase) provided in trans ligates the sticky 5'-phosphorylated/5Phos/GTAAC end of the transfer nucleotide (DL3 or DL4) to the 3'end of the polynucleotide synthesis molecule (DL2) (FIG. 21B). The restriction endonuclease cannot cleave the ligated product because it leaves a scar site with the incorrect sequence for the restriction enzyme;
  - a blocker oligonucleotide complementary to the universal portion of the feeder molecule hybridises to the feeder-transfer nucleotide molecule in trans, forming a restriction endonuclease cut site (e.g. the sequences described are designed for cutting by the BstE II restriction enzyme) (FIG. 21C);
  - a suitable restriction enzyme (e.g. BstE II) provided in trans cleaves the feeder molecule from the transfer nucleotide (FIG. 21D);
- Ideally the feeder molecule is spontaneously lost from the nanopore back to the cis side upon cutting as the reduced length is insufficient to retain it in the nanopore under the moderate voltage conditions (FIG. 21E). Alternatively, the voltage can be reduced to zero or a low voltage (e.g. +20 mV to −20 mV) to test if the transfer nucleotide can be ejected (i.e. restriction cutting has occurred).
- After successful extension the cycle may be repeated an arbitrary number of times to further extend the synthesis polynucleotide.
- At the end of the synthesis cycles, the final polynucleotide synthesis molecule can be characterised on the same nanopore by nanopore sequencing. For example, the example sequence for the polynucleotide synthesis molecule (DL2) contains a 5' click-reactive DBCO group permitting attachment of a nanopore sequencing adapter, which can then be captured in the nanopore under a high negative applied voltage (e.g. −180 mV) for sequencing and verification of the ligated sequence.

Detailed Description of the Example

Feeder-transfer nucleotide-monovalent streptavidin conjugates are formed by incubating monovalent streptavidin (500 nM tetramer) with 250 nM DL3 and 250 nM DL4 in 5 mL of buffer (25 mM potassium phosphate, 150 mM potassium ferricyanide, 150 mM ferrocyanide, pH 8.0) to create a trans-mix solution.

Electrochemical flow cells containing multiple wells (each comprising reaction chambers such as described herein) are prepared entrapping the feeder-transfer nucleotide-monovalent streptavidin conjugates in the wells by filling the wells with trans-mix solution, forming block co-polymer membranes on top of the wells, and filling the top chamber of the flow cell with buffer (25 mM potassium phosphate, 150 mM potassium ferricyanide, 150 mM ferrocyanide, pH 8.0). Biological nanopores bearing a single morpholino oligonucleotide attachment tether (Sequence: 5'-GGAACCTCTCTGACAA (SEQ ID NO: 1)-linker-3'-nanopore) are inserted into the membranes. Excess pore is flushed from the flow cell with buffer (25 mM potassium phosphate, 150 mM potassium ferricyanide, 150 mM ferrocyanide, pH 8.0).

The polynucleotide synthesis molecule is formed by annealing 40 µM of DL001 and 40 µM DL002 in Duplex Annealing Buffer (Integrated DNA Technologies, Inc.). The mix is heated to 95° C. and slowly cooled to room temperature at a rate of −0.1° C./min. Polynucleotide synthesis molecule is attached to the pore by flowing 150 µL of a 1 µM solution of polynucleotide synthesis molecule in Synthesis Buffer (25 mM HEPES-KOH (pH 8.0 at 37° C.), 400 mM potassium glutamate, 20 mM magnesium acetate, 10 mM ATP) into the flow cell and incubating the flow cell for 15 min. Excess polynucleotide synthesis molecule is then removed from the flow cell by flushing 500 µL Synthesis Buffer through the flow cell.

Synthesis Mix (150 µL) is then introduced into the flow cell as follows: 10 units BstEII restriction endonuclease (NEB, Cat. #R0162); 3,000 units T3 DNA Ligase (NEB, Cat #M0317); 1 µM DL005, in Synthesis Buffer.

Synthesis is initiated at 34° C. by applying the following voltage scheme to selected wells of the flow cell, thereby leaving polynucleotide synthesis molecule attached to nanopores in non-selected wells unmodified as internal controls:

+180 mV to the top chamber of the flow cell, 1 min, to permit capture of the feeder-streptavidin conjugate and time for the ligation and restriction reactions to occur. The identity of the captured feeder-transfer nucleotide is identified by the current level signature, as determined by the base composition in the nanopore (polyT or polyC for the DL3 and DL4 transfer nucleotides respectively);

−20 mV to the top chamber of the flow cell, for 0.1 sec, to eject the feeder if the blocker is not hybridized;

Repeat the above for 20 cycles.

The scheme above is a non-feedback system without software monitoring that does not control which feeder-transfer nucleotide is captured in any one cycle, and hence extends the polynucleotide synthesis molecule with a random pattern of DL3 and DL4 units.

Following the above scheme, the flow cell is prepared for sequencing.

Sequencing of the polynucleotide synthesis molecule is carried out using standard nanopore sequencing protocols. Sequencing of the system is used to validate the effectiveness of the synthesis. In those wells where no voltage synthesis scheme is applied, only adapters with un-extended polynucleotide synthesis molecule are observed. In the wells where the synthesis voltage cycle is applied the polynucleotide synthesis molecules are extended, and the sequence of the extended polynucleotide synthesis molecules in each separate nanopore channel reflects the order in which the transfer nucleotides have been captured. The data from the sequencing is compared to the currents recorded during the synthesis cycle to measure the effectiveness of synthesis.

TABLE 1

| | Sequence | Purpose |
|---|---|---|
| DL1 | 5'-GTTACCCAGATGTGCGATTACTAAGTCAGAGAGGTTCC-3' (SEQ ID NO: 2) GTCAGAGAGGTTCC = pore attachment (SEQ ID NO: 3) TAA = intervening sequence CAGATGTGCGATTAC = Polynucleotide synthesis molecule complementary sequence (SEQ ID NO: 4) GTTACC = BstEII scar | Polynucleotide synthesis molecule complement (hybridizes to pore) |
| DL2 | 5'-/5DBCOTEG/GCTTGGGTGTTTAACCGTAATCGCACATCTGG-3' (SEQ ID NO: 5) | Polynucleotide synthesis molecule |
| DL3 | 5'-/5Phos/GTAACttttttttttCTCACAGAACAATTAGGTAACCAGTAACTTTTTTTTTTTTTTTTTTTTTTT/3BioTEG/-3' (SEQ ID NO: 6) GTAAC = a sequence bearing complementarity to the overhang generated by a restriction endonuclease tttttttttt = encoder sequence for encoding the stored information (SEQ ID NO: 7) CTCACAGAACAATTAGGTAACCAGTAAC = a universal sequence, for hybridisation of a complementary oligonucleotide (DL5) (SEQ ID NO: 8) TTTTTTTTTTTTTTTTTTTTTTTTT = Barcode (SEQ ID NO: 9) 3BioTEG = a 3'-biotin-streptavidin linkage, for attaching a blocker streptavidin to retain the feeder molecule in the nanopore | Feeder molecule (a) attached to transfer nucleotide (A) |
| DL4 | 5'-/5Phos/GTAACccccccccccCTCACAGAACAATTAGGTAACCAGTAACCCCCCCCCCCCCCCCCCCCCCCCC/3BioTEG/-3' (SEQ ID NO: 10) GTAAC = a sequence bearing complementarity to the overhang generated by a restriction endonuclease cccccccccc = encoder sequence for encoding the stored information (SEQ ID NO: 11) CTCACAGAACAATTAGGTAACCAGTAAC = a universal sequence, for hybridisation of a complementary oligonucleotide (DL5) (SEQ ID NO: 8) CCCCCCCCCCCCCCCCCCCCC CCCCC = barcode (SEQ ID NO: 12) 3BioTEG = a 3'-biotin-streptavidin linkage, for attaching a blocker streptavidin to retain the feeder molecule in the nanopore | Feeder molecule (b) attached to transfer nucleotide (B) |
| DL5 | 5'-GTTACTGGTTACCTAATTGTTCTGTGAG-3' (SEQ ID NO: 13) | Hybridization oligonucleotide |

Figure 22:
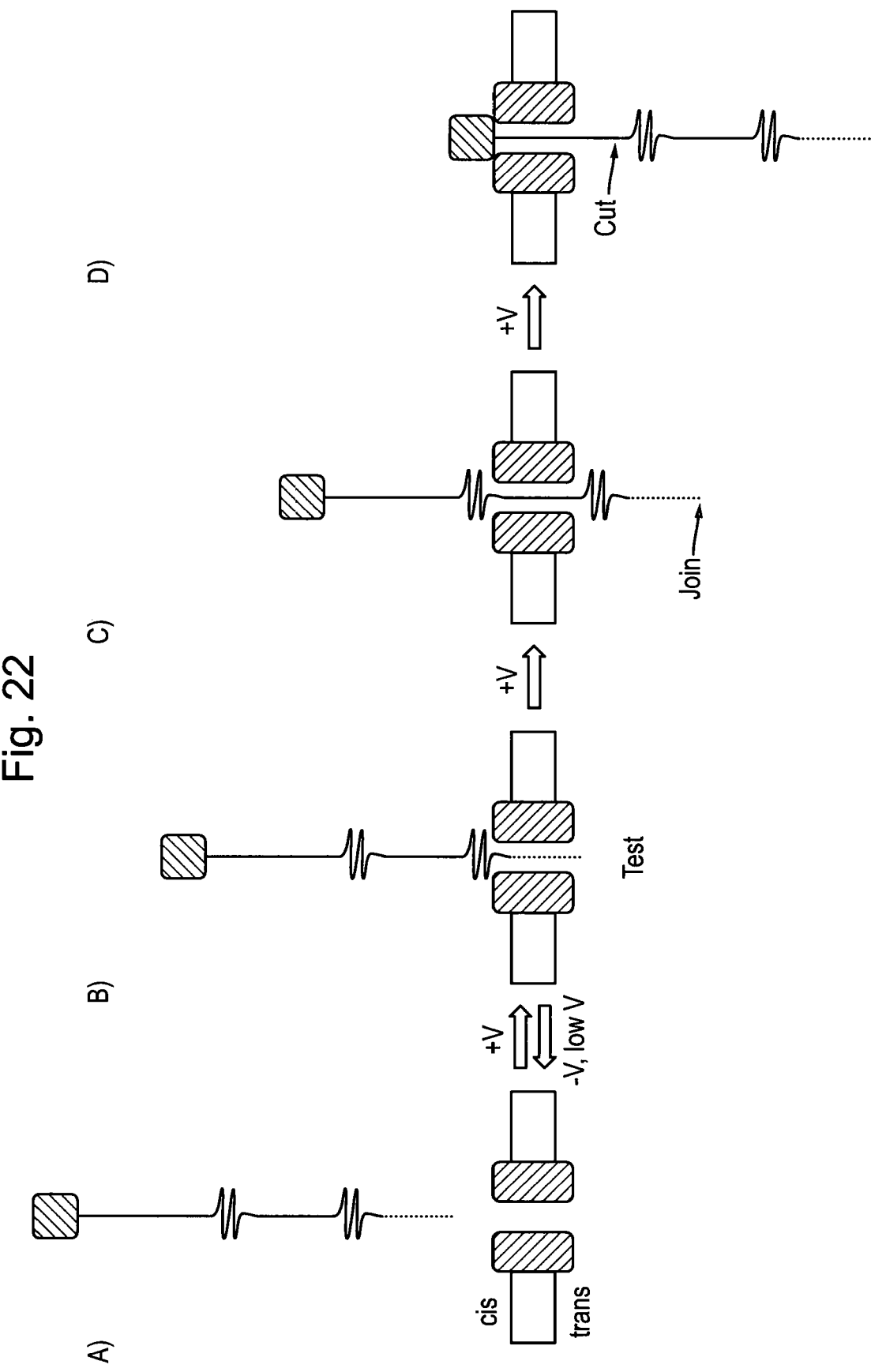
FIG. 22 shows an example overview of stepped control of a feeder molecule in a nanopore.

Example 6—Sequential Stepping of a Transfer Nucleotide and/or Feeder Molecule Through a Nanopore FIG. 22 illustrates how multiple blockers can be used to sequentially step a transfer nucleotide and/or feeder molecule through a nanopore. Sequential stepping enables separation of different reaction processes over time. For example, the figure illustrates how a feeder molecule with successive temporary blockers (e.g. secondary structures such as a quadruplex) can be used to step the molecule through a nanopore from the cis side to the trans side in multiple stages by controlling the applied voltage. The system can be controlled by feedback software that monitors the current signal and adjusts the voltage accordingly. The figure illustrates how a transfer nucleotide attached to a feeder molecule can first be captured in the nanopore under positive applied voltage (step A>B). In step B) the molecule can be held in the nanopore at a moderate holding voltage sufficient to prevent escape but insufficient to overcome the blocker (e.g. 40 to 100 mV), enabling time to assess the identity of the molecule captured. In this state, ideally the attachment joining process to the polynucleotide synthesis molecule (e.g. by ligation) cannot occur because the end of the transfer nucleotide is sterically hindered from binding the ligase or the polynucleotide synthesis molecule. In state B), if the incorrect species of transfer nucleotide is determined to have been captured the voltage can be reduced or reversed to eject it back to the cis side (B>A). If transfer nucleotide is determined to be the desired species the voltage can be increased to overcome the blocker to continue to pass the strand through to the trans side (B>C). The figure illustrates in step C) that the transfer nucleotide can be held (e.g. under a moderate or zero applied voltage, e.g. 0 to 100 mV) to enable the joining reaction (e.g. by ligation) to the synthesis nucleotide to occur. After a desired period, e.g. sufficient to ensure high probability of successful joining, the transfer nucleotide can then be progressed C>D to expose the cutting region to the cutting chemistry. In this way the step scheme enables more control over the detection, joining and cutting phases. Separating the detection and joining phases helps ensure that the wrong transfer nucleotide is not joined to the polynucleotide synthesis molecule, and separating the joining and cutting phases helps prevent the transfer nucleotide being lost to the trans solution before the joining has occurred.

Voltage Schemes:

Suitable blockers are known in the art. For example, secondary structures such as dsDNA hybs, hairpins, quadruplexes can all be used to temporarily pause a polynucleotide under a moderate applied voltage. These sorts of blockers can also be overcome by the application of higher voltage to unzip the hybridization. The higher applied voltages can be applied for a brief amount of time to move the strand forward, and quickly dropped to a lower voltage upon detecting a current change due to the polynucleotide progressing forwards. Alternatively, the voltage may be increased in short pulses in an attempt to probabilistically move the strand forward, interspersed with moderate hold voltages to measure the current to determine whether the strand has progressed.

Figure 23:
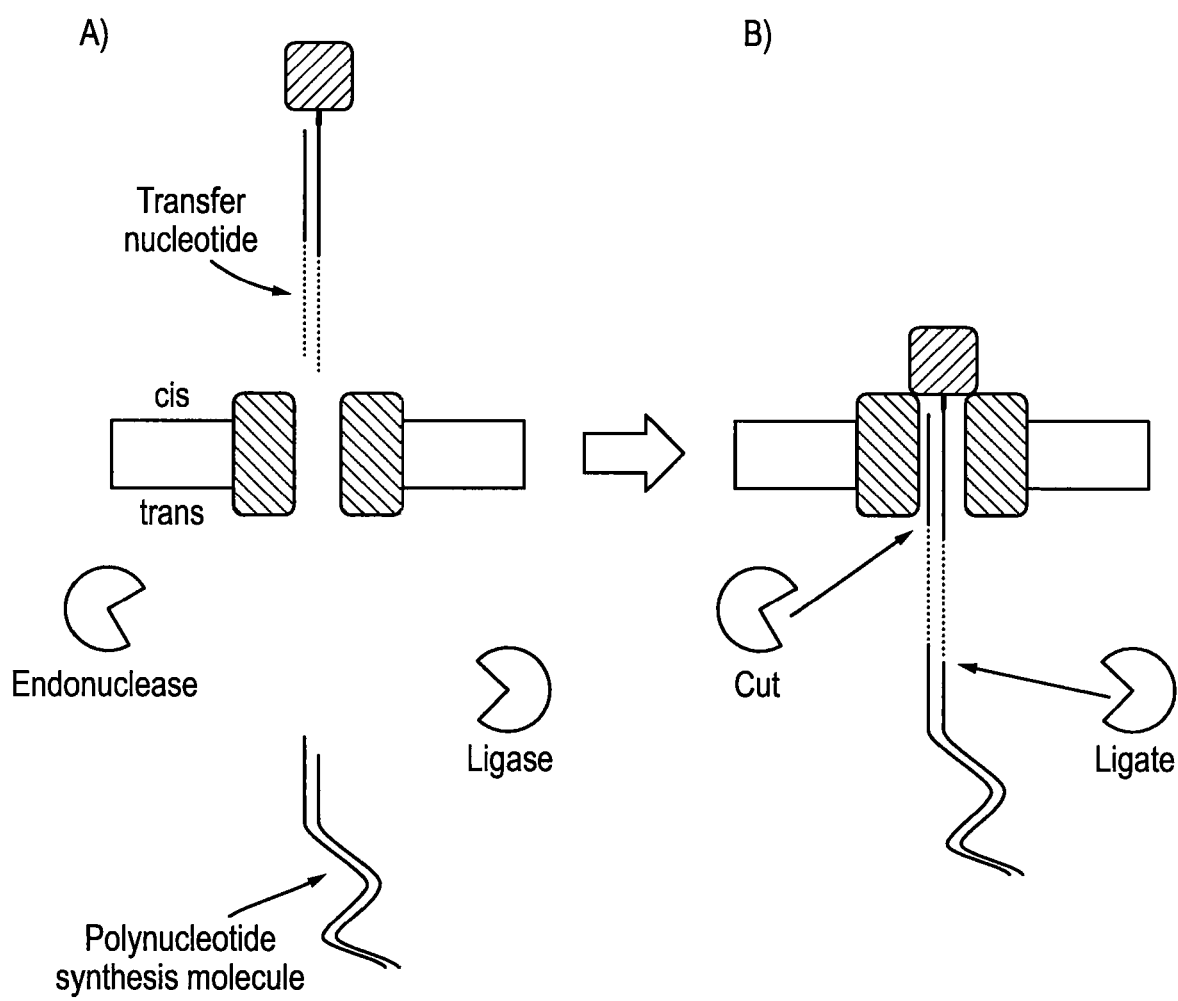
FIG. 23 shows a further example overview of a method according to the invention involving ligation.

Example 7—Delivery of Intact Double Stranded Transfer Nucleotides Through a Nanopore FIG. 23 illustrates the delivery of intact double stranded transfer nucleotides through a nanopore to extend a polynucleotide synthesis molecule. This system can be achieved through the use of large channel nanopores that can pass double strand polynucleotide intact (no unzipping), for example nanopore including ClyA, Phi29, or other pores in the range of about 3 nm to about 10 nm. FIG. 23 shows an example of how a dsDNA transfer nucleotide passed intact through a nanopore can be joined to a polynucleotide synthesis molecule (e.g. by ligation). The dsDNA transfer nucleotide can optionally be cut from a feeder molecule (e.g. by a restriction enzyme).

Figure 24:
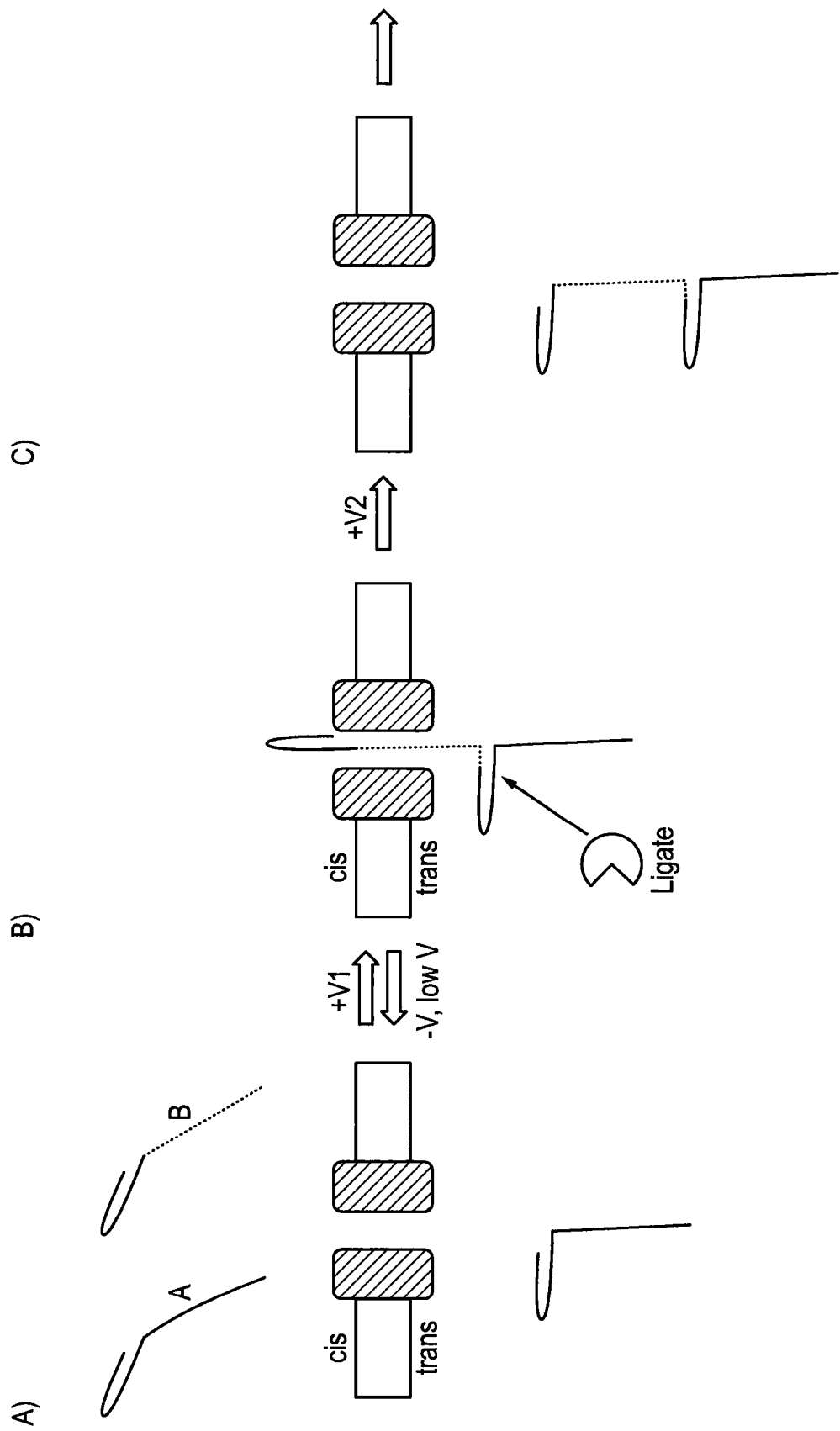
FIG. 24 shows a further example overview of a method according to the invention involving ligation.

Example 8—Further Example of Ligation-Mediated Extension of a Polynucleotide Synthesis Molecule FIG. 24 illustrates a further ligation example, but without the requirement for detaching the transfer nucleotide from a feeder molecule. In step A)>B) a transfer nucleotide with a secondary structure is captured in the nanopore and partially translocated. The secondary structure (e.g. a hairpin dsDNA section as illustrated) prevents full translocation under a medium applied voltage. During capture the transfer nucleotide can be measured to determine whether the desired transfer nucleotide has been captured from the available pool, and if the incorrect species is captured it can be ejected back (by reducing or reversing the applied voltage). The transfer nucleotide can be held in the nanopore under a medium applied voltage to enable sufficient time for the translocated portion to attach to the polynucleotide synthesis molecule. Attachment can be mediated by enzymatic catalysis, for example via ligases included on the side containing the polynucleotide synthesis molecule. Ligation can be improved by designing the components as shown in figure to create short sections of dsDNA to splint the gap being joined. For example, the transfer nucleotide can be designed to include a hairpin section of dsDNA, which can rehybridise after being unzipped during translocation through the nanopore, forming a short complementary hybridisation region that splints the delivered end of the transfer nucleotide. Alternatively, sections of dsDNA to splint ligation can be created by inclusion of complementary oligonucleotide strands in the compartment containing the polynucleotide synthesis molecule. After ligation the transfer nucleotide can be fully translocated through the nanopore by brief application of high voltage to overcome the secondary/blocking structure. FIG. 24 illustrates how the hairpin reforms after translocation to provide a site for attaching the next transfer nucleotide. The process can be repeated to continue extending the polynucleotide synthesis molecule, picking which transfer nucleotides are passed through for attachment.

It is to be understood that different applications of the disclosed methods and products may be tailored to the specific needs in the art. It is also to be understood that the terminology used herein is for the purpose of describing particular embodiments of the invention only, and is not intended to be limiting.

As used in this specification and the appended claims, the singular forms "a", "an", and "the" include plural referents unless the content clearly dictates otherwise. Thus, for example, reference to "a ligation polynucleotide" includes two or more such polynucleotides, reference to "a scaffold polynucleotide" includes two or more such scaffold polynucleotides, and the like.

All publications, patents and patent applications cited herein are hereby incorporated by reference in their entirety.

The invention claimed is:

1. A method of extending a polynucleotide synthesis molecule with a transfer nucleotide, the method comprising an extension process comprising moving the transfer nucleotide through the channel of a nanopore disposed in a substrate from the cis side to the trans side of the substrate, and contacting the transfer nucleotide with an enzyme provided on the trans side of the substrate adjacent the nanopore whereupon the enzyme catalyses the transfer of the transfer nucleotide to the polynucleotide synthesis molecule thereby extending the polynucleotide synthesis molecule,
wherein the transfer nucleotide is attached to a feeder molecule and wherein the transfer nucleotide is cleaved from the feeder molecule prior to incorporation into the polynucleotide synthesis molecule.

2. The method according to claim 1, wherein the transfer nucleotide is an unblocked nucleotide.

3. The method according to claim 1, wherein the transfer nucleotide is cleaved by the enzyme.

4. The method of extending a polynucleotide synthesis molecule with a transfer nucleotide according to claim 1, the method comprising an extension process comprising:
A. providing a substrate comprising a nanopore, wherein the nanopore comprises a channel allowing fluid flow from the cis side to the trans side of the substrate; providing a feeder molecule at the cis side of the substrate, the feeder molecule having an attached transfer nucleotide; providing an enzyme and the polynucleotide synthesis molecule in proximity to each other on the trans side of the substrate adjacent the nanopore; and
B. moving the feeder molecule through the nanopore to bring the attached transfer nucleotide into contact with the enzyme whereupon the enzyme catalyses the transfer of the transfer nucleotide to the polynucleotide synthesis molecule thereby extending the polynucleotide synthesis molecule.

5. The method according to claim 4, further comprising:
C. moving the feeder molecule through the nanopore to the cis or trans side of the substrate following transfer of the transfer nucleotide to the polynucleotide synthesis molecule.

6. The method according to claim 1, wherein the polynucleotide synthesis molecule is provided having a proximal terminus adjacent to the enzyme and a distal terminus, wherein the enzyme catalyses the addition of the transfer nucleotide to the proximal terminus of the polynucleotide synthesis molecule.

7. The method according to claim 1, wherein feeder molecules are provided at the cis side of the substrate having differing attached transfer nucleotides.

8. The method according to claim 7, wherein the cis side of the substrate comprises a mixture of feeder molecules in the same reaction volume, wherein the mixture comprises different populations of feeder molecules, wherein each feeder molecule of a population has the same transfer nucleotide attached, and wherein the different populations of feeder molecule have different transfer nucleotides attached.

9. The method according to claim 7, wherein feeder molecules having differing attached transfer nucleotides are distinguishable.

10. The method according to claim 9, wherein a feeder molecule is capable of providing an identifiable signal to uniquely identify the attached transfer nucleotide and/or to determine the integrity of the attached transfer nucleotide.

11. The method according to claim 10, comprising performing a first verification process to determine the identity and/or integrity of the transfer nucleotide of the feeder molecule, wherein:
a) if the feeder molecule is determined to have the desired transfer nucleotide attached, moving the feeder molecule to bring the transfer nucleotide into contact with the enzyme; or
b) if the feeder molecule is determined not to have the desired transfer nucleotide attached:
i. moving the feeder molecule to the cis or trans side of the substrate;
ii. moving a feeder molecule from the mixture of feeder molecules at the cis side of the substrate into the nanopore towards the trans side; and
iii. repeating the first verification process until the feeder molecule is determined to have the desired transfer nucleotide attached, following which the feeder molecule is moved to bring the transfer nucleotide into contact with the enzyme;

optionally wherein the first verification process is performed whilst the feeder molecule is at least partially within the channel of the nanopore.

12. The method according to claim 10, wherein a feeder molecule is capable of providing a different identifiable signal when the transfer nucleotide is no longer attached to the feeder molecule.

13. The method according to claim 12, comprising a step (C) of moving the feeder molecule through the nanopore to the cis or trans side of the substrate following transfer of the transfer nucleotide to the polynucleotide synthesis molecule, wherein step (C) is performed only following a second verification process performed to verify that the enzyme has catalysed the transfer of the transfer nucleotide from the feeder molecule to the polynucleotide synthesis molecule, wherein the second verification process comprises:

I. moving the feeder molecule through the nanopore in the cis direction, and determining the presence or absence of the nucleobase of the transfer nucleotide;

II. moving the feeder molecule back in the trans direction to bring the nucleotide into contact with the enzyme if the nucleobase of the transfer nucleotide is determined to be attached to the feeder molecule; and III. repeating steps (I) and (II) until the desired transfer nucleotide is determined to have been removed from the feeder molecule.

14. The method according to claim 10, wherein the identity and/or integrity of the nucleobase and/or the presence or absence of the transfer nucleotide attached to the feeder molecule is determined by measurement of the feeder molecule.

15. The method according to claim 14, wherein measurement of the feeder molecule is with respect to the nanopore.

16. The method according to claim 15, wherein the feeder molecule is measured by measuring ion current flow through the nanopore under the action of a potential difference applied across the substrate; optionally wherein a change in the ion current flowing through the nanopore is dependent upon the presence and/or structure of the nucleobase of the nucleotide and thereby provides the identifiable signal to uniquely identify the transfer nucleotide and/or to determine the absence, presence and/or integrity of the transfer nucleotide.

17. The method according to claim 16, wherein changes in the ion current flowing through the nanopore are dependent upon the presence of a pre-defined sequence of nucleobases integral to the feeder molecule (barcode) and which thereby provides the identifiable signal to uniquely identify the transfer nucleotide.

18. The method according to claim 1 wherein the identity and/or structure of the transfer nucleotide is pre-defined.

19. The method according to claim 1, wherein the nanopore is a biological nanopore; a synthetic nanopore; a solid state nanopore; or a hybrid nanopore comprising a biological or synthetic nanopore disposed within a solid state substrate.

20. The method according to claim 1 wherein the feeder molecule comprises a sequence of nucleotides (barcode) capable of uniquely identifying a feeder molecule and the type of transfer nucleotide attached thereto.

21. The method according to claim 1, wherein the feeder molecule comprises one or more blocking moieties, wherein a blocking moiety is provided at a position on the feeder molecule so that when the feeder molecule is moved into a nanopore to a position of interest in the nanopore, the blocking moiety acts to inhibit further translocation of the feeder molecule in the trans direction; optionally wherein one or more blocking moieties comprises a reversible blocking moiety; wherein the one or more blocking moieties are provided along the length of the feeder molecule and/or are provided at a terminal end of the feeder molecule and/or are provided as an integral part of the feeder molecule; optionally wherein a blocking moiety is a molecule attached to the feeder molecule; further optionally wherein a blocking moiety is a peptide, oligopeptide, polypeptide, protein or other polymer.

* * * * *

UNITED STATES PATENT AND TRADEMARK OFFICE
CERTIFICATE OF CORRECTION

| | | |
|---|---|---|
| PATENT NO. | : 12,195,777 B2 | Page 1 of 1 |
| APPLICATION NO. | : 16/966430 | |
| DATED | : January 14, 2025 | |
| INVENTOR(S) | : Andrew John Heron | |

It is certified that error appears in the above-identified patent and that said Letters Patent is hereby corrected as shown below:

On the Title Page

Item (71), the Applicant is hereby corrected as shown below:
(71) Applicant: Oxford Nanopore Technologies PLC,
              Oxford (GB)

Signed and Sealed this
Tenth Day of June, 2025

Coke Morgan Stewart
*Acting Director of the United States Patent and Trademark Office*

SEQUENCE LISTING

<160> NUMBER OF SEQ ID NOS: 19

<210> SEQ ID NO 1
<211> LENGTH: 16
<212> TYPE: DNA
<213> ORGANISM: Artificial Sequence
<220> FEATURE:
<223> OTHER INFORMATION: Nucleic acid portion of morpholino
      oligonucleotide attachment tether

<400> SEQUENCE: 1
ggaacctctc tgacaa                                                         16

<210> SEQ ID NO 2
<211> LENGTH: 38
<212> TYPE: DNA
<213> ORGANISM: Artificial Sequence
<220> FEATURE:
<223> OTHER INFORMATION: Polynucleotide synthesis molecule complement
      (hybridizes to pore) (DL1)

<400> SEQUENCE: 2
gttacccaga tgtgcgatta ctaagtcaga gaggttcc                                 38

<210> SEQ ID NO 3
<211> LENGTH: 14
<212> TYPE: DNA
<213> ORGANISM: Artificial Sequence
<220> FEATURE:
<223> OTHER INFORMATION: pore attachment (DL1)

<400> SEQUENCE: 3
gtcagagagg ttcc                                                           14

<210> SEQ ID NO 4
<211> LENGTH: 15
<212> TYPE: DNA
<213> ORGANISM: Artificial Sequence
<220> FEATURE:
<223> OTHER INFORMATION: Polynucleotide synthesis molecule complementary
      sequence (DL1)

<400> SEQUENCE: 4
cagatgtgcg attac                                                          15

<210> SEQ ID NO 5
<211> LENGTH: 32
<212> TYPE: DNA
<213> ORGANISM: Artificial Sequence
<220> FEATURE:
<223> OTHER INFORMATION: Polynucleotide synthesis molecule (DL2)

<400> SEQUENCE: 5
gcttgggtgt ttaaccgtaa tcgcacatct gg                                       32

<210> SEQ ID NO 6
<211> LENGTH: 68
<212> TYPE: DNA
<213> ORGANISM: Artificial Sequence
<220> FEATURE:
<223> OTHER INFORMATION: Feeder molecule (a) attached to transfer
      nucleotide (A) (DL3)

<400> SEQUENCE: 6 gtaactttt tttttctcac agaacaatta ggtaaccagt aactttttt tttttttttt           60 tttttttt                                                                  68

```
<210> SEQ ID NO 7
<211> LENGTH: 10
<212> TYPE: DNA
<213> ORGANISM: Artificial Sequence
<220> FEATURE:
<223> OTHER INFORMATION: encoder sequence for encoding the stored
      information (DL3)

<400> SEQUENCE: 7
tttttttttt                                                              10

<210> SEQ ID NO 8
<211> LENGTH: 28
<212> TYPE: DNA
<213> ORGANISM: Artificial Sequence
<220> FEATURE:
<223> OTHER INFORMATION: a universal sequence, for hybridisation of a
      complementary oligonucleotide (DL5)

<400> SEQUENCE: 8
ctcacagaac aattaggtaa ccagtaac                                          28

<210> SEQ ID NO 9
<211> LENGTH: 25
<212> TYPE: DNA
<213> ORGANISM: Artificial Sequence
<220> FEATURE:
<223> OTHER INFORMATION: Barcode (DL3)

<400> SEQUENCE: 9
tttttttttt tttttttttt ttttt                                             25

<210> SEQ ID NO 10
<211> LENGTH: 68
<212> TYPE: DNA
<213> ORGANISM: Artificial Sequence
<220> FEATURE:
<223> OTHER INFORMATION: Feeder molecule (b) attached to transfer
      nucleotide (B) (DL4)

<400> SEQUENCE: 10
gtaacccccc ccccctcac agaacaatta ggtaaccagt aaccccccccc cccccccccc       60 cccccccc                                                                68

<210> SEQ ID NO 11
<211> LENGTH: 10
<212> TYPE: DNA
<213> ORGANISM: Artificial Sequence
<220> FEATURE:
<223> OTHER INFORMATION: encoder sequence for encoding the stored
      information (DL4)

<400> SEQUENCE: 11
cccccccccc                                                              10

<210> SEQ ID NO 12
<211> LENGTH: 25
<212> TYPE: DNA
<213> ORGANISM: Artificial Sequence
<220> FEATURE:
<223> OTHER INFORMATION: barcode (DL4)

<400> SEQUENCE: 12
cccccccccc cccccccccc ccccc                                             25
```

```
<210> SEQ ID NO 13
<211> LENGTH: 28
<212> TYPE: DNA
<213> ORGANISM: Artificial Sequence
<220> FEATURE:
<223> OTHER INFORMATION: Hybridization oligonucleotide (DL5)

<400> SEQUENCE: 13
gttactggtt acctaattgt tctgtgag                                           28

<210> SEQ ID NO 14
<211> LENGTH: 16
<212> TYPE: DNA
<213> ORGANISM: Artificial Sequence
<220> FEATURE:
<223> OTHER INFORMATION: Portion of DL2 complementary to DL1 as shown in
      Figure 21A

<400> SEQUENCE: 14
gtaatcgcac atctgg                                                        16

<210> SEQ ID NO 15
<211> LENGTH: 58
<212> TYPE: DNA
<213> ORGANISM: Artificial Sequence
<220> FEATURE:
<223> OTHER INFORMATION: Feeder transfer nucleotide (feeder molecule) as
      shown in Figure 21A
<220> FEATURE:
<221> NAME/KEY: misc_feature
<222> LOCATION: (6)..(30)
<223> OTHER INFORMATION: n is a, c, g, or t

<400> SEQUENCE: 15
gtaacnnnnn nnnnnnnnnn nnnnnnnnnn ctcacagaac aattaggtaa ccagtaac         58

<210> SEQ ID NO 16
<211> LENGTH: 74
<212> TYPE: DNA
<213> ORGANISM: Artificial Sequence
<220> FEATURE:
<223> OTHER INFORMATION: Sequence of feeder transfer nucleotide ligated
      to DL2 as shown in Figures 21B and 21C
<220> FEATURE:
<221> NAME/KEY: misc_feature
<222> LOCATION: (22)..(46)
<223> OTHER INFORMATION: n is a, c, g, or t

<400> SEQUENCE: 16
gtaatcgcac atctgggtaa cnnnnnnnnn nnnnnnnnnn nnnnnctca cagaacaatt         60 aggtaaccag taac                                                          74

<210> SEQ ID NO 17
<211> LENGTH: 21
<212> TYPE: DNA
<213> ORGANISM: Artificial Sequence
<220> FEATURE:
<223> OTHER INFORMATION: Cleaved portion of hybridization
      oligonucleotide as shown in Figures 21D and 21E

<400> SEQUENCE: 17
gttacctaat tgttctgtga g                                                  21

<210> SEQ ID NO 18
<211> LENGTH: 62
<212> TYPE: DNA
<213> ORGANISM: Artificial Sequence
```

```
<220> FEATURE:
<223> OTHER INFORMATION: Cleaved portion of feeder transfer nucleotide
      ligated to DL2 as shown in Figures 21D and 21E
<220> FEATURE:
<221> NAME/KEY: misc_feature
<222> LOCATION: (22)..(46)
<223> OTHER INFORMATION: n is a, c, g, or t

<400> SEQUENCE: 18
gtaatcgcac atctgggtaa cnnnnnnnnn nnnnnnnnnn nnnnnnctca cagaacaatt     60
ag                                                                   62

<210> SEQ ID NO 19
<211> LENGTH: 12
<212> TYPE: DNA
<213> ORGANISM: Artificial Sequence
<220> FEATURE:
<223> OTHER INFORMATION: Cleaved portion of feeder transfer nucleotide
      ligated to DL2 as shown in Figure 21D

<400> SEQUENCE: 19
gtaaccagta ac                                                        12
```